US009695437B2

(12) United States Patent
Cheikh et al.

(10) Patent No.: US 9,695,437 B2
(45) Date of Patent: Jul. 4, 2017

(54) CONSTITUTIVE PHOTOMORPHOGENESIS 1 (COP1) NUCLEIC ACID SEQUENCE FROM ZEA MAYS AND ITS USE THEREOF

(71) Applicant: Monsanto Technology LLC, St. Louis, MO (US)

(72) Inventors: Nordine Cheikh, Davis, CA (US); Molian Deng, Grover, MO (US); Philip W. Miller, Ballwin, MO (US); Nanfei Xu, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 235 days.

(21) Appl. No.: 14/315,012

(22) Filed: Jun. 25, 2014

(65) Prior Publication Data
US 2015/0026841 A1 Jan. 22, 2015

Related U.S. Application Data

(62) Division of application No. 11/683,281, filed on Mar. 7, 2007, now Pat. No. 8,785,616, which is a division of application No. 10/229,436, filed on Aug. 28, 2002, now Pat. No. 7,208,652.

(60) Provisional application No. 60/315,593, filed on Aug. 29, 2001.

(51) Int. Cl.
*C12N 15/82* (2006.01)
*C07K 14/415* (2006.01)

(52) U.S. Cl.
CPC ........ *C12N 15/8269* (2013.01); *C07K 14/415* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 6,274,790 B1 | 8/2001 | Kunst et al. | |
| 6,278,041 B1 | 8/2001 | Lagrimini et al. | |
| 6,579,716 B1 * | 6/2003 | Deng | C07K 14/415 435/419 |
| 6,653,527 B1 | 11/2003 | Deng et al. | |
| 7,081,363 B2 | 7/2006 | Deng et al. | |
| 2007/0022495 A1 * | 1/2007 | Reuber | C07K 14/415 800/279 |

FOREIGN PATENT DOCUMENTS

| | | |
|---|---|---|
| WO | WO93/19189 | 9/1993 |
| WO | WO00/18940 | 4/2000 |

OTHER PUBLICATIONS

Bowie et al, "Deciphering the message in protein sequences: tolerance to amino acid substitutions," *Science*; 247:1306-1310; 1990.
Deng et al, "COP1, an Arabidopsis regulatory gene, encodes a protein with both a zinc-binding motif and a G homologous domain," *Cell*; 71:791-801; 1992.
Deng et al., "COP1, a regulatory locus involved in light-controlled development and gene expression in Arabidopsis, " *Genes Dev*; 5:1172-1182; 1991.
Deng, "Fresh view of light signal transduction in plants," *Cell*; 76:432-426; 1994.
Fluhr et al, "Organ-specific and light-induced expression of plant genes," *Science*; 232:1106-1112; 1986.
Green et al., "The role of antisense RNA in gene regulation," *Ann. Rev. Biochem*; 55:569-597; 1986.
Holm et al., Structural Organization and interactions of COP1 , a light-regulated developmental switch, *Plant Mol. Biol*; 41:151-158;1999.
Jarillo et al., Enlightenment of the COP1-HY5 complex in photomorphogenesis, TIPS, 3:161-163; 1998.
McConnell et al., Role of Phabulose and Phavoluta in determining radial patterning in shoots, *Nature*; 411:709-713; 2001.
McNellis et al., Expression of an N-terminal fragment of COP1 confers a dominant-negative effect on light-regulated seedling development in Arabidopsis; *Plant Cell*; 8:1491-1503; 1996.
McNellis et al., "Genetic and molecular analysis of an allelic series of COP1 mutants suggests functional roles for the multiple protein domains," *Plant Cell*; 6:487-500; 1994.
McNellis et al., Light control of seedling morphogenetic pattern; *Plant Cell*; 7:1749-1761; 1995.
McNellis et al., Overexpression of Arabidopsis COP1 results in partial suppression of light-mediated development evidence for a light-inactivable repressor of photomorphogeneis, *Plant Cell*; 6:1391-1400; 1994.
Mol et al., "Regulation of plant gene expression by antisense RNA," *FEBS Lett*; 268:427-430; 1990.
Osterlund et al., Multiple photoreceptors mediate the light-induced reduction of GUS-COP1 from Arabidopsis hypocotyl nyclei, *Plant Journal*; 16:201-208; 1998.
Osterlund et al., "The role of COP1 in repression of Arabidopsis photomorphogenic development," *Trends Cell biol.* ' 9:113-118; 1999.
Raghuvanshi, Isolation and molecular characterization of the COP1 gene homolog from rice, Oryza sativa L. subsp Indica var Pusa basmati 1, *DNA Res*; 8:73-79; 2001.
Stacey et al., Discrete domains mediate the light-responsive nuclear and cytoplasmic localization of COPA1, *Plant Cell*; 11:349-363;1999.
Stoop-Myer et al., "The N-terminal fragment of Arabidopsis photomorphogenic repressor Copt maintains partial function and acts in a concentration-dependent manner," *Plant Journal*; 20:713-717; 1999.
Sullivan et al., "The Pea light-independent photomorphogenesis 1 Mutant Results from Partial Duplication of COP1 Generating an Internal Promoter and Producing Two Distinct Transcripts," Plant Cell, 12:1927-1937, 2000.

(Continued)

*Primary Examiner* — Stuart F Baum
(74) *Attorney, Agent, or Firm* — Dentons US LLP; David Lanzotti, Esq.

(57) ABSTRACT

The present invention relates to an isolated COP1 nucleic acid sequence from a maize plant and the isolated COP1 nucleic acid sequence is named as ZmCOP1. The present invention also relates to a method of using the ZmCOP1 nucleic acid sequence to control the shade avoidance response of a crop plant for high density farming and yield enhancement.

10 Claims, 23 Drawing Sheets

(56) References Cited

OTHER PUBLICATIONS

Torii et al., "Functional dissection of Arabidopsis COP1 reveals specific roles of its three structural modules in light control of seedling development," The EMBO Journal, 17(19); 5577-5587, 1998.
Tsuge et al.,"Phytochrome-mediated control of COP1 gene expression in rice plants," *Mol Genet Genomics*; 265:43-50;2001.
Yamamoto et al., Role of COP1 interactive protein in mediating light-regulated gene expression in Arabidopsis, *Plant Cell.*, 10:1083-1094; 1998.
GenBank Accession No. AF029984, dated Jan. 1, 1999.
GenBank Accession No. AJ289774, dated Nov. 24, 2000.
GenBank Accession No. L24437, dated Sep. 22, 1993.
UniProtKB Accession No. P43254, dated Apr. 20, 2010.
UniProtKB Accession No. P93471, dated Apr. 20, 2010.
UniProtKB Accession No. Q9MAZ5, dated Oct. 31, 2006.
UniProtKB Accession No. Q9ZTV4, dated Oct. 31, 2006.

\* cited by examiner

```
ZmCOP1  ACTTTATGTGACAGCAGACGTGCACTGGCCAGGGGGATCACCATCCGTCGCCCCGGGTGT
AtCOP1  ------------------------------------------------------------

ZmCOP1  CAATAATATCACTCTGTACATCCACAAACAGACGATACGGCTCTCTCTTTTATAGGTGTA
AtCOP1  ------------------------------------------------------------

ZmCOP1  AACCTTAAACTGCCGTACGTATAGGCTGCGCAACTGTTGGGAAGGGCGATCGGTGCGGGC
AtCOP1  ------------------------------------------------------------

ZmCOP1  CTCTTCGCTATTACGCCAGCTGGCGAAAGGGGATGTGCTGCAAGGCGATTAAGTTGGGT
AtCOP1  ------------------------------------------------------------

ZmCOP1  AACGCCAGGGTTTTCCCAGTCACGACGTTGTAAAACGACGGCCAGTGAATTGTAATACGA
AtCOP1  -----------------------------------------------------\------

ZmCOP1  CTCACTATAGGGCGAATTGGGCCCTCTAGATGCATGCTCGAGCGGCCGCCAGTGTGATGG
AtCOP1  ------------------------------------------------------------

ZmCOP1  ATATCTGCAGAATTCGCCCTTCTGCGCCATGGGCGACTCCTCGGTGGCCGGCGCGCTCGT
AtCOP1  -------CAAAA-----ACCAAAATCACAATCGAAGAAATCTT--TTGAAAGCAAAATGGA

ZmCOP1  GCCGTCTGTGCCCAAGCCGGAGCCCGCGCCGTCCGGTGACACCTCCGCGGCGGCCGCGGC
AtCOP1  AGAGATTTCGACGGATCCGGTT---GTTCCAGC-GGTGAAACCTGACCCGAGA-----AC

ZmCOP1  GACTACAGCGGCGCTGGCGATGCCGGAGGAGGCGGGTATGCGCGCGGCGTCGGCGTCGCC
AtCOP1  ATCTTCAGTTGG--TGAAGGTGCTAATCGTCATGAAAATGACGACGGAGGAAGCGGCGGT

ZmCOP1  TCAGGGGCCTGCGGAGGAGGGGAGGGCCCCGCCGATAGGGACCTTCTCTGCCCGATCTG
AtCOP1  TCTGAGATT---GGAGCACCGGATCTG----G---ATAAAGACTTGCTTTGTCCGATTTG

ZmCOP1  CATGGCCGTCATCAAGGACGCCTTCCTCACCGCATGCGGCCACAGCTTCTGCTACATGTG
AtCOP1  TATGCAGATTATTAAAGATGCTTTCCTCACGGCTTGTGGTCATAGTTTCTGCTATATGTG

ZmCOP1  CATCGTCACGCATCTCAGCAACAAGAGCGACTGCCCCTGCTGCGGCCACTACCTTACCAA
AtCOP1  TATCATCACACATCTTAGGAACAAGAGTGATTGTCCCTGTTGTAGCCAACACCTCACCAA

ZmCOP1  GGCCCAGCTCTACCCCAACTTTCTCCTTGACAAGGTTCTGAAGAAAATATCAGCCCAACA
AtCOP1  TAATCAGCTTTACCCTAATTTCTTGCTCGATAAGCTATTGAAGAAAACTTCAGCTCGGCA

ZmCOP1  AATAGCAAAAACAGCATCGCCGATCGATCAATTTCGATGTGCATTGCAACAGGGAAATGA
AtCOP1  TGTGTCAAAAACTGCATCGCCCTTGGATCAGTTTCGGGAAGCACTACAAAGGGGTTGTGA

ZmCOP1  AATGGGGGTTAAAGAGTTGGATAGCCTTATGACTTTGATTGCTGAGAAGAAGCGGCAAAT
AtCOP1  TGTGTCAATTAAGGAGGTTGATAATCTTCTGACACTTCTTGCGGAAAGGAAGAGAAAAAT

ZmCOP1  GGAACAACAAGAATCAGAGACAAATATGCAAATATTGCTAGTCTTCTTACACTGCCTTAG
AtCOP1  GGAACAGGAAGAAGCTGAGAGGAACATGCAGATACTTTTGGACTTTTTGCATTGTCTAAG

ZmCOP1  AAAGCAAAAGCTAGAAGAGTTGAATGAGATTCAAACTGATCTACAATACATCAAAGAGGA
AtCOP1  GAAGCAAAAAGTTGATGAACTAAATGAGGTGCAAACTGATCTCCAGTATATTAAAGAAGA

ZmCOP1  TATAAGTTCTGTGGAGAGACATAGGGCAGAATTATATCGCACAAAAGAAAGGTACTCCAT
AtCOP1  TATAAATGCCGTTGAGAGACATAGAATAGATTTATACCGAGCTAGGGACAGATATTCTGT

ZmCOP1  GAAGCTGCGCATGCTTTTAGATGAGCCTACTGCGCAAAAAATG--TGGCCCTCTCCTATA
AtCOP1  AAAGTTGCGGATGCTCGGAGATGATCCAA--GCACAAGAAATGCATGGCCACATGAGA-A

ZmCOP1  GACAAAGCTAGCTGTCGCTTTCTTCCCAACTCTCGGACACCACTTAGTGGATCATGTCCA
AtCOP1  GAACCAGATTGGTTTCAACT----CC-AATTCTCTCAGCATAAGAGGAGGAAATTTTGTA

ZmCOP1  GGAACTTTACAGAATAAGAAGCTTGATTTGAAAGCTCAAGTAAGCCATCAAGGATTTCAA
AtCOP1  GGCAATTATCAAAACAAAAAGGTAGAGGGGAAGGCACAAGGAAGCTCTCATGGGCTACCA
```

Figure 1A

```
ZmCOP1  AGGAGAGATGCTCTAACTTCTTCTGATCCTCCTAACTCCCCTATACAATCGGGTAATGTT
AtCOP1  AAGAAGGATGCGCTGAGTGGGTCAGATTCGCAAAGTTT---GAATCAGTCAACTGTCTCA

ZmCOP1  ATTGCTAGGAAGAGGCGAGTTCAAGCACAGTTCAATGAGCTTCAAGAATACTACCTGCAA
AtCOP1  ATTGCTAGAAAGAAACGGATTCATGCTCAGTTCAATGATTTACAAGAATGTTACCTCCAA

ZmCOP1  AGACGTCGT-ACTGG--AGCACAGGCACGCAGACAGGAAGAAAGAGATATAGTTGCAATG
AtCOP1  AAGCGGCGTCAGTTGGCAGACCAACCAAATAGTAAACAAGAAAATGATAAGAGTGTAGTA

ZmCOP1  AATAGAGAAGGCTATCATGCAGGTCTTCAGGATTTCCAGTCTGTGCTAACAACGTTCACT
AtCOP1  CGGAGGGAAGGCTATAGCAACGGCCTTGCAGATTTTCAATCTGTGTTGACTACCTTCACT

ZmCOP1  CGATACAGTCGTCTACGTGTCATTGCGGAACTAAGACATGGAGACTTGTTTCACTCTGCC
AtCOP1  CGCTACAGTCGTCTAAGAGTTATAGCAGAAATCCGGCATGGGGATATATTTCATTCAGCC

ZmCOP1  AATATTGTATCCAGTATTGAATTTGATCGTGATGATGAACTATTTGCTACCGCTGGAGTC
AtCOP1  AACATTGTATCAAGCATAGAGTTTGATCGTGATGATGAGCTGTTTGCCACTGCTGGTGTT

ZmCOP1  TCGAAACGTATTAAAGTCTTCGAATTTTCCACTGTTGTTAATGAACCATCAGATGTGCAT
AtCOP1  TCTAGATGTATAAAGGTTTTTGACTTCTCTTCGTTTGTAAATGAACCAGCAGATATGCAG

ZmCOP1  TGCCCAGTTGTTGAAATGGCTACCAGATCTAAACTTAGCTGCCTAAGCTGGAACAAGTAC
AtCOP1  TGTCCGATTGTGGAGATGTCAACTCGGTCTAAACTTAGTTGCTTGAGTTGGAATAAGCAT

ZmCOP1  TCAAAAATATTATTGCAAGCAGTGACTATGAGGGTATAGTAACTGTGTGGGATGTTCAG
AtCOP1  GAAAAAAATCACATAGCAAGCAGTGATTATGAAGGAATAGTAACAGTGTGGGATGTAACT

ZmCOP1  ACCCGTCAGAGTGTGATGGAATATGAAGAGCATGAGAAGAGAGCATGGAGTGTTGATTTT
AtCOP1  ACTAGGCAGAGTCGGATGGAGTATGAAGAGCACGAAAAACGTGCCTGGAGTGTTGACTTT

ZmCOP1  TCTCGCACAGACTCTTCAATGCTAGTATCTGGGAGTGATGATTGCAAGGTGAAAGTGTGG
AtCOP1  TCACGAACAGAACCATCAATGCTTGTATCTGGTAGTGACGACTGCAAGGTTAAAGTTTGG

ZmCOP1  TGCACAAATCAAGAAGCAAGTGTGATCAATATTGATATGAAAGCAAATATTTGCTCGGTT
AtCOP1  TGCACGAGGCAGGAAGCAAGTGTGATTAATATTGATATGAAAGCAAACATATGTTGTGTC

ZmCOP1  AAATATAATCCTGGATCAAGCTTCTACGTTGCAGTCGGATCTGCTGATCACCATATTCAT
AtCOP1  AAGTACAATCCTGGCTCAAGCAACTACATTGCGGTCGGATCAGCTGATCATCACATCCAT

ZmCOP1  TACTTTGATTTACGTAATCCAAGTTCGCCTGTCCATATTTTCGGGGGGCACAAGAAAGCA
AtCOP1  TATTACGATCTAAGAAACATAAGCCAACCACTTCATGTCTTCAGTGGACACAAGAAAGCA

ZmCOP1  GTATCATATGTGAAATTCTTATCTAACAATGAGCTTGCGTCTGCATCAACAGATAGCACA
AtCOP1  GTTTCCTATGTTAAATTTTGTCCAACAACGAGCTCGCTTCTGCGTCCACAGATAGCACA

ZmCOP1  TTACGCTTATGGGATGTCAAGGATAACTGCCCGGTACGGACATTCAGAGGACACAAAAAT
AtCOP1  CTACGCTTATGGGATGTCAAAGACAACTTGCCAGTTCGAACATTCAGAGGACATACTAAC

ZmCOP1  GAAAAGAACTTTGTTGGCTTGTCTGTGAACAATGAATATATTGCTTGTGGAAGTGAGACA
AtCOP1  GAGAAGAACTTTGTGGGTCTCACAGTGAACAGCGAGTATCTCGCCTGTGGAAGCGAGACA

ZmCOP1  AATGAGGTTTTTGTTTATCACAAGGCTATCTCGAAACCGGCAGCAAGCCATAGATTTGTA
AtCOP1  AACGAAGTATATGTATATCACAAGGAAATCACGAGACCCGTGACATCGCACAGATTTGGA

ZmCOP1  TCTTCTGACCCGGATGATGCCGATGATGATCCTGGTTCTTATTTCATTAGTGCTGTCTGC
AtCOP1  TCGCCAGACATGGACGATGCAGAGGAAGAGGCAGGTTCCTACTTTATTAGTGCGGTTTGC

ZmCOP1  TGGAAGAGTGATAGCCCTACGATGTTAACTGCTAACAGTCAGGGGACCATAAAAGTTCTT
AtCOP1  TGGAAGAGTGATAGTCCCACGATGTTGACTGCGAATAGTCAAGGAACCATCAAAGTTCTG
```

Figure 1B

```
ZmCOP1    GTACTTGCTCCTTGATGTTATGGAGGGCGTTCAAGAGGT-TCACAGTACTGTC---CAGT
AtCOP1    GTACTCGCTGCGTGATTCTA-GTAGACATTACAAAAGATCTTATAGCTTCGTGAATCAAT

ZmCOP1    TG--------TTTCCTTTCGTGTCATTATATTCCCCCAAAATTGGGAACGGGGGCA---T
AtCOP1    AAAAACAAATTTGCCGTCTATGTTCTTTAGTGGGAGTTACATATAGAGAGAACAATTT

ZmCOP1    AATTGATCTCCGGTTAG------GGAATGAAGTTTTGCAGATGGTCAGCTGACGTAG---
AtCOP1    ATTAAAAGTAGGGTTCATCATTTGGAAAGCAACTTTGTAT-TATTATGCTTGCCTTGGAA

ZmCOP1    ------------------------------------------------------------
AtCOP1    CACTCCTCAAGAAGAATTTGTATCAGTGATGTAGATATGTCTTACGGTTTCTTAGCTTCT

ZmCOP1    ---------------------------------------
AtCOP1    ACTTTATATAATTAAATGTTAGAATCAAAAAAAAAAAA
```

Figure 1C

```
OsCOP1    ------------------------------------------------------------
ZmCOP1    ACTTTATGTGACAGCAGACGTGCACTGGCCAGGGGGATCACCATCCGTCGCCCCGGGTGT

OsCOP1    ------------------------------------------------------------
ZmCOP1    CAATAATATCACTCTGTACATCCACAAACAGACGATACGGCTCTCTCTTTTATAGGTGTA

OsCOP1    ------------------------------------------------------------
ZmCOP1    AACCTTAAACTGCCGTACGTATAGGCTGCGCAACTGTTGGGAAGGGCGATCGGTGCGGGC

OsCOP1    ------------------------------------------------------------
ZmCOP1    CTCTTCGCTATTACGCCAGCTGGCGAAAGGGGGATGTGCTGCAAGGCGATTAAGTTGGGT

OsCOP1    ------------------------------------------------------------
ZmCOP1    AACGCCAGGGTTTTCCCAGTCACGACGTTGTAAAACGACGGCCAGTGAATTGTAATACGA

OsCOP1    -----------TTATTCACGCCCAGTCGCCGCCTCCACC-GCCGCCGCCTGCTCGACTC
ZmCOP1    CTCACTATAGGGCGAATTGGGCCCTCTAGATGCATGCTCGAGCGGCCGCCAGTGTGATGG
                    *  *   ****   *  *   ** *  * *    **  ******  *    **

OsCOP1    ACCACCGCAGGGCGGCCTCCTCCTGCCGCATGGGTGACTCGACGGTGGCCGGCGCGCTGG
ZmCOP1    ATATCTGCAGAATT-CGCCCTTCTGCGCCATGGGCGACTCCTCGGTGGCCGCCGCGCTCG
          *   * ****     *  *** ****  ****** ***** *** ********* *

OsCOP1    TGCCATCGGTGCCGAAGCAGGAGCAGGCGCCGTCGGGGGACGCGTCCACGGCGGCGTTGG
ZmCOP1    TGCCGTCTGTGCCCAAGCCGGAGCCCGCGCCGTCCGGTGACACCTCCGCGGCGGCCGCGG
          **** ** ***** **** ***** *********  **  *** * *** ******  **

OsCOP1    CG------GTGGCGGGGGAGGGGGAGGAGGATGCGGGGGCGCGCGCCTCCGCGG------
ZmCOP1    CGACTACAGCGGCGCTGGCGATGCCGGAGGAGGCGGGTATGCGCGCGGCGTCGGCGTCGC
          **       * ****    **  *  ****** ***    ******  *   **

OsCOP1    ----GGGGCA---------ACGGGGAGGCCGCGGCCGACAGGGACCTCCTCTGCCCGATCT
ZmCOP1    CTCAGGGGCCTGCGGAGGAGGGGGAGGGCCCCGCCGATAGGGACCTTCTCTGCCCGATCT
              *****           * *******  *  ***** ******  ** ************

OsCOP1    GCATGGCCGTCATCAAGGACGCCTTCCTCACCGCCTGCGGCCACAGCTTCTGCTACATGT
ZmCOP1    GCATGGCCGTCATCAAGGACGCCTTCCTCACCGCATGCGGCCACAGCTTCTGCTACATGT
          ********* **************************  ********************

OsCOP1    GCATCGTCACGCATCTCAGCCACAAGAGCGACTGCCCCTGCTGCGGCAACTACCTCACCA
ZmCOP1    GCATCGTCACGCATCTCAGCAACAAGAGCGACTGCCCCTGCTGCGGCCACTACCTTACCA
          ********************  ************************* ****** ****

OsCOP1    AGGCGCAGCTCTACCCCAACTTCCTCCTCGACAAGGTCTTGAAGAAAATGTCAGCTCGCC
ZmCOP1    AGGCCCAGCTCTACCCCAACTTTCTCCTTGACAAGGTTCTGAAGAAAATATCAGCCCAAC
          ****  **************** *****  ******   ********** ***** *  *

OsCOP1    AAATTGCGAAGACAGCATCACCGATAGACCAATTTCGATATGCACTGCAACAGGGAAACG
ZmCOP1    AAATAGCAAAAACAGCATCGCCGATCGATCAATTTCGATGTGCATTGCAACAGGGAAATG
          ****  **  ********* ***** ** ********** **** ************ *

OsCOP1    ATATGGCGGTTAAAGAACTAGATAGTCTTATGACTTTGATCGCGGAGAAGAAGCGGCATA
ZmCOP1    AAATGGGGGTTAAAGAGTTGGATAGCCTTATGACTTTGATTGCTGAGAAGAAGCGGCAAA
          * **** ********* *  ***** ************** ** ************  *
```

Figure 2A

```
OsCOP1    TGGAACAGCAAGAGTCAGAAACAAATATGCAAATATTGCTGGTCTTCTTGCATTGCCTCA
ZmCOP1    TGGAACAACAAGAATCAGAGACAAATATGCAAATATTGCTAGTCTTCTTACACTGCCTTA
          *******  ***** *****  *******************  ******** ** ***** *

OsCOP1    GAAAGCAAAAGTTGGAAGAGCTGAATGAGATTCAAACTGACCTACAGTACATCAAAGAAG
ZmCOP1    GAAAGCAAAAGCTAGAAGAGTTGAATGAGATTCAAACTGATCTACAATACATCAAAGAGG
          *********** * ****** ******************* *****  ********** *

OsCOP1    ATATAAGTGCTGTGGAGAGACATAGGTTAGAATTATATCGAACAAAAGAAAGGTACTCAA
ZmCOP1    ATATAAGTTCTGTGGAGAGACATAGGGCAGAATTATATCGCACAAAAGAAAGGTACTCCA
          ******** ***************** ************* *************** *

OsCOP1    TGAAGCTCCGCATGCTTTTGGATGAACCTGCTGCATCAAAGATGTGGCCTTCACCTATGG
ZmCOP1    TGAAGCTGCGCATGCTTTTAGATGAGCCTACTGCGCAAAAATGTGGCCCTCTCCTATAG
          ******* *********** ***** ***  **** *   **  ******** ***** *

OsCOP1    ATAAACCTAGTGGTCTCTTTCTTCCCAACTCTCGGGGACCACTTAGTACATCAAATCCAG
ZmCOP1    ACAAAGCTAGCTGTCGCTTTCTTCCCAACTCTCGGACACCACTTAGTGGATCATGTCCAG
          * *** ****  *** ******************* **********  **** *****

OsCOP1    GGGGTTTACAGAATAAGAAGCTTGACTTGAAAGGTCAAATTAGTCATCAAGGATTTCAAA
ZmCOP1    GAACTTTACAGAATAAGAAGCTTGATTTGAAAGCTCAAGTAAGCCATCAAGGATTTCAAA
          *  ********************* ******** **** * ** ***************

OsCOP1    GGAGAGATGTTCTCACTTGCTCGGATCCTCCTAGTGCCCCTATTCAATCAGGCAACGTTA
ZmCOP1    GGAGAGATGCTCTAACTTCTTCTGATCCTCCTAACTCCCCTATACAATCGGGTAATGTTA
          ********* *** **** ** ************    ******* ***** ** ****

OsCOP1    TTGCTCGGAAGAGGCGAGTTCAAGCTCAGTTTAACGAGCTTCAAGAATACTATCTTCAAA
ZmCOP1    TTGCTAGGAAGAGGCGAGTTCAAGCACAGTTCAATGAGCTTCAAGAATACTACCTGCAAA
          ***** ******************* ***** ** ***************** ** ****

OsCOP1    GACGGCGTACCGGAGCACAATCACGTAGGCTGGAGGAAAGAGACATAGTAACAATAAATA
ZmCOP1    GACGTCGTACTGGAGCACAGGCACGCAGACAGGAAGAAAGAGATATAGTTGCAATGAATA
          ****  ***** *******   **** *  * *** ******* ***** * **** ****

OsCOP1    AAGAAGGTTATCATGCAGGACTTGAGGATTTCCAGTCTGTGCTAACAACATTCACACGAT
ZmCOP1    GAGAAGGCTATCATGCAGGTCTTCAGGATTTCCAGTCTGTGCTAACAACGTTCACTCGAT
          ****** *********** *** ************************* ***** ****

OsCOP1    ATAGTCGCTTGCGTGTAATTGCGGAGCTAAGACATGGAGATCTGTTTCACTCTGCAAATA
ZmCOP1    ACAGTCGTCTACGTGTCATTGCGGAACTAAGACATGGAGACTTGTTTCACTCTGCCAATA
          * *****  * ****** ******* ************** ************** ****

OsCOP1    TCGTATCAAGTATCGAATTTGACCGTGATGATGAGCTATTTGCTACTGCTGGAGTCTCAA
ZmCOP1    TTGTATCCAGTATTGAATTTGATCGTGATGATGAACTATTTGCTACCGCTGGAGTCTCGA
          * ***** ***** ******** ************ ********** ********** *

OsCOP1    AGCGCATCAAAGTCTTCGAGTTTTCTACAGTTGTTAATGAACCATCAGATGTGCATTGTC
ZmCOP1    AACGTATTAAAGTCTTCGAATTTTCCACTGTTGTTAATGAACCATCAGATGTGCATTGCC
          * ** ** *********** ***** ** **************************** *

OsCOP1    CAGTTGTTGAAATGGCTACTAGATCTAAACTCAGCTGCCTTAGCTGGAACAAGTACTCAA
ZmCOP1    CAGTTGTTGAAATGGCTACCAGATCTAAACTTAGCTGCCTAAGCTGGAACAAGTACTCAA
          ******************* ***********  ******* *******************

OsCOP1    AAAATGTTATAGCAAGCAGCGACTATGAGGGTATAGTAACTCTTTGGGATGTCCAAACCC
ZmCOP1    AAAATATTATTGCAAGCAGTGACTATGAGGGTATAGTAACTGTGTGGGATGTTCAGACCC
          ***** **** ******** ********************* * ******* ** ****
```

Figure 2B

```
OsCOP1    GCCAGAGTGTGATGGAGTATGAAGAACATGAAAAGAGAGCATGGAGTGTTGATTTTTCTC
ZmCOP1    GTCAGAGTGTGATGGAATATGAAGAGCATGAGAAGAGAGCATGGAGTGTTGATTTTTCTC
          * ************** ******* ***** ****************************

OsCOP1    GAACAGAACCCTCGATGCTAGTATCTGGGAGTGATGATTGCAAGGTCAAAGTGTGGTGCA
ZmCOP1    GCACAGACTCTTCAATGCTAGTATCTGGGAGTGATGATTGCAAGGTGAAAGTGTGGTGCA
          * *****  * ** *********************************  ***********

OsCOP1    CAAAGCAAGAAGCAAGTGCCATCAATATTGATATGAAGGCCAATATTTGCTCTGTCAAAT
ZmCOP1    CAAATCAAGAAGCAAGTGTGATCAATATTGATATGAAAGCAAATATTTGCTCGGTTAAAT
          **** ************* * **************** ** ********** ** ****

OsCOP1    ATAATCCTGGGTCGAGCCACTATGTTGCAGTGGGTTCTGCTGATCACCATATTCATTATT
ZmCOP1    ATAATCCTGGATCAAGCTTCTACGTTGCAGTCGGATCTGCTGATCACCATATTCATTACT
          **********  * ***  ** *******  ** * *********************** *

OsCOP1    TTGATTTGCGAAATCCAAGTGCGCCTGTCCATGTTTTTGGTGGGCACAAGAAAGCTGTTT
ZmCOP1    TTGATTTACGTAATCCAAGTTCGCCTGTCCATATTTTCGGGGGGCACAAGAAAGCAGTAT
          ******* ** ********* ***********  **** ** **************** **  *

OsCOP1    CTTATGTGAAGTTCCTGTCCACCAATGAGCTTGCGTCTGCATCAACTGATAGCACATTAC
ZmCOP1    CATATGTGAAATTCTTATCTAACAATGAGCTTGCGTCTGCATCAACAGATAGCACATTAC
          * *******  ***  *  *  ** ***********************  *************

OsCOP1    GGTTATGGGATGTCAAAGAAAATTGCCCTGTAAGGACATTCAGAGGGCACAAGAATGAAA
ZmCOP1    GCTTATGGGATGTCAAGGATAACTGCCCGGTACGGACATTCAGAGGACACAAAAATGAAA
          * **************  ** **  *****  ** ***********  *****  ******

OsCOP1    AGAACTTTGTTGGGCTGTCTGTAAATAACGAGTACATTGCCTGCGGGAGTGAAACGAATG
ZmCOP1    AGAACTTTGTTGGCTTGTCTGTGAACAATGAATATATTGCTTGTGGAAGTGAGACAAATG
          ************* *  ****** **  **  **  *****  **  ** *****  ** ****

OsCOP1    AGGTTTTTGTTTACCACAAGGCTATCTCAAAACCTGCTGCCAACCACAGATTTGTATCAT
ZmCOP1    AGGTTTTTGTTTATCACAAGGCTATCTCGAAACCGGCTGCCAAGCCATAGATTTGTATCTT
          *************  ************* ***** ********  *   ***********  *

OsCOP1    CTGATCTCGATGATGCAGATGATGATCCTGGCTCTTATTTTATTAGCGCAGTCTGCTGGA
ZmCOP1    CTGACCCGGATGATGCCGATGATGATCCTGGTTCTTATTTCATTAGTGCTGTCTGCTGGA
          ****  * ******** ************** *******  ***** ** **********

OsCOP1    AGAGCGATAGCCCTACCATGTTAACTGCTAACAGTCAGGGCACCATTAAAGTTCTTGTAC
ZmCOP1    AGAGTGATAGCCCTACGATGTTAACTGCTAACAGTCAGGGGACCATAAAAGTTCTTGTAC
          ****  ********** *********************** *****  ************

OsCOP1    TTGCTCCTTGATGAAATCAGTGGTTTTCATGAGATCCCTAGATAGCTTGTATATTTGATG
ZmCOP1    TTGCTCCTTGATGTTATGGAGGGCGTTCAAGAGGTTCACAG-TA----C-----------
          *************  **   ** * *** * **    * **  **

OsCOP1    TATACAGTTGTTTCCTTTTCGTGCCATTATA---CCCCAAA--TGGGAGTGGACGTATTA
ZmCOP1    TGTCCAGTTGTTTCCTTT-CGTGTCATTATATTCCCCCAAAAATTGGGAACGGGGGCATAA
          *  * ***************  ****  *******  ********  *****  ** ** ** *

OsCOP1    CTGATCTCCAACATAGGGCGCAAAGTTTTGAAGGTAATCAGCTGACATAGGGTTTCGAGG
ZmCOP1    TTGATCTCCGGT-TAGGGAATGAAGTTTTGCAGATGGTCAGCTGACGTAG----------
          *******  *****     *********  **   ***********  ***
```

Figure 2C

```
OsCOP1      GCTCGAAATGTGCATAGTCCAGAATTCTCATGTATAGGTTTAAAGCAGTCAAGTAATTGA
ZmCOP1      ------------------------------------------------------------

OsCOP1      TTATACATATGTAACGTGAGAATTGAGAAATGAACATCAAATAAGCTTGTTTGGTTGCAT
ZmCOP1      ------------------------------------------------------------

OsCOP1      AAAAAAAAAAAAAAAA
ZmCOP1      ----------------
```

Figure 2D

```
            1                                                   51
OsCOP1  --------MG STV.G.LVPSVPKQEQ.PSG .AST . L.. .V.GEGEE .AG.RAS.GG......NGE..
ZmCOP1  --------MG SSV.G.LVPSVPKPEP.PSG .TS.. ./TT..L .MPEE.GMR..S .SPQGP.EEGEGP.
InCOP1  MGEREGECEGESSMVG.VVP.VK.R......:.EEPSISH.....R.E.TPSGME......PE.....L
LeCOP1  ---------MVESSVGGVVP..VKGEVMRRMG KEEGGSVTL.....R EEVGTVTE......WE.....L
AtCOP1  ---------MEEIST PVVP...VKP PRTSSVGEG.NRHE.....N. GGSGGSEIG.P... .....L
PsCOP1  ----------MEEHSVGPLVP. V VKPEP.........SK.T.....ST TT..GTPLLVPTMS :.....L
MmCOP1  ----------------VSGS.S.GG..VS .GQSRLSC.. RPS.GVGGSSSSLGSSSRKRPLLVPLC.GLL.SYE

101
OsCOP1  R... LLCP:CM .VIK .AFLT .CGHSFCYMC:VTHLSHKS CPCCGNYL:K. .QLYPNFLL .KVLKKMS.
ZmCOP1  R... LLCP:CM .VIK ..FLT.CGHSFCYMC:VTHLSNKS CPCCGHYLTK. .QLYPNFLL KVLKKIS.
InCOP1  R.. ELLCP:CMQ:IK .AFLTSCGHSFCYMC:VTHLH.KS CPCCSHYLTT..QLYP.FLL KLLKKTS.
LeCOP1  R.. ELLCP:CMQ:IK .AFLT.CGHSFCYMC:VTHLH.KS CPCCSHYLTT.SQLYPNFLL KLLKKTS.
AtCOP1  K.. LLCP:CMQ:IK .AFLT.CGHSFCYMC::PHLR.KS CPCCSQHLTN .MQLYPNFLL KLLKKTS.
PsCOP1  K.. FLCP:CMQ:IK ..LT .CGHSFCYMC::THLR.KS CPCCGHYLT. SNLFPNFLL KLLRKTS
MmCOP1  KSN FVCP:CF MIEEAYMTKCGHSFCYKCIHQSLE .NRCPKC.YVV .NI HLYPNFLV.ELILKQKQ 151                                                 201
OsCOP1  R......QI.KT .SP:.QPRY.LQQ...G..........M .VKEL SLMTLI .EKKRHMEQQESET.MQILLVFL
ZmCOP1  Q......QI.KT. SP: QPRC.LQQ...G.E...MGVKEL SLMTLI..EKKRQMEQQESET.MQILLVFL
InCOP1  H......QTSKT. SPVEQ:RHSIEQ...GRE...VSIKEL VLLTIL.EKKRKLEQEE..ER.MQILLEFL
LeCOP1  R......QISKT..SPVEQFRHSLEQ...GSE...VSIKEL .ALLML SEKKRKLEQEE.ER.MQILL .TL
AtCOP1  R......HVSKT..SPL QFRE.LQR...GC....VSIKEV NLLTLL.AERKRKMEQEE .ER.MQILL :EL
PsCOP1  R......QISKT..SPVEHFRQ/.VQK...GCE...VTMKEL TLLLLL:EKKRKMEQEE ER.MQILL .FL
MmCOP1  RPEEKRFKL HSVSST.GHRWQIFQ LLGT .Q .NL .L.NVNLMLELLVQKKKQLE.ESH. QLQILMEFL

251
OsCOP1  HCLRKQKLEELNE:QT LQYIKE .IS--VERHRLELYRTKERYSMKLRMLL EP. .SKMWPSPM KPSGL.
ZmCOP1  HCLRKQKLEEL.E:QT LQYIKE ISSVERHR.ELYRTKERYSMKLRMLL :EPT--QKMWPSPI .K SCR:
InCOP1  HMLKKKKV .ELNEVQN LQYIKE I.-VERHRI :LYR.R RYSMKLRML .  .PLGSKSRSSSV R.T.GL
LeCOP1
        QMLRKQKV ELNEVQH LQY:KE L.SVERHR: :LYR.R RYSMKLRML .  PIGKKPWSSS: RN.GGL
AtCOP1  HCLRKQKV :ELNEVQT LQYIKE I.-VERHRI LYR.R RYSVKLRMLG .P.STR. WPH.EK.QIG?
PsCOP1  HCLRKQKV ELKEVQ: LQ-.IKE-.IG -VEKHRM LYR.R. RYSVKLRML :SG .GRKSRHSSM L.SSGL
MmCOP1  KV.RR.KREQLEQ.QKELSVLEE IKRVEE.MSGLYSPVSE .STVPQ:E. PSP....SHSS:I ......

301
OsCOP1  LPNSRGPLSTS.PGGLQNKKL LKGQIS..HQGFQRR VLTCS PPS.P.....IQSGNVI.RKRRVQ.Q
ZmCOP1  LPNSRTPLSGSCPGTLQ.KKL .LK.-QVS..HQGFQRR .ALTSS PP.SP.....IQSGNVI.RKRRVQ..Q
InCOP1  FPSSRS.HGGL.SGNLMYKK. G........GSQRK VSVTELSL.GS .SQHMNQSGL. VMRKKRVH.Q
LeCOP1  :STSQ..PGGLPTGNLTVKKV SK. QISSP...GPQRK TSISEL......NSQHMSQSGLAVVRKKRV..Q
AtCOP1  NSNSLSIRGGNPVGNYQ.KKVEGK .QGSS..HGLPKK .......ALSGS .SQSLNQSTVSM.RKKRIH.Q
PsCOP1  .SSPL.LRGGLSSGSH. TKK. GKSQISSHGHG:QRR .......PITGS SQY:NQSGL.LVRKKRVHTQ
MmCOP1  .STEYSQPPG..SGTSQ:KK..................QPWY.STL. .SRRKRLT.-H 351                                                 401
OsCOP1  F.ELQEYYLQRRRTG.\..QSRRLEER. IVTI.KEGYH .GLE .FQSVLTT:TRYSRLRV:.ELRH.G L:HS
ZmCOP1  FNELQEYYLQRRRTG.. .Q -RRQEER  IV.M.REGYH. GLQ  FQSVLTT:TRYSRLRV:.ELRH.G .L:HS
InCOP1  F..LQECYLQKRRQL..NQLQNKEER..Q.VTRREGYS..GLSEFQSVLST:TRYSRLRV: ELRH.G.:I:HS
LeCOP1  FN :LQECYLQKRRQL .NKSRVKEEK..  VVQREGYSEGL . :QSVLST:TRYSRLRV:.ELRH.G. L:HS
AtCOP1  F..LQECYLQKRRQL..QP.SKQE.::KSVVRREGYS.GL. :FQSVLT::TRYSRLRV: EIRH.G.:I:HS
PsCOP1  FN .LQECYLQKRRQ . KPHGQQER. T.F:SREGYSCGL  FQSVLT::TRYSRLRV:.EIRH.G. I:HS
MmCOP1  FE .LEQCY:STRMSRIS.:.......L SRT. SQ......L EFQECLSK:TRY.SVRPL .TLSY.S .LY.G
```

Figure 3A

```
                451
OsCOP1  ANIVSSIEF R   ELFATAGVSKRIKVFEFSTVVNEPS VHCPVVEMATRSKLSCLSWNKYSKNVIASS
ZmCOP1  ANIVSSIEF R   ELFATAGVSKRIKVFEFSTVVNEPS VHCPVVEMATRSKLSCLSWNKYSKNIIASS
InCOP1  ANIVSSIEF R   ELFATAGVSRRIKVF FSSVVNEP   AHCPVVEMSTRSKLSCLSWNKYTKNHIASS
LeCOP1  ANIVSSIEF R Y ELFATAGVSRRIKVF FSSVVNEPA  AHCPVVEMSTRSKLSCLSWNKYTKKHIASSL
AtCOP1  ANIVSIEFLR   ELFATAGVSRCIKVF FSSVVNEPALMQCP IVEMSTRSKLSCLSWNKHEKNHIASS
PsCOP1  ANIVSSIEF R   LFATAGVSRRIKVF FSAVVNEPT AHCPVVEMTTRSKLSCLSWNKY KKQIASS
MmCOP1  SSIVSSIEFDR C  YFAIAGVTKKIKVYEYGTVIQ AVI IHYPENEMTCNSKISCISWSSYHKNLLASS 501                            551
OsCOP1  YEGIVTVW VQTRQSVMEYEEHEKRAWSV FSRTEPSMLVSGS  CKVKVWCTKQEASAINI MKANICS
ZmCOP1  YEGIVTVW VQTRQSVMEYEEHEKRAWSV FSRT SSMLVSGS  CKVKVWCTNQEASVINI MKANICS
InCOP1  Y GIVTVW VTTRQSVMEYEEHEKRAWSV FSRT PSMLVSGS  CKVKVWCTKQEAS LNI MKANICC
LeCOP1  Y GIVTVW VTTRQSVMEYEEHEKR WSV FSRTEPSMLVSGS  CKVKVWCTKQE SVLNI MKANICC
AtCOP1  YEGIVTVW VTTRQSLMEYEEHEKRAWSV FSRTEPSMLVSGS  CKVKVWCTRQEASVINI MKAN CC
PsCOP1  YEGIVTVWTMTTRKSLMEYEEHEKR WSV FSRT PSMLVSGS  CKVKVWCTNQE SVLNI MK NICC
MmCOP1  YEGTVILW G TGQRSKVYQEHEKRCWSV FNLM PKLL SGS  AKVKLWSTNL NSV SIEAKANVCC

601
OsCOP1  VKYNPGSSHYVAVGSA HHIHYF LRNPS PVHVFGGHKKAVSYVKFLSTNELASAST STLRLW VKEA
ZmCOP1  VKYNPGSSFYVAVGS  HHIHYF LRNPSSPVHIFGGHKKAVSYVKFLSNMELASAST STLRLW VK
InCOP1  VKYNPGSS HVAVGSA HHIHYY LRNTSAPLHIFSGHKKAVSYVKFLSSHEL ASTI STLRLW VK
LeCOP1  VKYNPGSSVHI VGSA HHIHYY LRNTSQPVHIFSGHRKAVSYVKFLSNMELASAST STLRLW VK
AtCOP1  VKYNPGSSNYIAVGSA HHIHYY LRNISQPLHVFSGHKK VSYVKFLSNNEL S ST STLRLW VK
PsCOP1  VKY PGSGNYIAVGSA HHIHYY LRNISRPVHVFTGHKKAVSYVKFLSN ELAS ST STLRLW VKQN
MmCOP1  VKFSPSSRYHL FGCA HCVHYY LRNTKQPIMVFKGHRK VSY  KFVSGEEIVSAST SQLKLW VGKP

651
OsCOP1  CPVRTFRGHKNEKNFVGLSVNNEYIACGSETKEVIVYHK ISKPA NHRFVS....S L     PGSYF
ZmCOP1  CPVRTFRGHKNEKNFVGLSVM EYIACGSETKEVFVYHK ISKP  SHRFVS....S P      PGSYF
InCOP1  SPVRVFRGHTNEKNFVGLSVSNEP ISCGSETKEV VYHK ISKPVIWHRFGS....P V E  E VTSFF
LeCOP1  LPVRTLRGHTNEKAFVGLSV AE LSCGSETKEV VYHK ISKPV WHRFGS....P I E  E  GSYF
AtCOP1  LPVRT RGHCNEKNFVGLTVNSEYL CGSETKEVYVYHKE TRPVTSHRFGS....P M  EEE GSYF
PsCOP1  LPVRT RGH NEKNFVGLTVRSEYIACGSETKEV VYHKEISKPLCWHRFGT....L ME  E E GSYF
MmCOP1  YCLRSFKGHINEKNFVGL SNG YI ACGSENKSLYLYYKGLSKILLTFKI TVKSVL K RKE   TNE F 701                 733
OsCOP1  ISAVCWKS.... SPTMLT NSQGTIKVLVLAP
ZmCOP1  IS VCWKS.... SPTMLT NSQGTIKVLVL P
InCOP1  ISAVCWKS.... SPTML ANSQGTIKVLVL
LeCOP1  ISAVCWKS.... SPTML  NSQGTIKVLVL A
AtCOP1  ISAVCWKS.... SPTMLTANSQGTIKVLVL
PsCOP1  IS VCWKS.... RPTILTANSQGTIKVLVL
MmCOP1  VS VCWR LS GESNVLI  NSQGTIKVLELV-
```

Figure 3B

CONSTITUTIVE PHOTOMORPHOGENESIS 1 (COP1) NUCLEIC ACID SEQUENCE FROM ZEA MAYS AND ITS USE THEREOF

CROSS REFERENCE TO RELATED APPLICATIONS

This application is a divisional of U.S. application Ser. No. 11/683,281, filed Mar. 7, 2007, now issued as U.S. Pat. No. 8,785,616, which application is a divisional of U.S. application Ser. No. 10/229,436, filed Aug. 28, 2002, now issued as U.S. Pat. No. 7,208,652, which application claims benefit of under 35 USC 119(e) of U.S. provisional application Ser. No. 60/315,593 filed Aug. 29, 2001; all of which are incorporated herein by reference.

INCORPORATION OF SEQUENCE LISTING

A paper copy of the Sequence Listing and a computer readable form of the sequence listing are provided. They contains 27 nucleotide and protein sequences and are herein incorporated by reference.

INTRODUCTION

The present invention is in the field of plant molecular biology. More specifically the present invention relates to an isolated nucleic acid molecule, a protein and fragments of the protein that the isolated nucleic acid molecule encodes. Most specifically, the present invention relates to a constitutive photomorphogenesis 1 (COP1) nucleic acid sequence from *Zea mays* that encodes a COP1 protein and fragments of the COP1 protein associated with plant photomorphogenesis. The present invention also relates to a method of using the isolated COP1 nucleic acid molecules, the COP1 proteins and fragments of the COP1 proteins for molecular manipulation of shade avoidance responses of crop plants to light for improving their density tolerance and thereafter for enhancing their yield when planted at a high population density.

BACKGROUND OF THE INVENTION

Plant growth is a highly malleable process that is strongly influenced by environmental factors, especially light. Light plays a vital role in plants' photomorphogenesis and affects almost all aspects of plant growth and development. The effects of light on plant development are especially prominent at the seedling stage. Under normal light conditions with unobstructed direct light, a plant seedling develops according to a characteristic photomorphogenic pattern, that is, it has open, expanded cotyledons and a short hypocotyl. This developmental pattern rapidly establishes the seedling as a photoautotrophic organism, and most of the plant's energy is devoted to cotyledon and leaf development while longitudinal extension growth is minimized. A seedling growing in darkness, however, will etiolate, displaying elongated hypocotyls and closed and unexpanded cotyledons. Under low light conditions where light quality and intensity are reduced by shading, obstruction or high population density, a seedling develops according to a different pattern as a shade-avoiding seedling that displays reduced cotyledon expansion relative to the seedling grown in unobstructed light, and hypocotyl extension is greatly increased. During this developmental response of the seedling to the low light conditions, the hypocotyl is elongated which couples with reduction in cotyledon and leaf expansion.

Thus, a significant problem for crop farming is created when crop plants are grown at high population density as it often results in a low light level for each individual plant. To compete for this light, plants have to re-distribute their energy and nutrition towards height extension, often called a shade avoidance response, resulting in an accelerated stem elongation and thin stems. This shade avoidance response to poor light conditions in a populated environment often results in crop yield loss. For example, in maize plants, accumulating evidence suggests that the stem elongation process itself may be linked to suppression of ear development. Corn prolificacy and ear establishment are sensitive to light intensity. High population density may cause abortion of ear development at lower nodes, even at all nodes. High density leads to most of the red and blue spectra of the sunlight being absorbed by the upper leaves, leaving the far-red light filtered or reflected to the lower canopy. The red/far-red ratio is a function of canopy density. If the density is high, the red/far-red ratio is low. This low ratio triggers the shade avoidance response, in which the plants distribute resources for stem elongation in a competition for sunlight (Quail et al, Science 268, 675-680, 1995). Reduction or elimination of the shade avoidance response has been shown to improve harvest index or yield (Maliakal et al, Critic. Rev. Plant Sci. 17, 465-539, 1999; Thiele et al, Plant Physiol. 120, 73-81, 1999; Robson et al, Nature Tech. 14, 995-998, 1996). Thus, the shade avoidance response is relevant to the harvest index, for example at high population density.

Various attempts have been made to overcome the shade avoidance problem in crop farming. Breeding efforts usually result in shorter plants and, in the case of corn, smaller tassels to save energy and nutrition for kernel development (Duvick and Cassman, Crop Sci. 39, 1622-1630, 1999; Chapman and Edmeades, Crop Sci. 39, 1315-1324, 1999). Molecular and biotechnological approaches have also been tried to identify a gene or a set of genes that manipulate the photomorphogenesis pathway in a manner modifying the plant architecture to have shorter internodes. Such a plant, when growing in a dense population, would have the ability to respond to low light environment without extending its stem, thereby minimizing the shade avoidance response and enhancing yield (see, for example, Smith, U.S. Pat. No. 5,945,579; Hershey and Keller, U.S. Pat. No. 5,268,526; Deng et al., PCT Application WO00/18940).

In recent decades, many genes or gene mutants in light-signal transduction and shade avoidance response pathways have been identified and studied (Chory, Plant Cell 9: 1225-1234, 1997; Chory et al., Cell 58: 991-999, 1989; Deng et al., Genes Dev. 5: 1172-1182, 1991; Karlin-Neumann et al., Plant Physiol. 88: 1323-1331, 1988; Lissemore and Quail, Mol. Cell Biol. 8: 4840-4850, 1988; U.S. Pat. No. 5,945,579; McNellis and Deng, Plant Cell 7: 1749-1761, 1995; Nagatani et al., Plant Physiol. 102: 269-277, 1993; Osterlund et al., Trends Cell Bio. 9: 113-118, 1999; Parks and Quail, Plant Cell 5: 39-48, 1993). Among these genes, a constitutive photomorphogenesis 1 gene (COP1) from *Arabidopsis* has been studied and demonstrated to be regulated by light during plant development in response to different light conditions (Osterlund et al., Trends Cell Bio. 9: 113-118, 1999; Deng et al., Cell 71: 791-801, 1992; McNellis et al., Plant Cell 6: 1391-1400, 1995; McNellis et al., Plant Cell 8: 1491-1503, 1996; Osterlund and Deng, Plant Journal 16 (2): 201-208, 1998; Stacey et al., Plant Cell 11: 349-363; Torii et al., EMBO 17: 5577-5587, 1998; von Arnim and Deng, Cell 79: 1035-1045; Yamamoto et al., Plant Cell 10: 1083-1094, 1998; Deng et al., PCT Application WO00/18940). The COP1 gene was initially identified through recessive loss-of-function mutations in *Arabidopsis* that display a constitutively photomorphogenic phenotype regardless of light conditions (Deng et al., Genes Dev. 5: 1172-1182, 1991). The constitutively photomorphogenic phenotype and recessive nature of cop1 mutations indicate that COP1 may act as a negative regulator, or light-inactivated repressor, of photomorphogenesis. The COP1 gene in *Arabidopsis* encodes a protein that contains three recognizable domains: a ring finger domain (zinc-binding motif), a coiled-coil domain and multiple WD-40 repeats characteristic of the B subunit of trimeric G-proteins (Deng et al., Cell 71: 791-801, 1992; PCT Application WO00/18940). These protein domains have been implicated in protein-protein interactions, and thus COP1 might interact with multiple partners via these interactive domains to regulate plant morphogenic development and the shade avoidance response. Overexpression of a full-length COP1 results in quantitative hypersuppression of photomorphogenic development (McNellis et al., Plant Cell 6: 1391-1400, 1995), which suggests that COP1 plays a role in a regulatory step in mediating the repression of photomorphogenic development (Osterlund et al., Trends Cell Bio. 9: 113-118, 1999; Deng et al., PCT Application WO 00/18940). The wild-type COP1 protein normally acts to repress the photomorphogenic pathway in darkness and light reverses this repression. COP1 appears to be a downstream light-signaling component (Deng et al., Cell 71: 791-801, 1992; PCT Application WO 00/18940). Overexpression of a fragment of COP1 in *Arabidopsis* is hypothesized to down regulate native COP1, this has also resulted in shorter stems of transgenic plants growing under low light conditions in comparison with those of wild-type plants (see, Deng et al., PCT Application WO 0018940).

Thus, the COP1 proteins in plants growing at low light conditions such as in a highly populated environment will act to repress normal photomorphogenic development of these plants and help activate shade avoidance response pathway to stimulate stem elongation. Therefore, reducing the level of functional COP1 proteins in plants might produce a phenotype typical of plants growing at high light intensity conditions even when the plants are under low light conditions. This phenotype could include well developed leaves, more chloroplasts, shorter and thicker stems.

Although some studies have been done to understand the role of COP1 proteins in plant morphogenesis and development, there is little reported effort on utilizing COP1 to deal with an unsolved, common problem in crop farming; that is the shade avoidance response of plants. Deng and his colleagues (Deng et al, PCT application WO 00/18940) disclosed an isolated COP1 nucleic acid from *Arabidopsis* and use of said COP1 Their publication was directed to improved seedling emergence characteristics and not to a solution to shade avoidance related problems in crop plants grown at high population density.

Thus, there exists a need in the field for a new and different approach to reduce or diminish the shade avoiding response of crop plants growing at high population density. There exists a need, through use of a different light transduction component, i.e., COP1 gene, to improve some of crop plants' agronomic traits such as reduced stem length and increased shade tolerance that are closely associated with crop yield.

SUMMARY OF THE INVENTION

Therefore, the present invention, in one aspect, relates to an isolated nucleic acid molecule from a maize plant (*Zea mays*) comprising a full-length nucleic acid sequence from a cDNA identified as ZmCOP1 and having the function of improving crop plants' agronomic traits that are associated with the crop yield. ZmCOP1 comprises 2230 nucleotides coding a polypeptide with 693 amino acid residues. The sequence of ZmCOP1 comprises SEQ ID NO: 12.

The present invention, in another aspect, provides an isolated nucleic acid from *Zea mays* comprising a nucleotide sequence, wherein the nucleotide sequence is defined as follows: (1) the nucleotide sequence has at least 80% sequence identity to a sequence comprising SEQ ID NO: 12; (2) the nucleotide sequence hybridizes under stringent conditions to the complement of a second isolated nucleic acid, wherein the nucleotide sequence of the second isolated nucleic acid comprising SEQ ID NO: 12; or (3) the nucleotide sequence is complementary to (1) or (2).

The present invention, in still another aspect, provides an isolated nucleic acid from *Zea mays* comprising a nucleotide sequence, wherein the nucleotide sequence is defined as follows: (1) the nucleotide sequence encodes a polypeptide having an amino acid sequence that has at least 90% sequence identity to a sequence comprising SEQ ID NO: 13; (2) the nucleotide sequence hybridizes under stringent conditions to the complement of a second isolated nucleic acid, wherein the nucleotide sequence of the second isolated nucleic acid encodes a polypeptide having an amino acid sequence comprising SEQ ID NO: 13; or (3) the nucleotide sequence is complementary to (1) or (2).

The present invention, in yet another aspect, also relates to a recombinant DNA construct for producing high-density tolerant crop plants. The construct comprises a light inducible promoter, a COP1 structural nucleic acid sequence that comprises a sequence at least 80% identical to SEQ ID NO: 12 or a fragment thereof, and a transcription terminator. The recombinant DNA construct causes reduction of the indigenous COP1 protein level upon its transformation into a crop plant through introduction of the COP1 structural nucleic acid sequence in an antisense orientation wherein an antisense COP1 mRNA is transcribed and base-paired with the indigenous COP1 mRNA. The recombinant DNA construct also causes the reduction of the indigenous COP1 protein level upon its transformation into a crop plant by overexpressing a full length or a fragment of the COP1 protein that binds to a native COP1 protein and makes the COP1 protein complex non-functional. With the reduction of the native COP1 protein level in the crop plants the density tolerance of the crop plants is improved and the crop plants may be overplanted at a high population density to achieve enhanced yield.

The light inducible promoter used in the recombinant DNA construct may be, but may not be limited to, a cab promoter, an ATHB-2 promoter, or a far-red light inducible promoter for the antisense approach or overexpression of the COP1 nucleic acid sequence or a fragment thereof.

The present invention, in yet another aspect, also relates to transgenic crop plants that demonstrate a high-density tolerant trait. These transgenic crop plants contain exogenous COP1 nucleic acid sequences that may be in an "antisense" orientation or may be overexpressed. The exogenous COP1 nucleic acid sequences are at least 80% identical to SEQ ID NO: 12 or fragments thereof. In a preferred embodiment, the crop plants contain a full-length ZmCOP1 nucleic acid sequence having SEQ ID NO: 12 or a fragment thereof. In one example of the present invention when a fragment is considered, the fragment contains about 1233 nucleotides from the 5' end of the ZmCOP1 having SEQ ID NO: 14. In another example of the present invention, the fragment contains about 906 nucleotides from the 5' end having SEQ ID NO: 16. The transgenic crop plants have reduced levels of the native COP1 proteins from their native COP1 nucleic acid sequences. The transgenic crop plants also demonstrate a number of other desirable agronomic traits over wild-type crop plants in that they have shorter stems and more sturdy architecture.

The present invention, in yet still another aspect, also provides a method of overplanting crop plants at a high population density for yield enhancement by producing the transgenic crop plants with reduced COP1 protein level in comparison to that of the wild crop plants. Through reduction of the COP1 protein levels in the transgenic crop plants the architecture of the transgenic plants is modified and their shade avoidance responses to light are minimized. In a preferred embodiment, the levels of the functional endogenous COP1 proteins in the transgenic crop plants may be reduced by binding an endogenous COP1 mRNA with an antisense ZmCOP1 sequence that comprises the full-length ZmCOP1 nucleic acid sequence of the present invention encoding SEQ ID NO: 13. The levels of the functional endogenous COP1 proteins in the transgenic plants may also be reduced by binding the endogenous COP1 mRNA with an antisense ZmCOP1 sequence that only comprises a fragment of the COP1 nucleic acid sequence. The level of the functional endogenous COP1 proteins may also be reduced by overexpressing a full length unaltered or mutated ZmCOP1 protein or a fragment thereof with binding domains that binds to a native endogenous COP1 protein and thus rendering the endogenous COP1 protein complex non-functional. The fragment of the ZmCOP1 protein used in the present invention as an example may comprise 411 amino acid residues from the N terminal end having SEQ ID NO: 15 that comprises a protein-binding domain. The fragment of the COP1 protein in another example may also comprise 301 amino acid residues from the N terminal end having SEQ ID NO: 17 that comprises a protein-binding domain.

BRIEF DESCRIPTION OF THE DRAWINGS

FIG. 1A-C. Nucleotide sequence alignment of *Arabidopsis* COP1 (AtCOP1 gi-402684) (SEQ ID NO:19) and maize (*Zea mays*) COP1 (ZmCOP1) (SEQ ID NO:18). The homology comparison indicates that these two nucleotide sequences have a 50% sequence identity.

FIG. 2A-D. Nucleotide sequence alignment of the rice (*Oryza sativa*) COP1 (OsCOP1, gi7592844) (SEQ ID NO:20) and maize (*Zea mays*) COP1 (ZmCOP1) (SEQ ID NO:18). The homology comparison indicates that these two nucleotide sequences have a 77% sequence identity.

FIG. 3A-B, Peptide sequence alignment of maize (*Zea mays*) COP1 (ZmCOP1) (SEQ ID NO:22) and selected COP1 peptide sequences from other plants. ZmCOP1 is from maize (*Zea mays*), PsCOP1 from pea (*Pisum sativum*) (SEQ ID NO:26), At COP1 from *Arabidopsis thaliana* (SEQ ID NO:25), COP1 from Japanese morning glory (*Ipomoea nil*) (SEQ ID NO:23), OsCOP1 from rice (*Oryza saliva*) (SEQ ID NO:21), MmCOP1 (*Mus musculus* (SEQ ID NO:27) and LeCOP1 from tomato (*Lycopersicon esculentum*) (SEQ ID NO:24).

DETAILED DESCRIPTION

Figure 4:
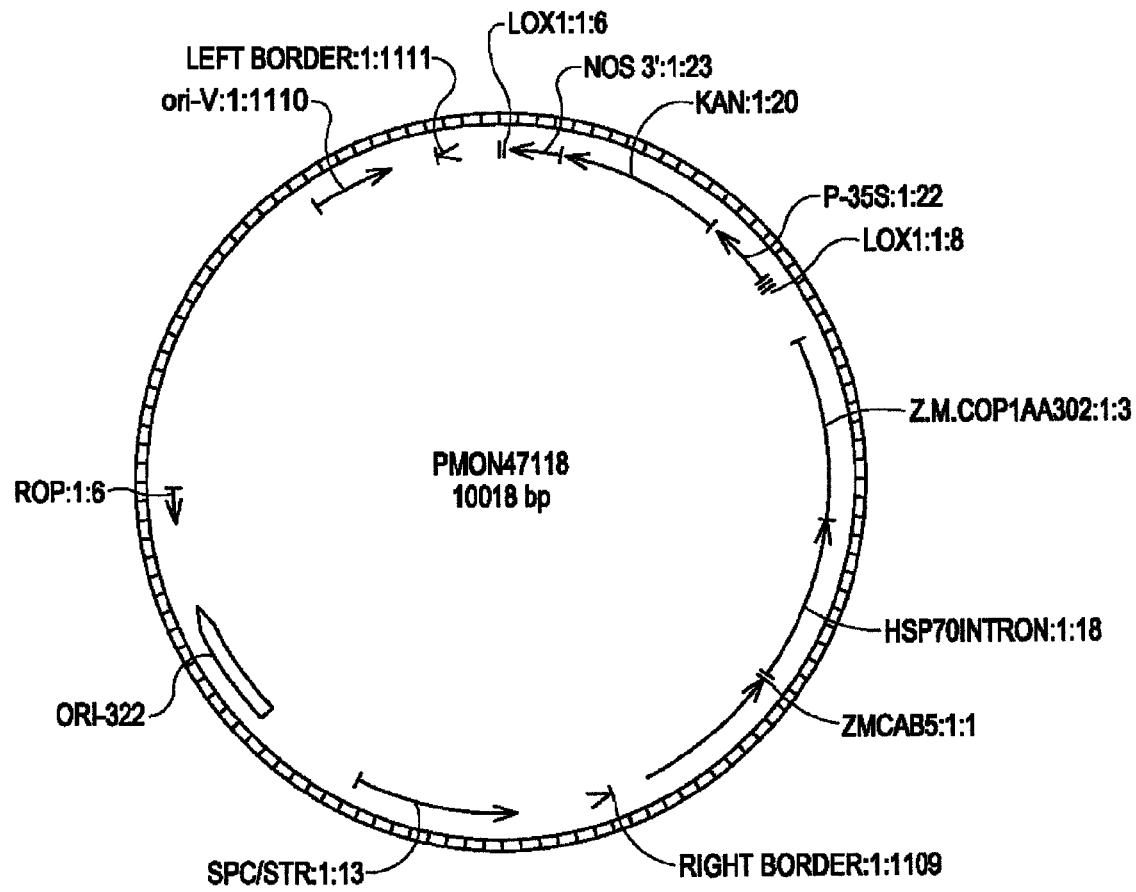
FIG. 4. A plasmid map of pMON47119. The coding sequence of the N-terminal end 411 amino acid residues of ZmCOP1 was placed under the control of a cab promoter.

Provided below are the following definitions to aid those skilled in the art in understanding the detailed description of the present invention.

As used herein, "antisense technology" refers to a method to introduce into cells a RNA or single-stranded DNA molecule that is complementary to the mRNA of the target gene. This antisense molecule may base-pair with the endogenous mRNA, preventing translation of the mRNA into a protein.

As used herein, a "coding sequence", "structural nucleotide sequence" or "structural gene" is a nucleotide sequence that is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence may include, but may not be limited to, genomic DNA, cDNA, and recombinant nucleotide sequences.

As used herein, a constitutive photomorphogenesis 1 nucleic acid, or "COP1 nucleic acid", refers to a nucleic acid encoding all or part of a specific constitutive photomorphogenesis 1 protein, or "COP1 protein". A COP1 nucleic acid may be defined functionally by its ability to confer a modulated photomorphogenic response upon transformation into a plant. The COP1 nucleic acids may include any COP1 nucleic acids from any source. The exemplary COP1 nucleic acid is the COP1 nucleic acid as disclosed in the present invention.

As used herein, a "C-terminal region" refers to the region of a peptide, polypeptide, or protein chain from the middle thereof to the end that carries the amino acid having a free carboxyl group. A "N-terminal region" refers to the region of a peptide, polypeptide, or protein chain from the amino acid having a free amino group to the middle of the chain.

As used herein, "expression" refers to the transcription and stable accumulation of sense (mRNA) or antisense RNA derived from the nucleic acid of the invention. Expression may also refer to translation of mRNA into a polypeptide. Also as used herein, "overexpression" refers to the production of a gene product in transgenic organisms that exceeds levels of production in normal or non-transformed organisms.

As used herein, a "genotype" refers to the genetic constitution, latent or expressed, of a plant, the sum total of all genes present in an individual. As used herein, a "phenotype" of a plant is any of one or more characteristics of a plant (e.g. male sterility, yield, quality improvements, etc.), as contrasted with the genotype. A change in genotype or phenotype may be transient or permanent.

As used herein, a "homolog" of a nucleotide sequence refers to an isolated nucleic acid sequence which is substantially the same as the COP1 nucleic acid sequence of the present invention or its complementary nucleotide sequence. A "homolog" of the COP1 nucleic acid sequence is a polynucleotide sequence from a plant species that encodes a polypeptide that is functionally similar to COP1 and that preferably has substantial amino acid sequence identity or similarity to COP1 from maize.

Planting or population density varies from a crop to a crop, from a growing region to another region and from a year to another year. As used herein, the term "high population density" is defined as a density at least 10% to 100% higher than the average prevailing density for a given crop in a given growing region. Preferably, the high population density is at least 10% higher, more preferably at least 40% higher, more preferably at least 70% higher, and most preferably at least 100% higher than the average prevailing density for the given crop in the given growing region. The "average prevailing density" is defined as the average of the planting density used by the majority of farmers in a region. Taken corn as an example, the average prevailing density is 20,000 plants per acre in Missouri, USA. The higher population density is preferably at least 22,000 plants per acre, more preferably at least 28,000 plants per acre, more preferably at least 34,000 plants per acre, and most preferably at least 40,000 plants per acre.

The average prevailing densities of a few crop plants in the USA in 2000 are listed below (Table 1). The exemplary crop species are just examples and, therefore, may not be construed as limitations to the scope of the present invention. Similarly, the country selected above, i.e., USA, is also an example in which the average prevailing densities of these few crop plants can be demonstrated. It may not be construed as a limitation of the present invention.

TABLE 1

The average prevailing densities of a few crop plants in the USA (per acre)

| Crop Name | Density | Crop Name | Density |
|---|---|---|---|
| Corn | 20,000-25,000 | Canola | 260,000-350,000 |
| Wheat | 1,000,000-1,500,000 | Sunflower | 17,000-23,000 |
| Rice | 650,000-900,000 | Cotton | 28,000-55,000 |
| soybean | 150,000-200,000 | | |

As used herein, "hybridization" refers to the ability of a strand of nucleic acid to join with a complementary strand via base pairing. Hybridization occurs when complementary sequences in the two nucleic acid strands bind to one another.

As used herein, "identical" nucleotide or protein sequences are determined by using programs such as a BLAST program (Altschul et al., Nucleic Acids Res. 25:3389-3402; 1997) using the default parameters (Expectation value (E): blank; Alignment view options: pairwise; Filter query sequence: no; Cost to open a gap: 0; Cost to extend a gap: 0; X dropoff value for gapped alignment: 0; Show GI's in defines: no; Penalty for a nucleotide mismatch: −3; Reward for a nucleotide match: 1; Threshold for extending hits: 0; Perform gapped alignment: yes; Query Genetic code to use: standard; DB Genetic code: standard; Believe the query define: no; Matrix: BLOSUM62; Word size: 0; Effective length of the database: 0; Query strand Use: both).

As used herein, an "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

The term "polypeptide" or "protein", as used herein, refers to a polymer composed of amino acids connected by peptide bonds. The term "polypeptide" or "protein" also applies to any amino acid polymers in which one or more amino acid residue is an artificial chemical analogue of a corresponding naturally occurring amino acid, as well as to any naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. It is well known in the art that proteins or polypeptides may undergo modification, including but not limited to, disulfide bond formation, gamma-carboxylation of glutamic acid residues, glycosylation, lipid attachment, phosphorylation, oligomerization, hydroxylation and ADP-ribosylation. Exemplary modifications are described in most basic texts, such as, for example, *Proteins—Structure and Molecular Properties,* 2nd ed. (Creighton, Freeman and Company, N.Y., 1993). Many detailed reviews are available on this subject, such as, for example, those provided by Wold (In: *Post-translational Covalent Modification of Proteins,* Johnson, Academic Press, N.Y., pp. 1-12, 1983), Seifter et al. (*Meth. Enzymol.* 182: 626, 1990) and Rattan et al. (*Ann. N.Y. Acad. Sci.* 663: 48-62, 1992). Modifications can occur anywhere in a polypeptide, including the peptide backbone, the amino acid side chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli or other cells, prior to proteolytic processing, almost invariably will be N-formylmethionine. During post-translational modification of the polypeptide, a methionine residue at the $NH_2$ terminus may be deleted. Accordingly, this invention contemplates the use of both the methionine containing and the methionine-less amino terminal variants of the protein of the invention. Thus, as used herein, the term "protein" or "polypeptide" includes any protein or polypeptide that is modified by any biological or non-biological process. The terms "amino acid" and "amino acids" refer to all naturally occurring amino acids and, unless otherwise limited, known analogs of natural amino acids that can function in a similar manner as naturally occurring amino acids.

As used herein, the term "isolated polypeptide" refers primarily to a polypeptide produced by expression of an isolated nucleic acid molecule of the present invention or by chemically synthesizing process. Alternatively, this term may refer to a polypeptide which has been sufficiently separated from other polypeptides or proteins with which it would naturally be associated, so as to exist in substantially pure form. Also as used herein, a "functionally equivalent fragment" of the isolated polypeptide refers to a polypeptide that lacks at least one residue a native full length COP1 polypeptide. Such a fragment retains COP1 activity when expressed in a transgenic plant or possesses a characteristic functional domain or an immunological determinant characteristic of a native COP1 polypeptide. Immunologically active fragments typically have a minimum size of 7 or 17 or more amino acids. Preferably, COP1 fragments are at least 10 amino acids in length.

As used herein, the term "native" refers to a naturally occurring ("wild type") nucleic acid or polypeptide.

As used herein, a "percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. The percentage of sequence identity may be determined by using programs such as a BLAST program (Altschul et al., Nucleic Acids Res. 25:3389-3402; 1997) using the default parameters.

As used herein, a "promoter" refers to a DNA sequence capable of controlling the expression of a coding sequence or functional RNA. In general, a coding sequence is located 3' to a promoter sequence. The promoter sequence consists of proximal and more distal upstream elements, the later elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". Promoters which cause conditional expression of a structural nucleotide sequence under the influence of changing environmental conditions or developmental conditions are commonly referred to as "inducible promoter".

"Promoter" refers to a DNA sequence that binds an RNA polymerase (and often other transcription factors as well) and promotes transcription of a downstream DNA sequence. Said sequence can be an RNA that has function, such as rRNA (ribosomal RNA) or tRNA (transfer RNA). Often, the RNA produced is a hetero-nuclear (hn) RNA that has introns which are spliced out to produce an mRNA (messenger RNA). A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively "Specifically" expressed and "enhanced" expression are not distinguishable and are used inter-changeably herein. Often, a promoter discussed as "specifically" expressed in one paper or patent is found to only offer "enhanced" expression in that tissue as the number of tissues studied for expression is increased, or more sensitive techniques are used to study expression in the same tissues. "Enhanced expression" is used herein to refer to any promoter that provides an increased expression in a single tissue or developmental stage, or under a particular environmental condition, but causes expression, even significant expression, in other tissue(s), or developmental stage(s), or environmental condition(s).

Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, cold, or chemicals such as ethanol, jasmonate, salicylic acid, or safeners.

Any plant promoter can be used as a 5' regulatory sequence for modulation expression of a particular gene or genes. One preferred promoter would be a plant RNA polymerase II promoter. Plant RNA polymerase II promoters, like those of other higher eukaryotes, have complex structures and are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, Ann. Rev. Biochem. 50:349-383, 1981; Messing et al., In: Genetic Engineering of Plants, Kosuge et al., eds., pp. 211-227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: Genetic Engineering of Plants, Kosuge et al., eds., pp. 211-227, 1983). In addition, virtually all promoters include additional upstream activating sequences or enhancers (Benoist and Chambon, nature 290:304-310, 1981; Gruss et al., Proc. Nat. Acad. Sci. USA 78:943-947, 1981; and Khoury and Gruss, Cell 27:313-314, 1983) extending from around 100 bp to 1,000 bp or more upstream of the transcription initiation site.

When fused to heterologous DNA sequences, such promoters typically cause the fused sequence to be transcribed in a manner that is similar to that of the gene sequence with which the promoter is normally associated. Promoter fragments that include regulatory sequences can be added (for example, fused to the 5' end of, or inserted within, an active promoter having its own partial or complete regulatory sequences (Fluhr, et al., Science 232:1106-1112, 1986; Ellis et al., EMBO J. 6:11-16, 1987; Strittmatter and Chua, Proc. Nat. Acad. Sci. USA 84:8986-8990, 1987; Poulsen and Chua, Mol. Gen. Genet. 214:16-23, 1988; Comai et al., Plant Mol. Biol. 15:373-381, 1991). Alternatively, heterologous regulatory sequences can be added to the 5' upstream region of an inactive, truncated promoter, e.g., a promoter including only the core TATA and, sometimes, the CCAAT elements (Fluhr, et al., Science 232:1106-1112, 1986; Strittmatter and Chua, Proc. Nat. Acad. Sci. USA 84:8986-8990, 1987; Aryan et al., Mol. Gen. Genet. 225:65-71, 1991).

Promoters are typically comprised of multiple distinct "cis-acting transcriptional regulatory elements," or simply "cis-elements," each of which can confer a different aspect of the overall control of gene expression (Strittmatter and Chua, Proc. Nat. Acad. Sci. USA 84:8986-8990, 1987; Ellis et al., EMBO J. 6:11-16, 1987; Benfey et al., EMBO J. 9:1677-1684, 1990). "cis elements" bind trans-acting protein factors that regulate transcription. Some cis elements bind more than one factor, and trans-acting transcription factors may interact with different affinities with more than one cis element (Johnson and McKnight, Ann. Rev. Biochem. 58:799-839, 1989). Plant transcription factors, corresponding cis elements, and analysis of their interaction are discussed, for example, in: Martin, Curr. Opinions Biotech. 7:130-138, 1996; Murai, In: Methods in Plant Biochemistry and Molecular Biology, Dashek, ed., CRC Press, 1997, pp. 397-422; and Methods in Plant Molecular Biology, Maliga et al., eds., Cold Spring Harbor Press, 1995, pp. 233-300. The promoter sequences of the present invention can contain "cis elements" which can modulate gene expression. Cis elements can be part of the promoter, or can be upstream or downstream of said promoter. Cis elements (or groups thereof) acting at a distance from a promoter are often referred to as repressors or enhancers. Enhancers act to upregulate the transcriptional initiation rate of RNA polymerase at a promoter, repressors act to decrease said rate. In some cases the same elements can be found in a promoter and an enhancer or repressor. Cis elements are generally sites where transcription factors bind to the DNA and modulate the rate at which RNA polymerase binds to the promoter.

The term "constitutive promoter" means a regulatory sequence that causes expression of a structural nucleotide sequence in most cells or tissues at most times. Constitutive promoters are active under many environmental conditions and states of development or cell differentiation. A variety of constitutive promoters are well known in the art. Examples of constitutive promoters that are active in plant cells include but are not limited to the nopaline synthase (NOS) promoters; the cauliflower mosaic virus (CaMV) 19S and 35S (sometimes called 35S herein, or a derivative of which is called e35S {U.S. Pat. Nos. 5,359,142, 5,196,525, 5,322,938, 5,164,316, and 5,424,200}); the tobacco mosaic virus promoter; the figwort mosaic virus promoters; and actin promoters, such as the *Arabidopsis* actin gene promoter (see, e.g., Huang et al., *Plant Mol. Biol.* 33:125-139 (1997).

The term "tissue-specific promoter" means a regulatory sequence that causes an enhancement of transcription from a downstream gene in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistols, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One skilled in the art will recognize that a tissue-specific promoter may drive expression of operably linked sequences in tissues other than the target tissue. Thus, as used herein a tissue-specific promoter is one that drives expression preferentially in the target tissue, but may also lead to expression in other tissues as well.

Suitable seed-specific (inclusive of seed enhanced promoters) can be derived from the following genes: MAC1 from maize (Sheridan et al., *Genetics* 142:1009-1020 (1996); Cat3 from maize (GenBank No. L05934, Abler et al., *Plant Mol. Biol.* 22:10131-1038 (1993); vivparous-1 from *Arabidopsis* (Genbank No. U93215); Atimycl from *Arabidopsis* (Urao et al., *Plant Mol. Biol.* 32:571-57 (1996); Conceicao et al., *Plant* 5:493-505 (1994), herein incorporated by reference in their entireties); napA from *Brassica napus* (GenBank No. J02798); the napin gene family from *Brassica napus* (Sjodahl et al., *Planta* 197:264-271 (1995)). Seed specific promoters are an integral part of the current invention. It should be noted that a seed specific promoter can often cause the expression of a gene in more than just seeds, or in more than one portion or tissue of a seed. Thus seed specific can be read as seed enhanced and is meant to be inclusive of any promoter that preferentially drives expression in any tissue in seed.

Promoters derived from genes encoding embryonic storage proteins, which includes the gene encoding the 2S storage protein from *Brassica napus* (Dasgupta et al, Gene 133:301-302 (1993); the 2s seed storage protein gene family from *Arabidopsis*; the gene encoding oleosin 20 kD from *Brassica napus* (GenBank No. M63985); the genes encoding oleosin A (GenBank No. U09118) and oleosin B (GenBank No. U09119) from soybean; the gene encoding oleosin from *Arabidopsis* (GenBank No. Z17657); the gene encoding oleosin 18 kD from maize (GenBank No. J05212, Lee, Plant Mol. Biol. 26:1981-1987 (1994)); and the gene encoding low molecular weight sulphur rich protein from soybean (Choi et al., Mol. Gen. Genet. 246:266-268 (1995)), can also be used.

Promoters can also be inducible under particular environmental conditions. For example a promoter could be upregulated, or even turned on, by far-red light, cold, heat, drought, blue light (or any other mix of wavelengths), day length, or myriad other environmental conditions. These promoters could be isolated by the use of general molecular biology techniques including transcription profiling of possible genes, and then isolation of the promoters of those genes through cloning and PCR.

As noted above, the present invention provides a recombinant DNA construct or expression vector that facilitates the expression of the COP1 nucleic acid sequence discussed herein in plants. As used herein, the term "recombinant DNA construct" refer to assemblies of DNA fragments through genetic engineering operatively linked in a functional manner that direct the expression of the COP1 nucleic acid sequence discussed herein, as well as any additional sequence(s) or gene(s) of interest in the plants.

As used herein, "regeneration" refers to the process of growing a plant from a plant cell or tissue (e.g., plant protoplast or explant).

As used herein, "sequence homology" refers to nucleic acid or polypeptide sequence that has certain percentage of nucleotide or amino acid similarity, as used in the present invention, to a native COP1 nucleic acid or polypeptide sequence or COP1 nucleic acid or polypeptide sequence. Ordinarily, if a COP1 nucleic acid or polypeptide sequence encompassed by the present invention has at least about 70% nucleotide or amino acid similarity to a native COP1 nucleic acid or polypeptide sequence or to a COP1 nucleic acid, preferably at least 80%, more preferably at least about 90%, and most preferably at least about 95% similarity, such sequence homology is considered to be substantial homology.

As used herein, the term "sequence identity" refers to amino acid or nucleic acid sequences that when compared using the local homology algorithm of Smith and Waterman in the BestFit program (Wisconsin Package Version 10.0, Genetics Computer Group (GCG), Madison, Wis., 1981) are exactly alike.

As used herein, the term "sequence similarity" refers to amino acid sequences that when compared using the local homology algorithm of Smith and Waterman in the BestFit program (Wisconsin Package Version 10.0, Genetics Computer Group (GCG), Madison, Wis., 1981) match when conservative amino acid substitutions are considered.

As used herein, "shade avoidance responses" refer to plants that, when growing at a high density condition or other shading environments, will compete for light by elongating their stems unlimitedly. These plants will usually be taller with thinner stems and have reduced photosynthesis rate and reduced allocation of resource to fruits.

As used herein, a "stringent condition" is functionally defined with regard to hybridization of a nucleic-acid probe to a target nucleic acid (i.e., to a particular nucleic acid sequence of interest) by the specific hybridization procedure discussed in Sambrook et al. (Molecular Cloning: A Laboratory Manual, Cold Spring Harbor Laboratory Press, Cold Spring Hobart, 1989, at 9.52-9.55). Regarding the amplification of a target nucleic acid sequence (e.g., by PCR) using a particular amplification primer pair, "stringent conditions" are conditions that permit the primer pair to hybridize substantially only to the target nucleic acid sequence to which a primer having the corresponding wild-type sequence (or its complement) would bind so as to produce a unique amplification product. For hybridization of a probe or primer to a polynucleotide of another plant species in order to identify homologs, preferred hybridization and washing conditions are as discussed in Sambrook et al. (supra, at 9.47-9.57, wherein "high stringent conditions" include hybridization at 65° C. in a hybridization solution that includes 6×SSC and washing for 1 hour at 65° C. in a wash solution that include 0.5×SSC, 0.5% SDS. "Moderate stringency" conditions are similar except that the temperature for the hybridization and washing steps are performed at a lower temperature at which the probe is specific for a target sequence, preferably at least 42° C., more preferably at least 50° C., more preferably at least 55° C., and more preferably at least 60° C.

As used herein, a "tissue sample" is any sample that comprises more than one cell. In a preferred aspect, a tissue sample comprises cells that share a common characteristic (e.g., derived from a leaf, an ear or a stem, etc.).

As used herein, a "3' untranslated region" or "3' untranslated nucleic acid sequence" refers to a piece of transcribed but untranslated nucleic acid sequence at the 3' end that functions in a plant cell to cause transcriptional termination and the addition of polyadenylate nucleotides to the 3' end of said RNA sequence. Typically, a DNA sequence located from four to a few hundred base pairs downstream of the polyadenylation site serves to terminate transcription. The region is required for efficient polyadenylation of transcribed messenger RNA (mRNA). RNA polymerase transcribes a coding DNA sequence through a site where polyadenylation occurs.

As used herein, "transformation" refers to the transfer of a nucleic acid fragment into the genome of a host organism such as a host plant, resulting in genetically stable inheritance. Host plants containing the transformed nucleic acid fragments are referred to as "transgenic plants".

Unless otherwise defined, all technical and scientific terms used herein have the same meaning as commonly understood by one of ordinary skill in the art to which this invention belongs.

Although methods and materials similar or equivalent to those described herein can be used in the practice or testing of the present invention, suitable methods and materials are described below. Standard recombinant DNA and molecular cloning techniques used herein are well known in the art and are described in detail in Sambrook et al. (Molecular Cloning: A Laboratory Manual, Cold Spring Harbor Laboratory Press, Cold Spring Harbor, 1989).

Constitutive Photomorphogenesis 1 (COP1) Gene and Protein

The present invention is directed to an isolated constitutive photomorphogenesis 1 (COP1) nucleic acid that encodes a COP1 protein. As disclosed in the present invention, the COP1 nucleic acid disclosed herein is isolated from a maize plant and is a full length COP1 cDNA sequence comprising 2230 nucleotides. Its COP1 protein comprises 693 amino acid residues.

In a preferred embodiment, an isolated nucleic acid molecule of the present invention may comprise a nucleotide sequence or complement thereof, wherein the nucleotide sequence encodes a polypeptide having an amino acid sequence that has at least 90% sequence identity to SEQ ID NO: 13.

In a further preferred embodiment, an isolated nucleic acid molecule of the present invention may comprise a nucleotide sequence or complement thereof, wherein the nucleotide sequence encodes a polypeptide having an amino acid sequence that has at least 93% sequence identity to SEQ ID NO: 13.

In a more preferred embodiment, an isolated nucleic acid molecule of the present invention may comprise a nucleotide sequence or complement thereof, wherein the nucleotide sequence encodes a polypeptide having an amino acid sequence that has at least 96% sequence identity to SEQ ID NO: 13.

In a most preferred embodiment, an isolated nucleic acid molecule of the present invention may comprise a nucleotide sequence or complement thereof, wherein the nucleotide sequence encodes a polypeptide having an amino acid sequence that has at least 98% sequence identity to SEQ ID NO: 13.

The isolated nucleic acid of the present invention may also comprise a nucleotide sequence or complement thereof, wherein the nucleotide sequence encodes a polypeptide having an amino acid sequence set forth in SEQ ID NO: 13 with conservative amino acid substitutions.

The present invention is directed to a method for manipulating COP1 gene expression in transgenic plants to overcome shade avoidance responses when they grow in a highly populated environment. For this purpose, the COP1 nucleic acid used in the present invention is not necessarily the maize COP1 nucleic acid disclosed herein. It can be any COP1 nucleic acids available in the art and these COP1 nucleic acids may include the sequences from *Arabidopsis* (Deng et al., Cell 27, 791-801, 1992), rice (gi7592844), tomato (gi4090943), pea (Zhao et al., Biochimica et Biophysica Acta-Gene Structure and Expression 1395, 326-328, 1998) and Japanese morning glory (*Ipomoea nil*). The species provided herein are just a few examples of COP1 sequences that can be readily available for use in the present invention and thus should not be interpreted in any way to limit the scope of the present invention. The COP1 nucleotide sequence used in the present invention can be a full length or a fragment of any of the COP1 nucleotide sequences from any species. Those skilled in the art will be able to identify other COP1 sequences from different species and alterations that can be made to the COP1 sequences and method disclosed herein while not departing from the scope of the present invention.

Preparation of cDNA Libraries for Isolation of COP1 Gene

Complementary DNA (cDNA) libraries from a plant may be prepared and screened for COP1 nucleic acids. Using a maize plant as an example herein and throughout the detailed descriptions of the preferred embodiments, cDNA libraries from the maize plant may be prepared according to standard techniques known to those skilled in the art, for instance, in Sambrook et al., Molecular Cloning—A Laboratory Manual, Cold Spring Harbor Laboratory, Cold Spring Harbor, N.Y., (1989). Using conventional methodologies, cDNA libraries can be constructed from the mRNA of a given tissue sample or an organ using poly dT primers and reverse transcriptase (Efstratiadis et al., Cell 7:279-288, 1976; Higuchi et al., Proc. Natl. Acad. Sci. (U.S.A.) 73:3146-3150, 1976; Maniatis et al., Cell 8:163, 1976; Land et al., Nucleic Acids Res. 9:2251-2266, 1981; Okayama et al., Mol. Cell. Biol. 2:161-170, 1982; Gubler et al., Gene 25:263, 1983). Several methods may be employed to obtain full-length cDNA constructs. For example, terminal transferase can be used to add homopolymeric tails of dC residues to the free 3' hydroxyl groups (Land, et al., Nucleic Acids Res. 9:2251-2266, 1981). This tail can then be hybridized by a poly dG oligo which can act as a primer for the synthesis of full length second strand cDNA. A simplified method has been developed by using synthetic primer-adapters that have both homopolymeric tails for priming the synthesis of the first and second strands and restriction sites for cloning into plasmids (Coleclough et al., Gene 34:305-314, 1985) and bacteriophage vectors (Krawinkel et al., Nucleic Acids Res. 14:1913, 1986; and Han et al., Nucleic Acids Res. 15: 6304, 1987).

A method to enrich preparations of mRNA is to fractionate by size. One such method is to fractionate by electrophoresis through an agarose gel (Pennica et al., Nature 301:214-221, 1983). Another such method employs sucrose gradient centrifugation in the presence of an agent, such as methylmercuric hydroxide, that denatures secondary structure in RNA (Schweinfest, et al., Proc. Natl. Acad. Sci. (U.S.A.) 79:4997-5000, 1982).

In one of the preferred embodiments, preparation of appropriately enriched cDNA libraries from tissue of interest such as a tissue sample from the stem or ear of the maize plant may be described as below. The maize plants may be grown in a greenhouse and, when they reach a desired developmental stage, they may be used for collection of the tissue samples. The cDNA library may be constructed using techniques known to those skilled in the art. Briefly, mRNA from the tissue sample may be isolated and cDNA prepared. Short chains of oligo d-T nucleotides may be hybridized with the poly-A tails of the mRNA and serve as a primer for the enzyme, reverse transcriptase, which synthesizes a complementary DNA (cDNA) strand. The cDNA may be enriched for the desired sequences using subtraction hybridization procedures following Davis et al. (Proc. Natl. Acad. Sci. USA 81: 2194-2198, 1984). The quality of the cDNA library may be determined by examining the cDNA insert size, and also by sequence analysis of a random selection of an appropriate number of clones from the library.

Amplification of the COP1 Gene from the cDNA Library

As described herein, COP1 nucleic acid molecules from the cDNA from the maize plant may be amplified through use of many available methods. The most preferred method of achieving such a goal may employ the polymerase chain reaction, i.e., "PCR" (Mullis et al., Cold Spring Harbor Symp. Quant. Biol. 51:263-273, 1986; Erlich et al., European Patent Application 50,424; European Patent Application 84,796, European Patent Application 258,017, European Patent Application 237,362; Mullis, European Patent Application 201,184; Mullis et al., U.S. Pat. No. 4,683,202; Erlich., U.S. Pat. No. 4,582,788; and Saiki et al., U.S. Pat. No. 4,683,194), using primer pairs that are capable of hybridizing to the proximal sequences that define the COP1 nucleic acid of the cDNA library in its double-stranded form.

The COP1 nucleic acid molecules may also be amplified by alternative methods, such as the "Ligase Chain Reaction", i.e., LCR (Barany, Proc. Natl. Acad. Sci, (U.S.A.) 88:189-193, 1991). LCR uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

Other known nucleic acid amplification procedures, such as allele-specific oligomers, branched DNA technology, transcription-based amplification systems, oligonucleotide ligation assay, or isothermal amplification methods may also be used to amplify and analyze the COP1 nucleic acid molecules from the cDNA library of a plant such as the maize plant (Malek et al., U.S. Pat. No. 5,130,238; Davey et al., European Patent Application 329,822; Schuster et al., U.S. Pat. No. 5,169,766; Miller et al., PCT Application WO 89/06700; Kwoh et al., Proc. Natl. Acad. Sci. (U.S.A.) 86:1173-1177, 1989; Landegren et al., Science 241: 1077-1080, 1988; Gingeras et al., PCT Application WO 88/10315; Walker et al., Proc. Natl. Acad. Sci. (U.S.A.) 89:392-396, 1992).

Sequencing of the COP1 Nucleic Acid from the cDNA Library

The COP1 nucleic acid molecule of the cDNA library from the maize plant may be sequenced after its amplification through use of many available methods. The most preferred method of achieving such a goal may employ the polymerase chain reaction ("PCR"), as described above, using primer pairs that are capable of hybridizing to the proximal sequences that define the COP1 cDNA library in its double-stranded form.

Antibody Production

In one of the preferred embodiments, antibodies to the maize COP1 of the present invention may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (Antibodies: A Laboratory Manual, Cold Spring Harbor Laboratory, Cold Spring Harbor, N.Y., 1988) and as in Goding (Monoclonal Antibodies: Principles and Practice, $2^{nd}$ eds, Academic Press, NY, 1986). The antibodies produced in the present invention are useful in immunoassays for determining the amount or presence of the COP1 protein. Such assays are also useful in quality controlled production of compositions containing COP1 of the present invention. In addition, the antibodies can be used to assess the efficacy of recombinant production of the COP1, as well as for screening expression libraries for the presence of COP1 encoding gene. They may also be used as affinity ligands for purifying and/or isolating the COP1 proteins. The COP1 antigens may be obtained by over expressing the full or partial length of the COP1 gene.

Promoter Selection and Vector Construction

Exogenous genetic material such as the wild type COP1 nucleic acid or its fragment thereof may be transferred into a plant cell by use of a DNA vector or construct designed for such a purpose. Design of such a vector is generally within the skill of the art (See, Plant Molecular Biology: A Laboratory Manual, Clark eds, Springer, N.Y., 1997).

In one of the preferred embodiments, the construct may be an antisense construct comprising the COP1 nucleic acid that is complementary to, and is capable of pairing, with the native COP1 mRNA and thus prevent translation of the native COP1 mRNA. See Mol et al. (FEBS Lett. 268: 427-430, 1990) and Green et al. (Annu. Rev. Biochem. 55: 569-597, 1986) for general description of the technique. An antisense vector may be constructed by standard procedures and introduced into cells.

In another preferred embodiment, the construct may be a regular transformation vector and the process involves a "dominant-negative" approach to reduce the functions of native COP1 proteins. In such a method, part or all of the COP1 normal nucleic acid sequence is placed under the control of a promoter so that a partial or whole sequence of a protein similar to the targeted native protein is produced in small or large quantity. These partial or whole sequence of the expressed COP1 proteins may interact with the native COP1 proteins in such a way that the expression level and function of the native COP1 proteins be reduced. Because of the dominant-negative response of the endogenous cop1 alleles, this process will modify the shade-avoidance response to cause production of dominant-negative transgenic plants.

A construct or vector may include a plant promoter to express a COP1 nucleic acid or a fragment thereof. Promoters which are known or found to cause transcription of nucleic acid molecules can be used for DNA transcription in the maize plants. Such promoters may be obtained from a variety of sources such as plants and plant viruses. The promoter selected should not cause any potential problems for plant's growth and development. For example, the promoter selected should not cause any seed germination problems. A number of promoters which are active in plant cells have been described in the literature and have been used to create DNA constructs which have been expressed in plants (see, e.g., PCT publication WO 84/02913). For the purpose of the present invention, it is preferred that the particular promoter selected should be a light-inducible promoter. This light-inducible promoter should be, in the case of overexpressing the COP1 binding domains, capable of causing sufficient expression of the exogenous COP1 so that the exogenous COP1 proteins that include the protein-binding domains will be produced at a higher level to cause the binding activities in the transformants to result in the inactivity of the indigenous COP1 proteins. This light-inducible promoter should be, in the case of using the antisense technology, capable of producing an effective amount of mRNA from the exogenous COP1. Thus the effective amount of mRNA so produced will bind to the indigenous mRNA in the "antisense" orientation and cause suppression of the COP1. In either of the above two events, since the indigenous COP1 expression is suppressed, the desired phenotype will in expectation have shorter internodes. The promoters suitable for the present invention may include a cab promoter, an ATHB-2 promoter, a rice HB-2 promoter and a corn HB-2 promoter. In one of the preferred embodiments, the promoter may be the cab promoter. The methods for identifying and isolating a light-inducible promoter for the present invention can be readily available (e.g., Sheen, Plant Cell 2: 1027-1038, 1990).

In addition to promoters which are known to cause transcription of COP1 in plants as described above, other promoters may be identified for use in the present invention by screening a plant cDNA library for nucleic acids which are selectively or preferably expressed in the target tissues or cells.

The vector or construct may also include a structural gene or a fragment of the structural gene thereof. The "structural gene" or a fragment of the "structural gene" as used herein in the present invention comprises the COP1 gene or a fragment of the COP1 gene. The COP1 gene may be operatively linked downstream to a promoter as described above. In one of the preferred embodiments, the COP1 gene may be a wild type COP1 nucleic acid or a portion of the COP1 nucleic acid from any source. The COP1 nucleic acid may be from a maize plant and may be the ZmCOP1 nucleic acid as disclosed in the present invention having SEQ ID NO: 12.

The vector or construct may also include, within the coding region of interest, a nucleic acid sequence that acts, in whole or in part, to terminate transcription of that region. For example, such sequences that have been isolated include the Tr7 3' sequence and the nos 3' sequence (Ingelbrecht et al., The Plant Cell 1:671-680, 1989; Bevan et al., Nucleic Acids Res. 11:369-385, 1983) or the like.

The vector or construct may also include regulatory elements. Examples of such regulatory elements may include the Adh intron 1 (Callis et al., Genes and Develop. 1:1183-1200, 1987), the sucrose synthase intron (Vasil et al., Plant Physiol. 91:1575-1579, 1989), the TMV omega element (Gallie et al., The Plant Cell 1:301-311, 1989), and maize heat shock protein 70 (hsp70) intron (Brown and Santino, PCT Application WO93/19189). These and other regulatory elements may be included when appropriate.

The vector or construct may also include a selectable marker, a screenable marker and other elements as appropriate. Examples of these elements and markers mentioned herein are known in the art and may be readily used in the present invention. Those of the skilled in the art should refer to the following art for details (for selectable markers, see Potrykus et al., Mol. Gen. Genet. 199:183-188, 1985; Hinchee et al., Bio. Technology 6:915-922, 1988; Stalker et al., J. Biol. Chem. 263:6310-6314, 1988; European Patent Application 154,204; Thillet et al., J. Biol. Chem. 263: 12500-12508, 1988; for screenable markers see, Jefferson, Plant Mol. Biol, Rep. 5: 387-405, 1987; Jefferson et al., EMBO J. 6: 3901-3907, 1987; Sutcliffe et al., Proc. Natl. Acad. Sci. (U.S.A.) 75: 3737-3741, 1978; Ow et al., Science 234: 856-859, 1986; Ikatu et al., Bio. Technol. 8: 241-242, 1990; and for other elements see, European Patent Application Publication Number 0218571; Koziel et al., Plant Mol. Biol. 32: 393-405; 1996).

Methods and compositions for transforming bacteria and other microorganisms are known in the art (see, for example, Sambrook et al., Molecular Cloning: A Laboratory Manual, Second Edition, Cold Spring Harbor Laboratory Press, Cold Spring Harbor, N.Y., 1989).

Plant Transformation

The COP1 nucleic acid molecules of the present invention may be transferred into a plant cell and the plant cell regenerated into a whole plant. The COP1 nucleic acid molecules may be from any source, whether naturally occurring or otherwise obtained through methodologies in the field that are readily known to those skilled in the art, that are capable of being inserted into any plant cells. The COP1 nucleic acid molecules may be transferred into either monocotyledonous and dicotyledonous plants (See specifically, Chistou, Particle Bombardment for Genetic Engineering of Plants, Pp. 63-69 (*Zea mays*), Biotechnology Intelligence Unit. Academic Press, San Diego, Calif., 1996), and generally Chistou, Particle Bombardment for Genetic Engineering of Plants, Biotechnology Intelligence Unit. Academic Press, San Diego, Calif., 1996). As an example, the COP1 gene may be transformed into the maize plant using any of the methods as described herein.

There are many methods for transforming the COP1 nucleic acid molecules into plant cells such as the maize plant cells. Suitable methods are believed to include virtually any methods by which nucleic acid molecules may be introduced into the cells, such as by *Agrobacterium* infection or direct delivery of nucleic acid molecules that may include PEG-mediated transformation, electroporation and acceleration of DNA coated particles, etc. (Potrykus, Ann. Rev. Plant Physiol. Plant Mol. Biol. 42:205-225, 1991; Vasil, Plant Mol. Biol. 25: 925-937, 1994). For example, electroporation has been used to transform *Zea mays* protoplasts (Fromm et al., Nature 312:791-793, 1986). In general, the following are four most commonly used general methods for delivering a gene into cells: (1) chemical methods (Graham and van der Eb, Virology, 54:536-539, 1973); (2) physical methods such as microinjection (Capecchi, Cell 22:479-488, 1980), electroporation (Wong and Neumann, Biochem. Biophys. Res. Commun. 107:584-587, 1982); Fromm et al., Proc. Natl. Acad. Sci. (USA) 82:5824-5828, 1985); U.S. Pat. No. 5,384, 253; and the gene gun (Johnston and Tang, Methods Cell Biol. 43:353-365, 1994); (3) viral vectors (Clapp, Clin. Perinatol. 20:155-168, 1993; Lu et al., J. Exp. Med. 178: 2089-2096, 1993; Eglitis and Anderson, Biotechniques 6:608-614, 1988); and (4) receptor-mediated mechanisms (Curiel et al., Hum. Gen. Ther. 3: 147-154, 1992; Wagner et al., Proc. Natl. Acad. Sci. (USA) 89: 6099-6103, 1992).

Transformation of plant protoplasts can be achieved using methods based on calcium phosphate precipitation, polyethylene glycol treatment, electroporation, and combinations of these treatments. See for example (Potrykus et al., Mol. Gen. Genet., 205:193-200, 1986; Lorz et al., Mol. Gen. Genet., 199:178, 1985; Fromm et al., Nature, 319:791, 1986; Uchimiya et al., Mol. Gen. Genet.: 204:204, 1986; Callis et al., Genes and Development, 1183, 1987; Marcotte et al., Nature, 335:454, 1988). Application of these systems to different plant strains depends upon the ability to regenerate that particular plant strain from protoplasts. Among them are the methods for corn (U.S. Pat. No. 5,569,834, U.S. Pat. No. 5,416,011; McCabe et al., Biotechnology 6:923, 1988; Christou et al., Plant Physiol., 87:671-674, 1988). Illustrative methods for the regeneration of cereals from protoplasts are also described (Fujimura et al., Plant Tissue Culture Letters, 2:74, 1985; Toriyama et al., Theor. Appl. Genet. 205:34, 1986; Yamada et al., Plant Cell Rep. 4: 85, 1986; Abdullah et al., Biotechnology, 4:1087, 1986).

In one of the preferred embodiments, the present invention employs the *Agrobacterium*-mediated transformation technology to introduce the COP1 nucleic acid into the maize plant and to achieve a desired result. *Agrobacterium*-mediated transfer is a widely applicable system for introducing genes such as the COP1 gene into plant cells because the gene such as the COP1 gene can be introduced into whole plant tissues, thereby bypassing the need for regeneration of an intact plant from a protoplast. The use of *Agrobacterium*-mediated plant integrating vectors to introduce a nucleic acid into plant cells is well known in the art. See, for example, Fraley et al. (Biotechnology 3:629-635, 1985), Hiei et al. (U.S. Pat. No. 5,591,616), and Rogers et al. (Meth. In Enzymol 153: 253-277, 1987). Further, the integration of the Ti-DNA is a relatively precise process resulting in few rearrangements. The region of the COP1 nucleic acid to be transferred is defined by the border sequences and is usually inserted into the plant genome as described in Spielmann et al. (Mol. Gen. Genet., 205:34, 1986).

A transgenic plant such as a transgenic maize plant formed using *Agrobacterium* transformation methods typically contains a single added COP1 gene on one chromosome. Such a transgenic plant can be referred to as being heterozygous for the added COP1 gene. More preferred is a transgenic plant that is homozygous for the added COP1 gene; i.e., a transgenic plant that contains two added COP1 genes, one gene at the same locus on each chromosome of a chromosome pair. A homozygous transgenic plant can be obtained by sexually mating (selfing) an independent segregated transgenic plant that contains a single added COP1 gene, germinating some of the seeds produced and analyzing the resulting plants produced for the COP1 gene.

It is understood that two different transgenic plants can also be mated to produce offspring that contain two independently segregating added, exogenous COP1 genes. Selfing of appropriate progeny can produce plants that are homozygous for both added, exogenous COP1 genes that encode a COP1 polypeptide. Back-crossing to a parental plant and out-crossing with a non-transgenic plant are also contemplated, as is vegetative propagation.

Regeneration of the Transformed Plants

The regeneration, development, and cultivation of plants such as the maize plants from transformants or from various transformed explants are well known in the art (Weissbach and Weissbach, In: Methods for Plant Molecular Biology, Eds., Academic Press, Inc. San Diego, Calif., 1988). This regeneration and growth process may typically include the steps of selection of transformed cells containing exogenous COP1 genes, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The regeneration of plants containing the foreign, exogenous gene that encodes a protein of interest is well known in the art. As described in the present invention, the regenerated plants such as the regenerated maize plants that contain the COP1 nucleic acids, either wild type or chemically synthesized, that encode for the COP1 proteins, may be preferably self-pollinated to provide homozygous transgenic maize plants, as discussed before. Otherwise, pollen obtained from the regenerated maize plants may be crossed to seed-grown plants of agronomically important lines. Conversely, pollen from plants of these important lines is used to pollinate regenerated plants. A transgenic maize plant of the present invention may be cultivated using methods well known to one skilled in the art.

There are a variety of methods for the regeneration of plants from plant tissue. The particular method of regeneration will depend on the starting plant tissue and the particular plant species to be regenerated. Monocotyledonous plants, or monocot plants, may be transformed with a COP1 nucleic acid and then regenerated. Transformation of monocot plants using electroporation, particle bombardment, and *Agrobacterium* has also been reported. Transformation and plant regeneration have been achieved in many monocot plants that include maize, asparagus, barley and wheat, etc. Dicotyledonous plants, or dicot plants, may also be transformed with COP1 nucleic acid and regenerated. Methods for transforming dicot plants, primarily by use of *Agrobacterium tumefaciens*, and obtaining transgenic plants have been published. Among them are the methods for soybean, cotton, and other dicot plants.

Monocot and dicot plants to which the present invention may be applied may include those agronomic and horticultural crop plants. Examples of agronomic crop plants may include cereals such as maize, wheat, rye, barley, oats, buckwheat, sorghum and rice; non-cereals such as sunflower, canola, peas, beans, soybeans, cotton and linseed; vegetables such cauliflower, asparagus, lettuce, tobacco and mustard; and root crops such as sugarbeet, potato, sweet potato, carrot and turnip. Horticultural crops may include celery, tomato, egg plant, cucumber and squash. Fruit crops may include apple, apricot, peach, pear, plum, orange, blackberry, blueberry, strawberry, cranberry and lemon.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones (see, for example, Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: Analyzing DNA, 1, Cold Spring Harbor, N.Y., 1997).

The following examples further demonstrate several preferred embodiments of the present invention. Those skilled in the art will recognize numerous equivalents to the specific embodiments described herein. Such equivalents are intended to be within the scope of the present invention and claims.

EXAMPLES

Example 1. Computer-Aided Sequence Analysis

A COP1 protein sequence from *Arabidopsis* was retrieved from GenBank (ID 402685) and used as query to BLAST search sequence databases which identified clones in the databases that share high degree homology to *Arabidopsis* COP1. These clones may be used in cloning the full-length COP1 cDNA from these crop species from which the clones were originally obtained including maize.

Example 2. COP1 cDNA Cloning

To obtain the full-length sequence of maize COP1 cDNA, several RT-PCR, 5'race and 3'race polymerase chain reactions (PCR) were performed. One microgram of kernel cDNA, recovered from kernels 15 days after pollination (DAP) was used as template in all PCR reactions. The cDNA library had previously been cloned into pSPORT2. Two micromoles of maize COP1 gene specific forward primer L3062COP1F (5'GTACGGACATTCAGAGGACAC3'; SEQ ID NO: 1) and reverse primer L30623'COP1R (5'GTGTCCTCTGAATGTCCGTAC3'; SEQ ID NO: 2) combined with 0.1 mM dNTPs and 5 Units of Taq DNA polymerase was used in a 50 µL PCR reaction to determine the presence of COP1 in the 15 DAP kernel cDNA pools. PCR cycling conditions and parameters were as follows: 95° C. for 5 minutes (min) followed by 28 cycles at 95° C. for 30 seconds (sec), 60° C. for 30 sec and 72° C. for 30 sec. To obtain the most 5' sequences of COP1 cDNA, the complementary sequences of M13 Forward primer (5'CCCAGTCACGACGTTGTAAAACG3'; SEQ ID NO: 3) in pSPORT2 vector and the primer L3062cop1R, combined with 0.1 mM dNTPs and 5 units of HotStart Tae™ polymerase (Qiagen, Valencia, Calif.), were used in a 50 µL in a 5'-race PCR. PCR cycling conditions and parameters were as follows: 95° C. for 15 min, then 28 cycles at 95° C. for 30 sec, 60° C. for 30 sec and 72° C. for 3 min. An approximately 2 Kb PCR product was obtained, cloned into PCR-blunt TOPO II cloning vector (Invitrogen, Carlsbad, Calif.) and sequenced. In the meantime, COP1 gene specific primer L30624070F (5'AATGAAAAGAACTTTGTTGGC3'; SEQ ID NO: 4) and M13 reverse primer (5'AGCGGATAACAATTTCACACAGG3'; SEQ ID NO: 5) were mixed with 0.1 mM dNTPs and 5 Units Taq DNA polymerase in a 50 µL 3'race PCR to obtain the most 3'sequences of the COP1 cDNA. PCR cycling conditions and parameters were as follows: 95° C. for 5 min, then 28 cycles at 95° C. for 30 sec, 60° C. for 30 sec and 72° C. for 40 seconds. A 650 base pair PCR product was obtained, cloned into PCR-blunt TOPO II cloning vector, and sequenced. For subcloning purposes, and for obtaining a more reliable cDNA clone, COP1 cDNA was re-amplified from 15 DAP kernel cDNA library using forward primer COP15-6 (5'CTGCGCCATGGGCGACTCCTCGGTGG3'; SEQ ID NO: 6) containing NcoI site at the start codon of the COP1 open reading frame and reverse primer L30623'COP1R (SEQ ID NO: 2). A 50 µL of PCR cocktail was made as follows: 1 µg of 15 DAP kernel cDNA, 2 µM of Cop15-6 and L30623'Cop1R primers, 0.1 mM dNTPs, 5% DMSO, and 1×PCR reaction buffer (Mg++). Manual hot start PCR cyclings were initiated at 95° C. for 15 min. Then 2 units of Expand™ High-Fidelity DNA Polymerase (Roche, 173264) was added and PCR reaction was carried out under the following conditions and parameters: at 95° C. for 30 seconds, 60° C. for 30 sec and 68° C. for 6 min for a total of 28 cycles. A 2230 base pair maize COP1 cDNA sequence was obtained, and cloned into PCR-Blunt TOPO II cloning vector. The full-length COP1 cDNA sequence was confirmed by sequencing six independent clones. The sequence was named as ZmCOP1 (SEQ ID NO: 12). ZmCOP1 represents a full length cDNA sequence containing a 388 base pair 5' UTR, a coding region that encodes 694 amino acids (see translated amino acid sequence; SEQ ID NO: 13) and a 141 base pair 3' UTR. Based upon sequence homology analysis, the isolated maize COP1 nucleotide sequence has 50% and 71% identity with those of COP1 from *Arabidopsis* (gi7446130, Deng et al., Cell 27, 791-801, 1992) and rice (gi7592844), respectively (FIGS. 1 and 2). The maize COP1 protein sequence is also aligned with other COP1 protein sequences from other species and shows 68% sequence identity to that of pea (gi3121867, Zhao et al., Biochimica et Biophysica Acta-Gene Structure and Expression 1395, 326-328, 1998), 69% to Japanese morning glory (gi11127996), 70% to *Arabidopsis* (gi7446130, Deng et al., Cell 27, 791-801, 1992), 71% to tomato (gi4090943), and 89% to rice (gi7592844), respectively (FIG. 3). The identity levels were determined by BLAST program (Altschul et al., Nucleic Acids Res. 25: 3389-3402, 1997) with default parameters (Expectation value (E): blank; Alignment view options: pairwise; Filter query sequence: no; Cost to open a gap: 0; Cost to extend a gap: 0; X dropoff value for gapped alignment: 0; Show GI's in defines: no; Penalty for a nucleotide mismatch: −3; Reward for a nucleotide match: 1; Threshold for extending hits: 0; Perform gapped alignment: yes; Query Genetic code to use: standard; DB Genetic code: standard; Believe the query define: no; Matrix: BLOSUM62; Word size: 0; Effective length of the database: 0; Query strand Use: both).

Example 3. Northern Blot Analysis of COP1 from the cDNA Library

Northern Blot analysis of the expression of maize COP1 during ear development was performed. Total RNA (15 µg each) from different tissues were mixed with one volume of RNA Sample Loading Buffer (Sigma, R-4268), heated at 65° C. for 10 min., chilled on ice for one min. and loaded on a 1% formaldehyde agarose gel. The RNA was separated on the gel under constant voltage at 65 v for 4 to 5 hours and then transferred onto a piece of nylon membrane at 4° C. overnight using a Schleicher & Schuell transfer system (Keene, N.H., USA 03431). A 157 base pair 3'UTR fragment of COP1 was amplified by PCR using forward primer 3'COP1 (5'TGCTCCTTGATGTTATGG3'; SEQ ID NO: 7) and reverse primer L30623'COP1R. A 910 base pair 5' fragment was also amplified by PCR using forward primer COP15-6 and COP301 (5'GATGAATTCATCAAGGAG-GATCAGAAGAAG3'; SEQ ID NO: 8). Purified PCR products (25 ng each) were labeled with p32dCTP using Random Primed DNA Labeling Kit (Boehringer Mannheim, Cat. #1004760). The membrane was hybridized with both labeled 3'UTR and 5'COP1 probes.

Example 4. Construction of Maize Transformation Vectors

Figure 5:
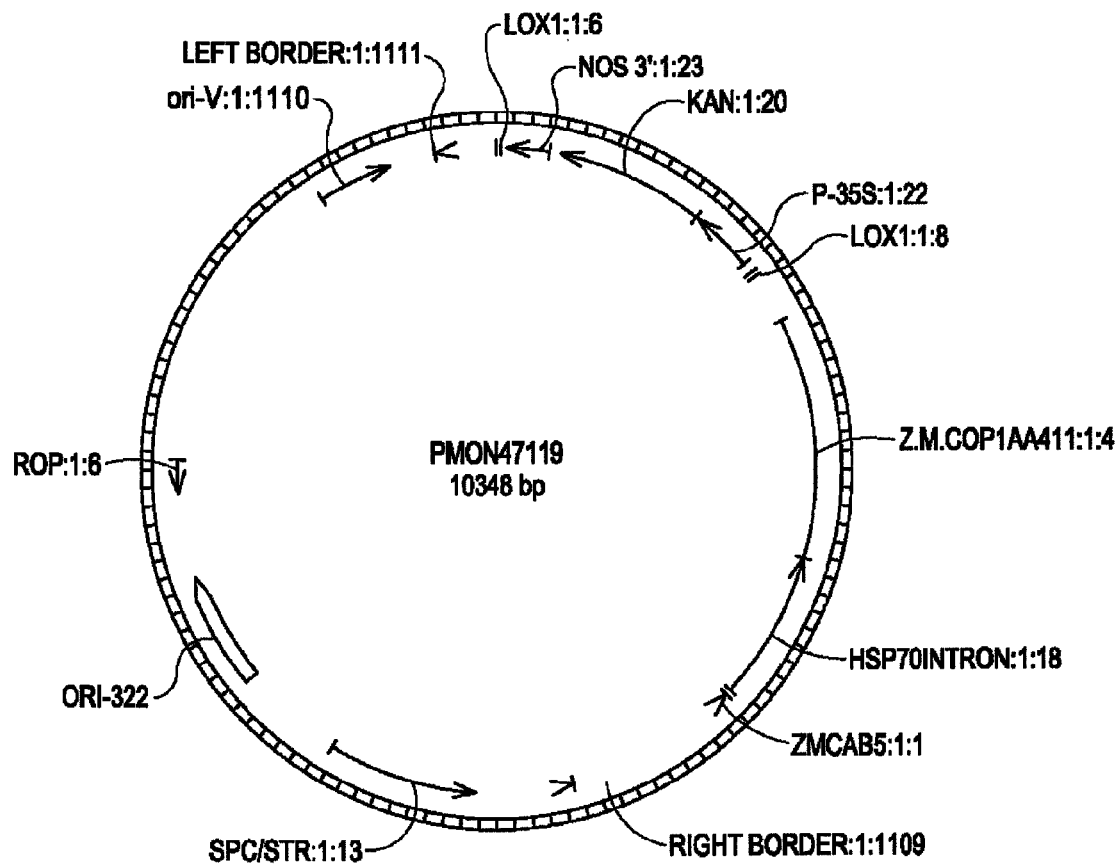
FIG. 5. A plasmid map of pMON47118. The coding sequence of the N-terminal end 301 amino acid residues of ZmCOP1 was placed under the control of a cab promoter.
Figure 6:
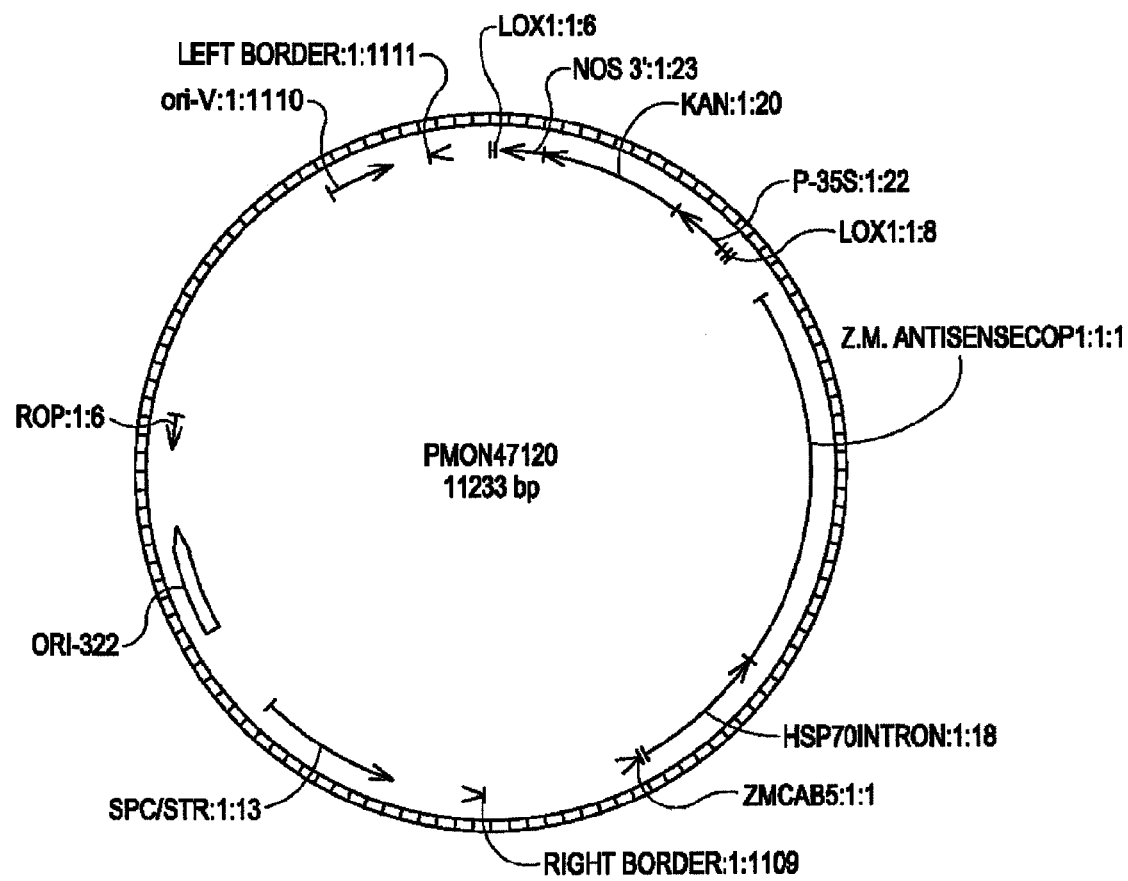
FIG. 6. A plasmid map of pMON47120. ZmCOP1 was cloned in the vector in reverse orientation and placed under the control of a cab promoter.

In an effort to identify an efficient way for reducing the endogenous COP1 mRNA and protein level, three sequences of the COP1 gene with different lengths were created and dominant negative and antisense strategies were employed. The dominant negative strategy employed a fragment of the 5' nucleotide sequence encoding a protein binding domain was cloned into an overexpression vector. Two sequences employing COP1 were created for this purpose, one containing the first 1233 nucleotide residues (SEQ ID NO: 14) encoding 411 amino acids (SEQ ID NO: 15) in pMON47119 (FIG. 4), and another containing the first 906 nucleotide residues (SEQ ID NO: 16) encoding 301 amino acids (SEQ ID NO: 17) in pMON47118 (FIG. 5). A full length COP1 was used in the antisense approach. The construct was pMON47120 and the detail of the vector was shown in FIG. 6. Forward primer of COPantisense5'-end (5'GATGAATTC-CTGCGGCATGGGCGAC3'; SEQ ID NO: 9) and reverse primer of COPantisense3'-end (5'AACCATGGACTGAAC-CTCTTGAACG3'; SEQ ID NO: 10) were used to sub-clone full-length maize COP1 for the antisense strategy. Primers COP15-6 and COP301 were used to sub-clone N-terminal 301 (N301) amino acid protein domain of maize COP1. This maize N301 protein domain was equivalent to N 282 protein dimerization domain of *Arabidopsis* COP1 (Deng et al., PCT Application WO 00/18940). Forward primer of COP15-6 and reverse primer of COP411 (5'GATGAAT-TCATCATTTCGAGACTCCAGC3'; SEQ ID NO: 11) with two stop codons (TGA) near EcoRI cleavage site were used to sub-clone the N-terminal 411 (N411) amino acid protein domain of the maize COP1. This N411 fragment was equivalent to the N392 fragment COP1 in *Arabidopsis* that contained the protein dimerization domain and core sequences required for COP1 protein translocation from cytoplasm to nucleus (PCT Application WO 00/18940). PCR mixture (50 µL) was made as follows: 100 ng of PCR-Blune-COP1 plasmid DNA, 2 µM of primers, 0.1 mM dNTPs, 5% DMSO, 1×PCR buffer, and 5U Expand High Fidelity DNA polymerase. PCR cycling conditions and parameters were as follows: 95° C., 5 min., followed by 25 cycles at 95° C. for 30 seconds, 60° C. for 30 seconds, 68° C., 6 min. for antisense COP1 amplification, 2 min. for COPaa301 amplification, and 3 min for COPaa411 amplification. The PCR products were gel purified, cloned into PCR-Blunt TOPO II cloning vector, and full-length sequenced.

To construct maize *Agrobacterium*-mediated transformation vectors, pMON32502 plasmid DNA was digested with HindIII, EcoRI and NcoI. A 3135 base pair HindIII and EcoRI vector backbone fragment was isolated. Plasmid DNA of pMON24037 was digested with HindIII and NcoI. A 1689 base pair of the HindIII and NcoI fragment containing the promoter of maize chlorophyll a/b binding protein and the hsp70 intron was obtained. PCR-Blunt vector containing antisense COP1, COP1aa301, and COP1aa411 were digested respectively with NcoI and EcoRI to obtain the NcoI and EcoRI fragments of antisense COP1, COP1aa301 and COP1aa411. The HindIII and EcoRI vector backbone fragment was ligated with the HindIII and NcoI cab promoter fragment, and NcoI and EcoRI antisense COP1, or COPaa301, or COPaa411, respectively, to form pMON47120, pMON47118, and pMON47119. The three constructs were then transformed individually into *Agrobacterium* strain ABI. All these gene constructs were under the control of cab promoter (light inducible) and were designed to reduce the functional ZmCOP1 protein level in the above-ground part of corn plants. The vector pMON47118 contained the coding sequence for N-terminal 301 amino acid residues of the ZmCOP1 gene that covered the dimmerization domain. The vector pMON47119 contained the nucleotide sequence coding for the 411 amino acid residues. The N-terminus of ZmCOP1 carried the dimerization and nuclear localization domains. pMON47120 contained the full-length antisense ZmCOP1 gene.

Figure 7:
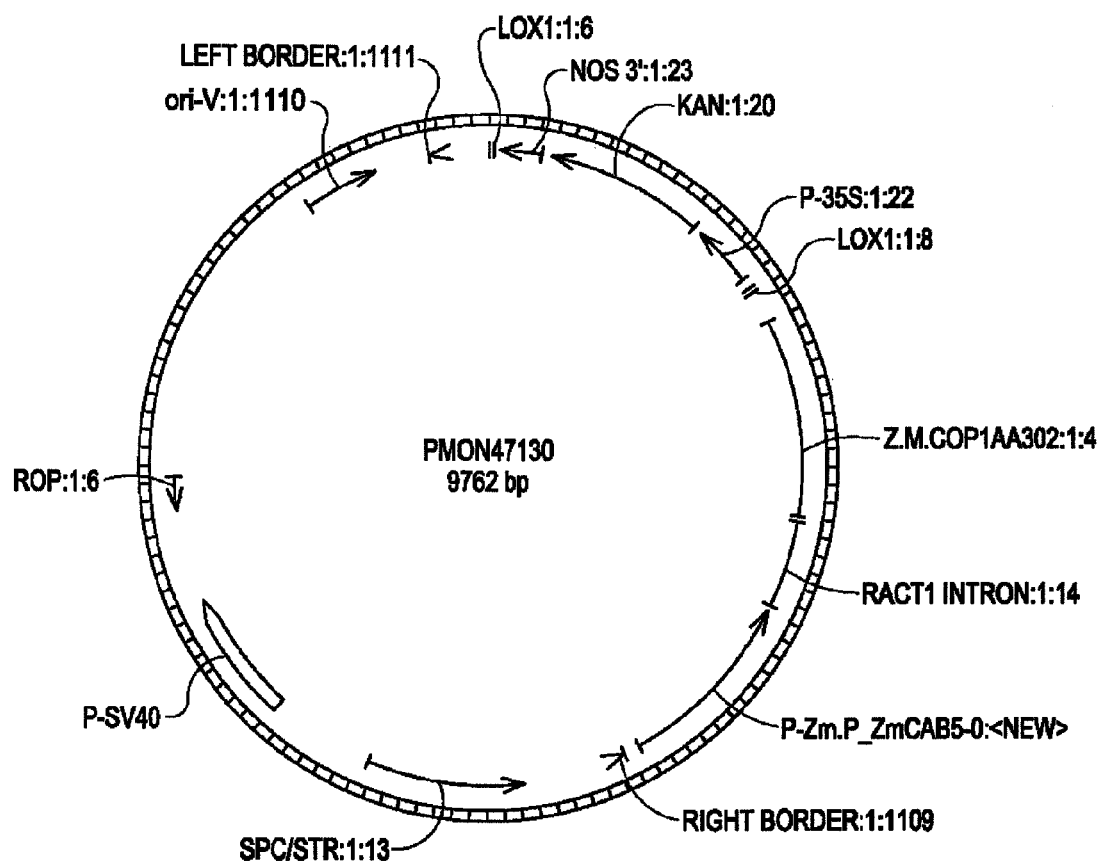
FIG. 7. A plasmid map of pMON47130. The coding sequence of the N-terminal end 301 amino acid residues of ZmCOP1 was placed under the control of a rice-actin promoter (RACT) promoter.
Figure 8:
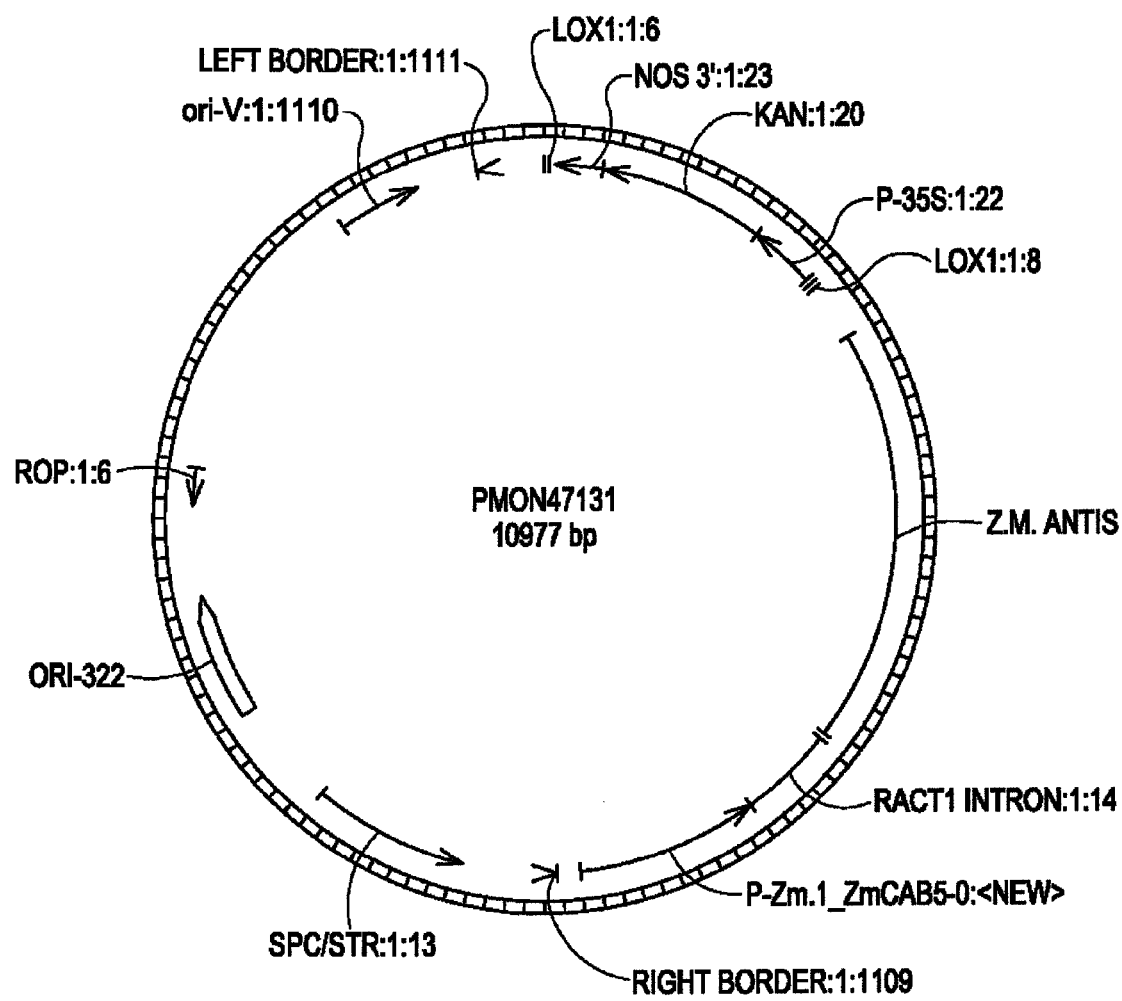
FIG. 8. A plasmid map of pMON47131. The coding sequence of the full length ZmCOP1 was cloned in the vector in reverse orientation and was placed under the control of a rice-actin promoter (RACT) promoter.

To serve as a check for evaluation of ZmCOP1 functions in corn, two additional ZmCOP1 constructs, i.e., pMON47130 and pMON47131, were made for transformation. A fragment of ZmCOP1 gene containing 903 nucleotide residues was driven by a constitutive promoter, i.e., a rice-actin (RACT) promoter. In order to construct pMON47130 transformation vector, a plasmid DNA of pMON47123 was digested with NcoI and XhoI restriction enzymes. A 1404 base-pair XhoI and NcoI fragment which contained rice-actin promoter (RACT) was obtained from pMON47123. Plasmid DNA of pMON47118 was also digested with NcoI and XhoI restriction enzymes. A fragment containing 8458 bp from 4379 bp XhoI site to 2719 bp NcoI site was obtained from pMON47118. Then, the 1404 bp fragment was ligated to the 8458 bp fragment and pMON47130 construct was made (FIG. 7). In order to make pMON47131 transformation vector, a plasmid DNA of pMON47120 was digested with NcoI and XhoI restriction enzymes. A fragment containing 9567 bp from 5594 bp XhoI site to 3934 bp NcoI site on pMON47120 was obtained. The RACT promoter fragment obtained from pMON47123 as described above was ligated to the 9567 bp fragment and the construct, i.e., pMON47131, was made (FIG. 8). The vector contained the full length ZmCOP1 coding sequence in reverse orientation.

Example 5. Overexpression of ZmCOP1 N301 Domain for Antibody Production

In order to make polyclonal antibody for maize COP1 protein, plasmid DNA of pMON47118 and pET30(a) (Novagen, Madison, Wis.) were digested with NcoI and EcoRI. The NcoI and EcoRI COPaa301 fragment was directionally cloned into pET30(a) vector under the control of the IPTG inducible T7 polymerase promoter and was transformed into E. coli BL21(DE3) competent cells. E. coli BL21 (DE3) cells containing pET30(a)-COPaa301 construct were induced with 3 mM IPTG overnight at room temperature. Proteins were purified under denaturing conditions using Ni-NTA Superflow resin (QIAGEN, Valencia, Calif.) as described in the manufacturer's protocol. An about 38 kDa His-tag COP301 protein was purified and confirmed by Western Blot analysis using monoclonal antibody against S-tag protein. About 1 mg purified COPaa301 protein was used to inoculate two rabbits for antibody production following the standard protocol of Pocono Rabbit Farm & Laboratory Inc. (Canadesis, Pa.). The preimmune serum from these two rabbits showed no reactivity with COPaa301 protein.

Example 6. Transformation of Corn Plant with the Vectors

1) Plant Materials

Ears from LH172 were obtained mostly from greenhouses and were usually harvested about 10 to 11 days post pollination. Before isolation, ears were stored from 0 to 5 days at 4° C. Ears were sterilized for 20 min in 50% (v/v) commercial bleach (Clorox®, with 5.25% sodium hypochlorite) followed by 3 rinses with sterile water.

TABLE 2

Media used in corn transformation (per liter).

| Component | ½ MS VI | ½ MS PL | Co-culture medium | LH172 MS | MS/BAP | MSOD |
|---|---|---|---|---|---|---|
| MS salts | .1 g | 0.1 g | 2.2 g | 4.4 g | 4.4 g | .1 g |
| Sucrose | 20 g | 0.1 g | 20 g | 30 g | 30 g | — |
| Maltose | — | — | — | — | — | 40 g |
| Glucose | 10 g | 36 g | 10 g | — | — | 20 g |
| l-Proline | 0.115 g | 0.115 g | 0.115 | 1.36 g | 1.36 g | — |
| Casamino Acids | — | — | — | 0.05 g | 0.05 g | — |
| Glycine | 2 mg | 2 mg | 2 mg | — | — | — |
| l-Asparagine | — | — | — | — | — | 150 mg |
| myo-Inositol | 100 mg | 100 mg | 100 mg | — | — | 100 mg |
| Nicotinic Acid | 0.5 mg | 0.5 mg | 0.5 mg | 0.65 mg | 0.65 mg | 0.65 mg |
| Pyridoxine•HCl | 0.5 mg | 0.5 mg | 0.5 mg | 0.125 mg | 0.125 mg | 0.125 mg |
| Thiamine•HCl | 0.1 mg | 0.1 mg | 0.6 mg | 0.125 mg | 0.125 mg | 0.125 mg |
| Ca Pantothenate | — | — | — | 0.125 mg | 0.125 mg | 0.125 mg |
| 2,4-D | — | — | 3 mg | 0.5 mg | 0.5 mg | — |
| Picloram | — | — | — | 2.2 mg | .1 mg | — |
| Silver Nitrate | — | — | — | 3.4 mg | — | — |
| Na-Thiosulfate | — | — | — | — | — | — |
| Phytagar | — | — | — | 7.0 g | 7.0 g | 7.0 g |
| Low EEO agarose | — | — | 5.5 g | — | — | — |

2) Agrobacterium Induction and Inoculation

Agrobacterium tumefaciens (ABI strain) was grown in LB liquid medium (50 mL medium per 250 mL flask) containing 100 mg/L kanamycin and 50 mg/L spectinomycin for an initial overnight propagation (on a rotary shaker at 150 to 160 rpm) at 27° C. Ten mL of the overnight Agrobacterium suspension was transferred to 50 mL of fresh LB in a 250 mL flask (same medium additives and culture conditions as stated above) and grown for approximately 8 hours. Suspension was centrifuged around 3500 rpm and pellet resuspended in AB minimal medium (now containing ½ the level of spectinomycin and kanamycin used for LB) containing 100 μM acetosyringone (AS) for a final concentration of $0.2 \times 10^9$ cfu/mL (or an OD of 0.2 at 660 nm). These Agrobacterium cultures were allowed to incubate as described above for approximately 15 to 16 hours. The Agrobacterium suspension was harvested via centrifugation and washed in ½ MS VI medium (Table 2) containing AS. The suspension was then centrifuged again before being brought up in the appropriate amount of ½ MS PL (Table 2) (also containing AS) so that the final concentration of Agrobacterium was $1 \times 10^9$ cfu/mL (which is equal to an OD of 1.0 at 660 nm). Immature embryos from each ear of a LH172 plant (1.5 mm to 2.0 mm long) were directly dissected into a 1.5-mL eppendorf tube with ½ MS PL containing Agrobacterium at an OD of 1.0. The eppendorf tube was capped tightly and inverted 3 times so that embryos inside were fully immersed. About half of the solution in the tube was drained by using a sterile SAMCO transfer pipette. The rest of the solution together with the embryos were poured into 2-3 layers of sterile Baxter filter paper (5.5 cm in diameter). Embryos were removed from the filter paper by flipping the filter paper over and slightly pressing it against the co-culture medium (Table 2) with the addition of 20 μM silver thiosulfate in the petri dish. The embryos were cultured at 23° C. for 1 day and then were transferred to the first selection medium (LH172MS; Table 2).

3) Callus Induction and Selection (in Dark)

Selection was performed in LH172 medium with 500 mg/L carbenicillin and 100 mg/L paromomycin. Three transfers to new plates containing the same medium were made every two weeks.

4) Regeneration (in Light)

Paromomycin resistant callus was first moved to MS/BAP medium (Table 2) with with 3.5 mg/L 6-BA for 5 to 7 days. After the 6-BA pulse, callus with green shoot tips were moved to MSOD (Table 2) with 100 mg/L paromomycin plates and were cultured for another 10 to 12 days. After this stage, green shoots started to grow out as well as white roots. Those small plantlets were transferred to phytatray (1 event per phytatray) containing MSOD media with 100 mg/L paromomycin. After 2 to 3 weeks, plants were ready to be transplanted into soil. Plants were acclimated in the growth chamber for week and then moved to the greenhouse for hardening. Plants were screened for the presence of nptII after 3 to 5 days of the hardening process. Only nptII positive plants were considered for further experimentation.

Example 7. R0 and R1 Transgenic Plants

Figure 9:
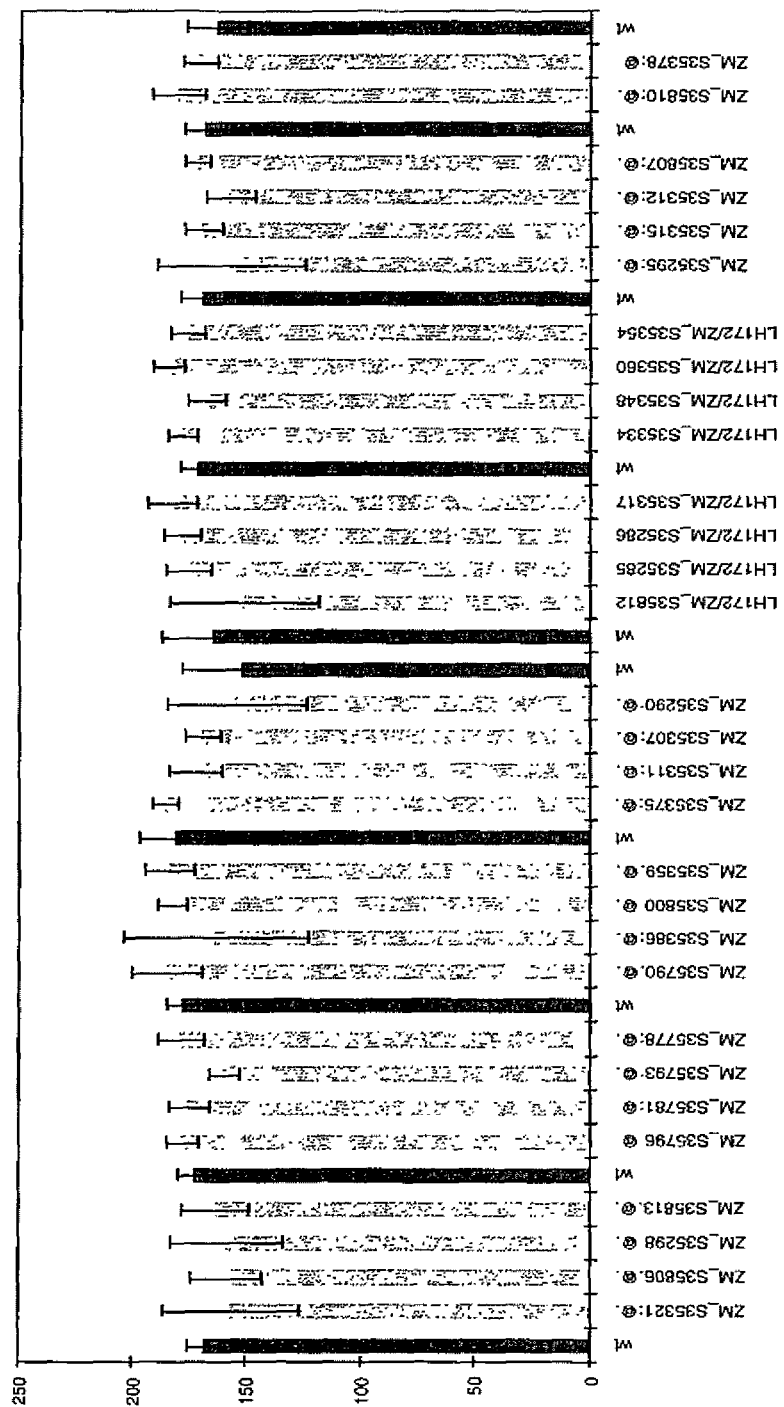
FIG. 9. The height comparison of the transformed R1 plants with the wild type plants at maturity. The average height and growth rate of some R1 transformed plants from pMON47118 in several events were lower compared to those of the wild type plants growing nearby. LH172 is a wild type inbred used for transformation; ZM is a transformed R1 plant; LH172/ZM represents a F1 plant obtained by crossing LH172 plant with a transformed R0 plant. Each number under each bar in the figure, e.g., ZM 535321, represents one event.

A total of 30 events from pMON47118 construct were selected from 137 R0 plants (79 events) based on the expression levels of gene of interest (GOI) by Northern and Western Blot analyses. Among the 30 events, 8 events had only F1 seeds and 22 events had R1 seeds. Twenty R1 or F1 seeds of each of these events were planted in a greenhouse. Phenotype observations were conducted weekly including germination, leaf color, plant height, growth rate, tassel morphology, ear morphology and ear number. The average height and growth rate of several events were lower compared to the wild type plants growing nearby (FIG. 9). In comparison of wild type and transformed adult plants, several transformed R1 plants in the event 535307 showed better ear growth, i.e., more and larger ears at third and fourth nodes, and distinct ear morphology, i.e., longer husk leaves. These phenotypic changes may be attributed to the COP1 transgene. Variations among individual plants in an event will be examined for correlation to the presence and expression level of the COP1 transgene. Cells transformed with a full length or a fragment of ZmCOP1 is used to produce young corn plants using standard protocols. These plants are called R0 generation plants. R0 plants are generated from many transformation events. These plants are grown in greenhouse and screened for the presence of ZmCOP1 transgene by PCR. The messenger RNA and protein expression level of the transgene in R0 plants are examined by Northern and Western blotting techniques. Events are selected based on the presence and expression level of the transgene in the R0 plants. The selected events are planted as R1 plants. R1 plants are examined for the presence of the transgene, the transgene expression level and the expected phenotypic traits such as short internodes and better ear development. All the data are used in selecting R1 plants for R2 evaluation. Those R1 plants that show a moderate to high level of transgene expression and a desired phenotype (shorter internodes and better ear development at high density) are chosen. R2 plants are planted in field as pedigree lines. The zygosity of each line is determined by the presence of the transgene in each plant in the line and by the positive/negative segregation ratio of its R1 predecessor. A few lines are selected based on their phenotype, transgene expression and homozygosity. These lines are crossed with another one or more inbred lines to make hybrid seeds. The hybrid seeds are planted at different density (20,000, 30,000 and 40,000 plants/acre) side by side with a control hybrid that is a best yield performer. The lines that give the best hybrid yield and the best density regimes are selected for further yield testing. The best line or lines proven in these yield trails are bulked up and grown in a large scale. For example, grow the new hybrid at 30,000 plants/acre, resulting in a 10% increase in biomass. Because the ZmCOP1 transgene is able to reduce shade avoidance response and hold harvest index the same, this results in a 10% yield gain. In some selected lines, reduced shade avoidance response also enhances harvest index; this increases yield even more.

Example 8. Constitutive Expression of ZmCOP1 in Corn

Figure 10:
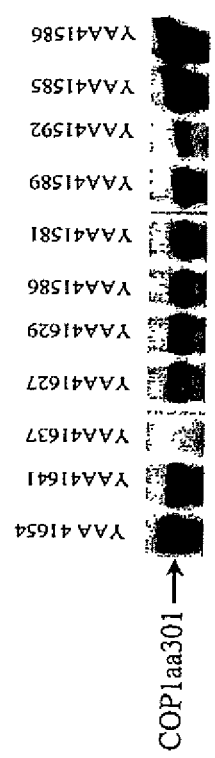
FIG. 10. Western analysis of YAA plants

A construct harboring a rice actin promoter and ZmCOP1aa301 gene fragment (pMON47130, FIG. 7) was transformed into corn and the events named YAA. Western blot analysis on the R0 plants showed that some YAA events have quite high expression of the ZmCOP1aa301 protein (FIG. 10).

Figure 11:
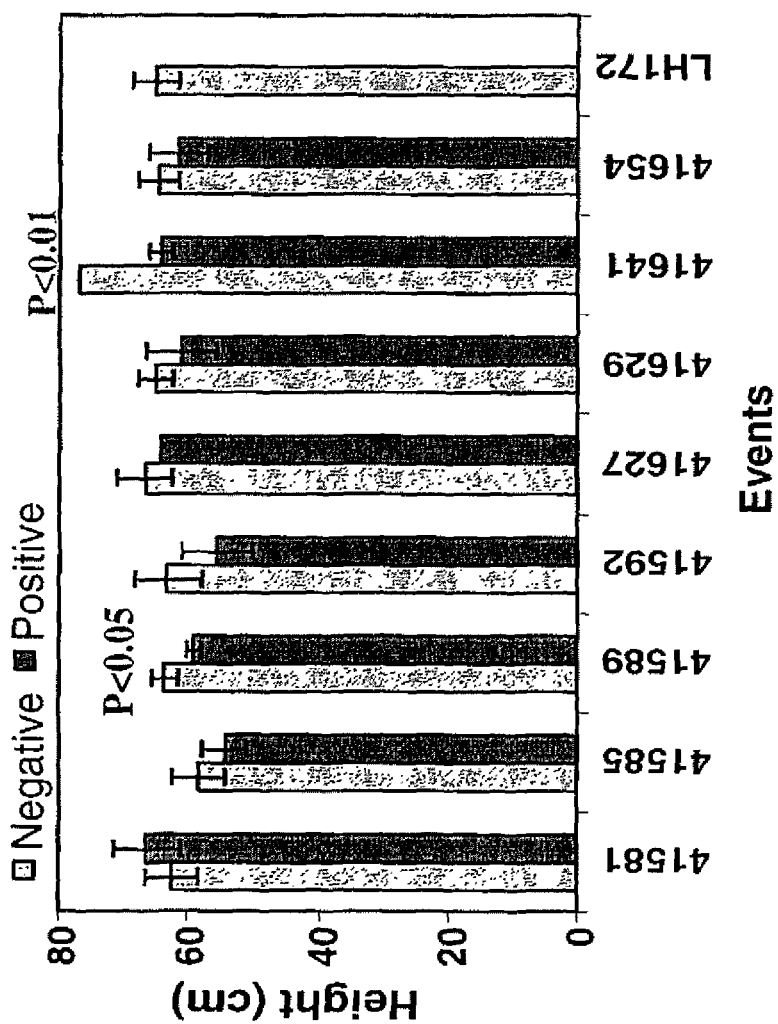
FIG. 11. Plant height of some YAA events at V11 stage

F1 seeds from eight events were selected for a dark and a light experiment. The dark experiment was conducted in a growth chamber with optimal conditions for corn seedling growth except that no light was provided. At day 5 after shoot emerging from soil, mesocotyl lengths of each seedling were measured. Positive and negative segregants were identified by Western blotting. Mesocotyl length data did not show a significant difference between positive and negative segregants. This agrees with the results of a similar experiment *Arabidopsis*. Eight events of YAA plants were also grown in a growth chamber with 500 mmol·m$^{-2}$·s$^{-1}$ white lights for 14 hours, and dark for 10 hours daily. Positive and negative plants were identified by Western blot analysis of ZmCOP1aa301 protein. Plant heights were measured weekly. The comparisons of positive and negative plant height are shown in FIG. 2. The results indicated that expression of ZmCOP1aa301 in maize using rice actin (RACT) promoter may have resulted shorter plants; while 7 out of 8 event showed a trend of shorter stature in the positive plants at V11 stage, the difference in two of these events was statistically significant at p=0.05 and p=0.01 level this sample size and in this growth conditions (FIG. 11).

Shorter Stature in Kyle R3 Plants

Figure 12:
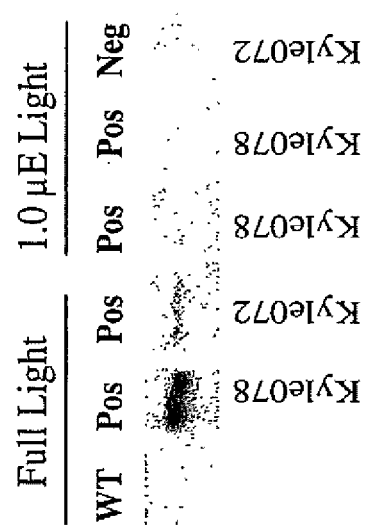
FIG. 12. Western analysis of Kyle plants grown under normal (full green house) light and weak light.
Figure 13:
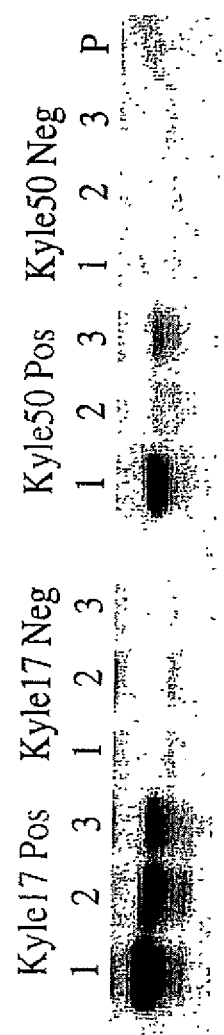
FIG. 13. Western blot analysis to determine protein expression levels in Kyle 17 and Kyle 50 events. Both Kyle positive (Pos) and negative (Neg) events are shown at different growth stages. Stage 1 represents the V3-V4 stage, 2 represents the V5-V7 stage, and 3 the VT stage. P is a positive control.
Figure 14:
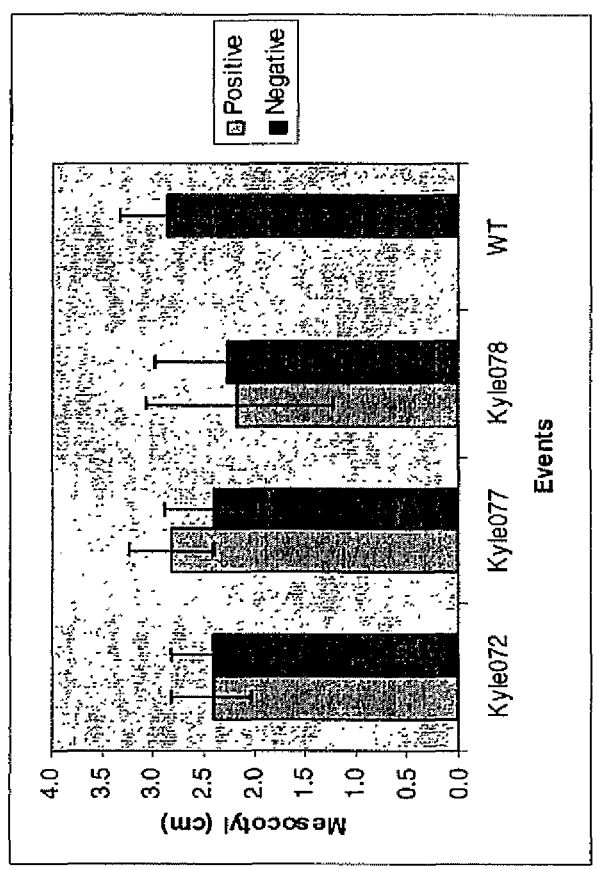
FIG. 14. Mesocotyl lengths of Kyle seedlings grown under 1 micromole per meter squared of light.
Figure 15:
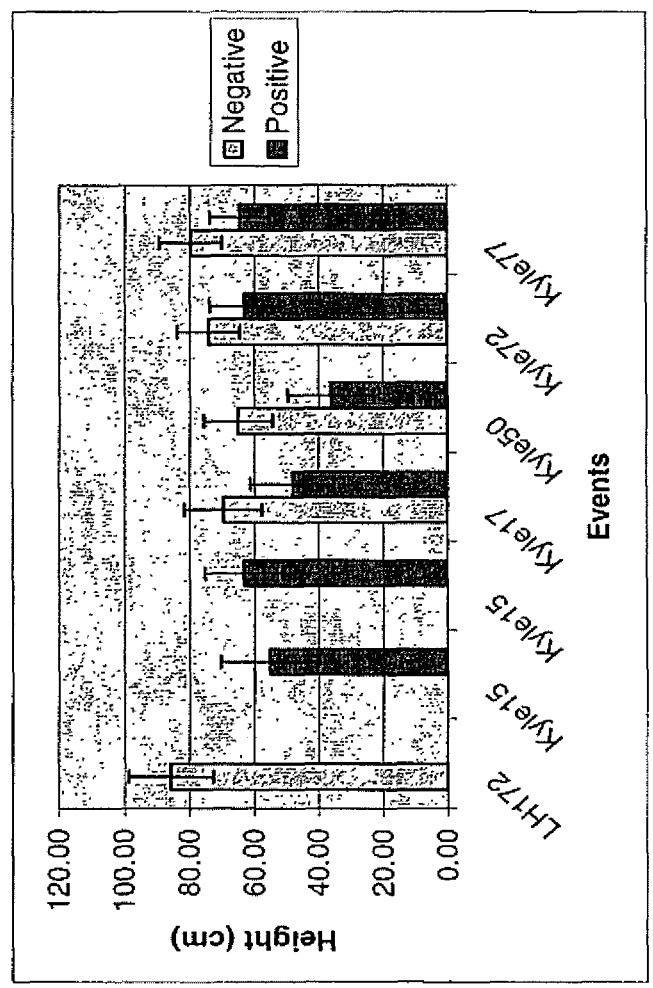
FIG. 15. Plant height of 5 Kyle events four weeks after transplanting.
Figure 16:
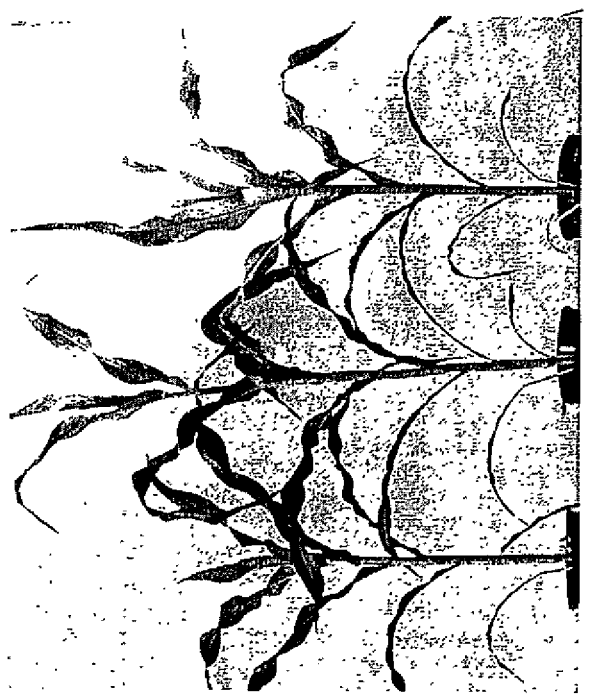
FIG. 16. Picture of positive (on both sides) and negative (center) lines from the Kyle 77 event.
Figure 17:
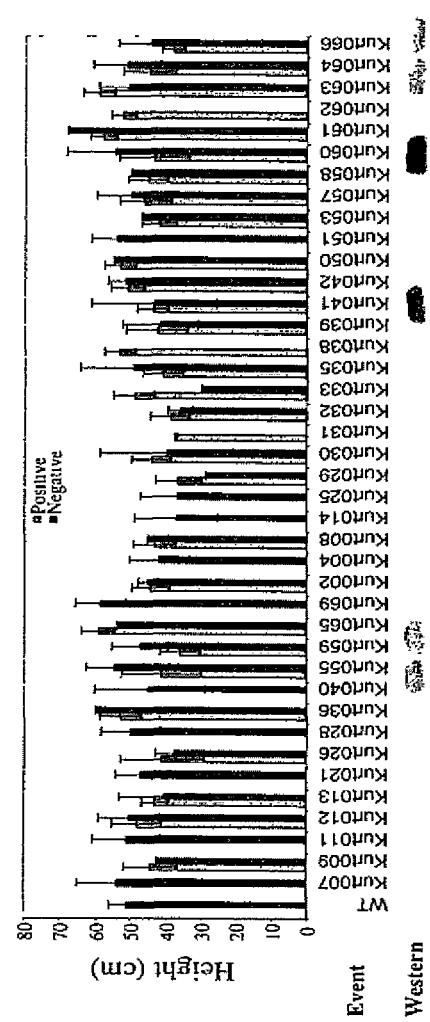
FIG. 17. Height of plants from the Kurt R1/F1 plants grown in the field. Shown below is the expression level of their transgene by Western analysis.

Kyle events are the transformants from construct pMON47118, which contains a light inducible CAB promoter and ZmCOP1aa301 gene fragment. Western analysis has shown that the ZmCOP1aa301 fragment was expressed in the Kyle plants under normal light (FIGS. 12 and 13) but not in dark or weak light (FIG. 12). Also, the gene was expressed at high level at different growth and developmental stages.

Seeds from some Kyle events were germinated and seedlings grown in dark and under 1 mmol/m2·s dim light and under normal green house light. Mesocotyl and coleoptile length were measured on day 10. Leaf samples were taken from each plant for DNA amplification (PCR) of the gene of interest. Seedlings grown under full green house light had virtually no mesocotyl, and their coleoptile length is short and uniform among Kyle positive, negative and wildtype plants. When seedlings were grown under 1 mmol/m2·s light, their coleoptile and mesocotyl were much longer, but no statistically significant difference was detected between positive and negative seedlings (FIG. 5).

A greenhouse experiment using R3 homozygous lines of Kyle events was carried out. Five homozygous positive lines and 5 of their corresponding negative lines were chosen and 100 seeds of each were planted in the Jerseyville greenhouse. PCR results on 12 plants of each line were used to confirm homozygosity. Thirty-six plants were transplanted for each line and the positions in the rows were randomized. Plant height data is being recorded on a weekly basis since transplanting. Positive plants were shorter compared to their corresponding negative lines in all events tested up to VT stage. The difference is statistically significant (Table 1). However, only event Kyle50 maintained this difference at maturity.

TABLE 3

Plant height and t-test of 5 Kyle events

| Event | Height (cm) | | | P-value of comparison | |
|---|---|---|---|---|---|
| | POS | NEG | LH172 | to NEG | to LH172 |
| Kyle15 | 55.19 | 71.22* | 85.83 | $3.7 \times 10^{-09}$* | $6.5 \times 10^{-12}$ |
| Kyle15 | 63.22 | 71.22* | 85.83 | $8.1 \times 10^{-05}$* | $5.5 \times 10^{-12}$ |
| Kyle17 | 48.13 | 69.73 | 85.83 | $1.8 \times 10^{-09}$ | $1.9 \times 10^{-15}$ |
| Kyle50 | 36.24 | 65.09 | 85.83 | $1.1 \times 10^{-13}$ | $1.4 \times 10^{-17}$ |
| Kyle72 | 63.08 | 74.21 | 85.83 | $2.1 \times 10^{-05}$ | $7.4 \times 10^{-12}$ |
| Kyle77 | 64.78 | 79.78 | 85.83 | $3.3 \times 10^{-09}$ | $2.6 \times 10^{-11}$ |

*Compared to the average of all negative events

Plant Height of Kurt R1

Kurt events are the transformants from construct pMON47119, which contains a light inducible CAB promoter and ZmCOP1aa411 gene fragment. Western analysis of some Kurt events has shown that the ZmCOP1aa411 fragment was expressed at high level in many of the events tested (FIG. 8). Some R1 and F1 Kurt events were grown in the field. Positive plants were identified by PCR. The height of both positive and negative plants was measured on a weekly basis up to VT stage. FIG. 8 summarizes data obtained at V10 stage, showing that the positive plants were shorter than their negatives in many events.

In summary, the above describes the present invention. It will be understood by those skilled in the art that, without departing from the scope and spirit of the present invention and without undue experimentation, the present invention can be performed within a wide range of equivalent parameters. While the present invention has been described in connection with specific embodiments thereof, it will be understood that it is capable of further modifications. The present invention covers any uses, variations, or adaptations of the invention following the principles of the invention in general. Various permutations and combination of the elements provided in all the claims that follow are possible and fall within the scope of this invention.

All publications and patents mentioned in this specification are herein incorporated by reference as if each individual publication or patent was specially and individually stated to be incorporated by reference.

We claim:

1. A recombinant DNA construct comprising a COP1 nucleotide sequence encoding a polypeptide having an amino acid sequence that has at least 90% sequence identity to SEQ ID NO: 21, said COP1 nucleotide sequence being operably linked upstream (5') to a heterologous promoter that functions in a plant and downstream (3') to a regulatory element, wherein the polypeptide binds to a COP1 protein.

2. A crop plant comprising the recombinant DNA construct of claim 1.

3. Progeny or seeds comprising the recombinant DNA construct of claim 1.

4. The recombinant DNA construct of claim 1, wherein said promoter comprises a light-inducible promoter.

5. The recombinant DNA construct of claim 4, wherein said promoter is selected from the group consisting of a cab promoter, an ATHB-2 promoter, and a far red light inducible promoter.

6. The recombinant DNA construct of claim 4, wherein said promoter comprises a cab promoter.

7. The recombinant DNA construct of claim 1, wherein said regulatory element comprises an intron.

8. The recombinant DNA construct of claim 7, wherein said intron comprises a hsp70 intron.

9. The recombinant DNA construct of claim 1, wherein said COP1 nucleotide sequence is isolated from a monocot plant.

10. The recombinant DNA construct of claim 9, wherein said COP1 nucleotide sequence is isolated from a rice maize plant.

* * * * *

SEQUENCE LISTING

```
<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gtacggacat tcagaggaca c                                                  21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
gtgtcctctg aatgtccgta c                                                  21

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3
cccagtcacg acgttgtaaa acg                                                23
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
aatgaaaaga actttgttgg c                                          21

<210> SEQ ID NO 5
<211> LENGTH: 23
<212> TYPE: DNA
<213> ORGANISM: Artificial Sequence
<220> FEATURE:
<223> OTHER INFORMATION: Synthetic primer

<400> SEQUENCE: 5
agcggataac aatttcacac agg                                        23

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
ctgcgccatg ggcgactcct cggtgg                                     26

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
tgctccttga tgttatgg                                              18

<210> SEQ ID NO 8
<211> LENGTH: 30
<212> TYPE: DNA
<213> ORGANISM: Artificial Sequence
<220> FEATURE:
<223> OTHER INFORMATION: Synthetic primer

<400> SEQUENCE: 8
gatgaattca tcaaggagga tcagaagaag                                 30

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gatgaattcc tgcggcatgg gcgac                                      25

<210> SEQ ID NO 10
<211> LENGTH: 25
<212> TYPE: DNA
<213> ORGANISM: Artificial Sequence
<220> FEATURE:
<223> OTHER INFORMATION: Synthetic primer
```

```
<400> SEQUENCE: 10
aaccatggac tgaacctctt gaacg                                           25

<210> SEQ ID NO 11
<211> LENGTH: 28
<212> TYPE: DNA
<213> ORGANISM: Artificial Sequence
<220> FEATURE:
<223> OTHER INFORMATION: Synthetic primer

<400> SEQUENCE: 11
gatgaattca tcatttcgag actccagc                                        28

<210> SEQ ID NO 12
<211> LENGTH: 2230
<212> TYPE: DNA
<213> ORGANISM: Zea mays

<400> SEQUENCE: 12
ctgcgccatg ggcgactcct cggtggccgg cgcgctcgtg ccgtctgtgc ccaagccgga     60
gcccgcgccg tccggtgaca cctccgcggc ggccgcggcg actacagcgg cgctggcgat    120
gccggaggag gcgggtatgc gcgcggcgtc ggcgtcgcct caggggcctg cggaggaggg    180
ggagggcccc gccgataggg accttctctg cccgatctgc atggccgtca tcaaggacgc    240
cttcctcacc gcatgcggcc acagcttctg ctacatgtgc atcgtcacgc atctcagcaa    300
caagagcgac tgcccctgct gcggccacta ccttaccaag gcccagctct accccaactt    360
tctccttgac aaggttctga gaaaatatc agcccaacaa atagcaaaaa cagcatcgcc    420
gatcgatcaa tttcgatgtg cattgcaaca gggaaatgaa atgggggtta agagttgga    480 tagccttatg actttgattg ctgagaagaa gcggcaaatg gaacaacaag aatcagagac    540
aaatatgcaa atattgctag tcttcttaca ctgccttaga aagcaaaagc tagaagagtt    600
gaatgagatt caaactgatc tacaatacat caaagaggat ataagttctg tggagagaca    660
tagggcagaa ttatatcgca caaaagaaag gtactccatg aagctgcgca tgctttttaga    720 tgagcctact cgcaaaaaaa tgtggccctc tcctatagac aaagctagct gtcgctttct    780
tcccaactct cggacaccac ttagtggatc atgtccagga actttacaga ataagaagct    840
tgatttgaaa gctcaagtaa gccatcaagg atttcaaagg agatgctc taacttcttc    900 tgatcctcct aactccccta caatcgggg taatgttatt gctaggaaga ggcgagttca    960
agcacagttc aatgagcttc aagaatacta cctgcaaaga cgtcgtactg gagcacaggc   1020
acgcagacag gaagaaagag atatagttgc aatgaataga gaaggctatc atgcaggtct   1080
tcaggatttc cagtctgtgc taacaacgtt cactcgatac agtcgtctac gtgtcattgc   1140
ggaactaaga catggagact tgtttcactc tgccaatatt gtatccagta ttgaatttga   1200
tcgtgatgat gaactatttg ctaccgctgg agtctcgaaa cgtattaaag tcttcgaatt   1260
ttccactgtt gttaatgaac catcagatgt gcattgccca gttgttgaaa tggctaccag   1320
atctaaactt agctgcctaa gctggaacaa gtactcaaaa aatattattg caagcagtga   1380
ctatgagggt atagtaactg tgtgggatgt tcagacccgt cagagtgtga tggaatatga   1440
agagcatgag aagagagcat ggagtgttga ttttttctcgc acagactctt caatgctagt   1500 atctggggagt gatgattgca aggtgaaagt gtggtgcaca aatcaagaag caagtgtgat   1560
caatattgat atgaaagcaa atatttgctc ggttaaatat aatcctggat caagcttcta   1620
cgttgcagtc ggatctgctg atcaccatat tcattacttt gatttacgta atccaagttc   1680
```

```
gcctgtccat attttcgggg ggcacaagaa agcagtatca tatgtgaaat tcttatctaa    1740
caatgagctt gcgtctgcat caacagatag cacattacgc ttatgggatg tcaaggataa    1800
ctgcccggta cggacattca gaggacacaa aaatgaaaag aactttgttg cttgtctgt     1860 gaacaatgaa tatattgctt gtggaagtga gacaaatgag gttttgttt atcacaaggc     1920 tatctcgaaa ccggcagcaa gccatagatt tgtatcttct gacccggatg atgccgatga    1980
tgatcctggt tcttatttca ttagtgctgt ctgctggaag agtgatagcc ctacgatgtt    2040
aactgctaac agtcagggga ccataaaagt tcttgtactt gctccttgat gttatggagg    2100
gcgttcaaga ggttcacagt actgtccagt tgtttccttt cgtgtcatta tattccccca    2160
aaattgggaa cggggggcata attgatctcc ggttagggaa tgaagttttg cagatggtca    2220
gctgacgtag                                                            2230
```

<210> SEQ ID NO 13
<211> LENGTH: 693
<212> TYPE: PRT
<213> ORGANISM: Zea mays

<400> SEQUENCE: 13

```
Met Gly Asp Ser Ser Val Ala Gly Ala Leu Val Pro Ser Val Pro Lys
1               5                   10                  15

Pro Glu Pro Ala Pro Ser Gly Asp Thr Ser Ala Ala Ala Ala Thr
            20                  25                  30

Thr Ala Ala Leu Ala Met Pro Glu Glu Ala Gly Met Arg Ala Ala Ser
        35                  40                  45

Ala Ser Pro Gln Gly Pro Ala Glu Glu Gly Glu Gly Pro Ala Asp Arg
    50                  55                  60

Asp Leu Leu Cys Pro Ile Cys Met Ala Val Ile Lys Asp Ala Phe Leu
65                  70                  75                  80

Thr Ala Cys Gly His Ser Phe Cys Tyr Met Cys Ile Val Thr His Leu
                85                  90                  95

Ser Asn Lys Ser Asp Cys Pro Cys Cys Gly His Tyr Leu Thr Lys Ala
            100                 105                 110

Gln Leu Tyr Pro Asn Phe Leu Leu Asp Lys Val Leu Lys Lys Ile Ser
        115                 120                 125

Ala Gln Gln Ile Ala Lys Thr Ala Ser Pro Ile Asp Gln Phe Arg Cys
    130                 135                 140

Ala Leu Gln Gln Gly Asn Glu Met Gly Val Lys Glu Leu Asp Ser Leu
145                 150                 155                 160

Met Thr Leu Ile Ala Glu Lys Lys Arg Gln Met Glu Gln Gln Glu Ser
                165                 170                 175

Glu Thr Asn Met Gln Ile Leu Leu Val Phe Leu His Cys Leu Arg Lys
            180                 185                 190

Gln Lys Leu Glu Glu Leu Asn Glu Ile Gln Thr Asp Leu Gln Tyr Ile
        195                 200                 205

Lys Glu Asp Ile Ser Ser Val Glu Arg His Arg Ala Glu Leu Tyr Arg
    210                 215                 220

Thr Lys Glu Arg Tyr Ser Met Lys Leu Arg Met Leu Leu Asp Glu Pro
225                 230                 235                 240

Thr Ala Gln Lys Met Trp Pro Ser Pro Ile Asp Lys Ala Ser Cys Arg
                245                 250                 255

Phe Leu Pro Asn Ser Arg Thr Pro Leu Ser Gly Ser Cys Pro Gly Thr
            260                 265                 270
```

```
Leu Gln Asn Lys Lys Leu Asp Leu Lys Ala Gln Val Ser His Gln Gly
            275                 280                 285

Phe Gln Arg Arg Asp Ala Leu Thr Ser Ser Asp Pro Pro Asn Ser Pro
    290                 295                 300

Ile Gln Ser Gly Asn Val Ile Ala Arg Lys Arg Arg Val Gln Ala Gln
305                 310                 315                 320

Phe Asn Glu Leu Gln Glu Tyr Tyr Leu Gln Arg Arg Thr Gly Ala
                325                 330                 335

Gln Ala Arg Arg Gln Glu Arg Asp Ile Val Ala Met Asn Arg Glu
            340                 345                 350

Gly Tyr His Ala Gly Leu Gln Asp Phe Gln Ser Val Leu Thr Thr Phe
                355                 360                 365

Thr Arg Tyr Ser Arg Leu Arg Val Ile Ala Glu Leu Arg His Gly Asp
    370                 375                 380

Leu Phe His Ser Ala Asn Ile Val Ser Ser Ile Glu Phe Asp Arg Asp
385                 390                 395                 400

Asp Glu Leu Phe Ala Thr Ala Gly Val Ser Lys Arg Ile Lys Val Phe
                405                 410                 415

Glu Phe Ser Thr Val Val Asn Glu Pro Ser Asp Val His Cys Pro Val
                420                 425                 430

Val Glu Met Ala Thr Arg Ser Lys Leu Ser Cys Leu Ser Trp Asn Lys
            435                 440                 445

Tyr Ser Lys Asn Ile Ile Ala Ser Ser Asp Tyr Glu Gly Ile Val Thr
            450                 455                 460

Val Trp Asp Val Gln Thr Arg Gln Ser Val Met Glu Tyr Glu Glu His
465                 470                 475                 480

Glu Lys Arg Ala Trp Ser Val Asp Phe Ser Arg Thr Asp Ser Ser Met
                485                 490                 495

Leu Val Ser Gly Ser Asp Asp Cys Lys Val Lys Val Trp Cys Thr Asn
                500                 505                 510

Gln Glu Ala Ser Val Ile Asn Ile Asp Met Lys Ala Asn Ile Cys Ser
            515                 520                 525

Val Lys Tyr Asn Pro Gly Ser Ser Phe Tyr Val Ala Val Gly Ser Ala
            530                 535                 540

Asp His His Ile His Tyr Phe Asp Leu Arg Asn Pro Ser Ser Pro Val
545                 550                 555                 560

His Ile Phe Gly Gly His Lys Lys Ala Val Ser Tyr Val Lys Phe Leu
                565                 570                 575

Ser Asn Asn Glu Leu Ala Ser Ala Ser Thr Asp Ser Thr Leu Arg Leu
            580                 585                 590

Trp Asp Val Lys Asp Asn Cys Pro Val Arg Thr Phe Arg Gly His Lys
    595                 600                 605

Asn Glu Lys Asn Phe Val Gly Leu Ser Val Asn Asn Glu Tyr Ile Ala
610                 615                 620

Cys Gly Ser Glu Thr Asn Glu Val Phe Val Tyr His Lys Ala Ile Ser
625                 630                 635                 640

Lys Pro Ala Ala Ser His Arg Phe Val Ser Ser Asp Pro Asp Asp Ala
                645                 650                 655

Asp Asp Asp Pro Gly Ser Tyr Phe Ile Ser Ala Val Cys Trp Lys Ser
                660                 665                 670

Asp Ser Pro Thr Met Leu Thr Ala Asn Ser Gln Gly Thr Ile Lys Val
    675                 680                 685
```

Leu Val Leu Ala Pro
    690

<210> SEQ ID NO 14
<211> LENGTH: 1233
<212> TYPE: DNA
<213> ORGANISM: Zea mays

<400> SEQUENCE: 14

```
actttatgtg acagcagacg tgcactggcc aggggatca ccatccgtcg ccccgggtgt      60
caataatatc actctgtaca tccacaaaca gacgatacgg ctctctcttt tataggtgta     120
aaccttaaac tgccgtacgt ataggctgcg caactgttgg gaagggcgat cggtgcgggc     180
ctcttcgcta ttacgccagc tggcgaaagg gggatgtgct gcaaggcgat taagttgggt     240
aacgccaggg ttttcccagt cacgacgttg taaaacgacg gccagtgaat tgtaatacga     300
ctcactatag ggcgaattgg gccctctaga tgcatgctcg agcggccgcc agtgtgatgg     360
atatctgcag aattcgccct tctgcgccat gggcgactcc tcggtggccg gcgcgctcgt     420
gccgtctgtg cccaagccgg agcccgcgcc gtccggtgac acctccgcgg cggccgcggc     480
gactacagcg gcgctggcga tgccggagga ggcgggtatg cgcgcggcgt cggcgtcgcc     540
tcagggccct gcggaggagg gggagggccc cgccgatagg gaccttctct gcccgatctg     600
catggccgtc atcaaggacg ccttcctcac cgcatgcggc cacagcttct gctacatgtg     660
catcgtcacg catctcagca acaagagcga ctgcccctgc tgcggccact accttaccaa     720
ggcccagctc tacccaact ttctccttga caaggttctg aagaaaatat cagcccaaca     780
aatagcaaaa acagcatcgc cgatcgatca atttcgatgt gcattgcaac agggaaatga     840
aatgggggtt aaagagttgg atagccttat gactttgatt gctgagaaga agcggcaaat     900
ggaacaacaa gaatcagaga caaatatgca atattgcta gtcttcttac actgccttag     960
aaagcaaaag ctagaagagt tgaatgagat tcaaactgat ctacaataca tcaaagagga    1020
tataagttct gtggagagac ataggggcaga attatatcgc acaaaagaaa ggtactccat    1080
gaagctgcgc atgcttttag atgagcctac tgcgcaaaaa atgtggccct ctcctataga    1140
caaagctagc tgtcgctttc ttcccaactc tcggacacca cttagtggat catgtccagg    1200
aactttacag aataagaagc ttgatttgaa agc                                  1233
```

<210> SEQ ID NO 15
<211> LENGTH: 411
<212> TYPE: PRT
<213> ORGANISM: Zea mays

<400> SEQUENCE: 15

Met Gly Asp Ser Ser Val Ala Gly Ala Leu Val Pro Ser Val Pro Lys
1               5                  10                  15

Pro Glu Pro Ala Pro Ser Gly Asp Thr Ser Ala Ala Ala Ala Thr
            20                  25                  30

Thr Ala Ala Leu Ala Met Pro Glu Glu Ala Gly Met Arg Ala Ala Ser
        35                  40                  45

Ala Ser Pro Gln Gly Pro Ala Glu Glu Gly Glu Gly Pro Ala Asp Arg
    50                  55                  60

Asp Leu Leu Cys Pro Ile Cys Met Ala Val Ile Lys Asp Ala Phe Leu
65                  70                  75                  80

Thr Ala Cys Gly His Ser Phe Cys Tyr Met Cys Ile Val Thr His Leu
                85                  90                  95

```
Ser Asn Lys Ser Asp Cys Pro Cys Cys Gly His Tyr Leu Thr Lys Ala
            100                 105                 110

Gln Leu Tyr Pro Asn Phe Leu Leu Asp Lys Val Leu Lys Lys Ile Ser
        115                 120                 125

Ala Gln Gln Ile Ala Lys Thr Ala Ser Pro Ile Asp Gln Phe Arg Cys
    130                 135                 140

Ala Leu Gln Gln Gly Asn Glu Met Gly Val Lys Glu Leu Asp Ser Leu
145                 150                 155                 160

Met Thr Leu Ile Ala Glu Lys Lys Arg Gln Met Glu Gln Gln Glu Ser
                165                 170                 175

Glu Thr Asn Met Gln Ile Leu Leu Val Phe Leu His Cys Leu Arg Lys
            180                 185                 190

Gln Lys Leu Glu Glu Leu Asn Glu Ile Gln Thr Asp Leu Gln Tyr Ile
        195                 200                 205

Lys Glu Asp Ile Ser Ser Val Glu Arg His Arg Ala Glu Leu Tyr Arg
    210                 215                 220

Thr Lys Glu Arg Tyr Ser Met Lys Leu Arg Met Leu Asp Glu Pro
225                 230                 235                 240

Thr Ala Gln Lys Met Trp Pro Ser Pro Ile Asp Lys Ala Ser Cys Arg
                245                 250                 255

Phe Leu Pro Asn Ser Arg Thr Pro Leu Ser Gly Ser Cys Pro Gly Thr
            260                 265                 270

Leu Gln Asn Lys Lys Leu Asp Leu Lys Ala Gln Val Ser His Gln Gly
        275                 280                 285

Phe Gln Arg Arg Asp Ala Leu Thr Ser Ser Asp Pro Pro Asn Ser Pro
    290                 295                 300

Ile Gln Ser Gly Asn Val Ile Ala Arg Lys Arg Val Gln Ala Gln
305                 310                 315                 320

Phe Asn Glu Leu Gln Glu Tyr Tyr Leu Gln Arg Arg Thr Gly Ala
                325                 330                 335

Gln Ala Arg Arg Gln Glu Glu Arg Asp Ile Val Ala Met Asn Arg Glu
            340                 345                 350

Gly Tyr His Ala Gly Leu Gln Asp Phe Gln Ser Val Leu Thr Thr Phe
        355                 360                 365

Thr Arg Tyr Ser Arg Leu Arg Val Ile Ala Glu Leu Arg His Gly Asp
    370                 375                 380

Leu Phe His Ser Ala Asn Ile Val Ser Ser Ile Glu Phe Asp Arg Asp
385                 390                 395                 400

Asp Glu Leu Phe Ala Thr Ala Gly Val Ser Lys
                405                 410

<210> SEQ ID NO 16
<211> LENGTH: 903
<212> TYPE: DNA
<213> ORGANISM: Zea mays

<400> SEQUENCE: 16
actttatgtg acagcagacg tgcactggcc aggggatca ccatccgtcg ccccgggtgt    60
caataatatc actctgtaca tccacaaaca gacgatacgg ctctctcttt tataggtgta   120
aaccttaaac tgccgtacgt ataggctgcg caactgttgg gaagggcgat cggtgcgggc   180
ctcttcgcta ttacgccagc tggcgaaagg gggatgtgct gcaaggcgat taagttgggt   240
aacgccaggg ttttcccagt cacgacgttg taaaacgacg ccagtgaat tgtaatacga   300 ctcactatag ggcgaattgg gccctctaga tgcatgctcg agcggccgcc agtgtgatgg   360
```

```
atatctgcag aattcgccct tctgcgccat gggcgactcc tcggtggccg gcgcgctcgt    420
gccgtctgtg cccaagccgg agcccgcgcc gtccggtgac acctccgcgg cggccgcggc    480
gactacagcg cgctggcga tgccggagga ggcgggtatg cgcgcggcgt cggcgtcgcc    540
tcagggcct gcgaggagg gggagggccc cgccgatagg gaccttctct gcccgatctg    600
catggccgtc atcaaggacg ccttcctcac cgcatgcggc cacagcttct gctacatgtg    660
catcgtcacg catctcagca acaagagcga ctgcccctgc tgcggccact acctaccaa    720
ggcccagctc tacccccaact ttctccttga caaggttctg aagaaaatat cagcccaaca    780
aatagcaaaa acagcatcgc cgatcgatca atttcgatgt gcattgcaac agggaaatga    840
aatgggggtt aaagagttgg atagccttat gactttgatt gctgagaaga agcggcaaat    900
gga                                                                   903
```

<210> SEQ ID NO 17
<211> LENGTH: 301
<212> TYPE: PRT
<213> ORGANISM: Zea mays
<400> SEQUENCE: 17

```
Met Gly Asp Ser Ser Val Ala Gly Ala Leu Val Pro Ser Val Pro Lys
1               5                   10                  15

Pro Glu Pro Ala Pro Ser Gly Asp Thr Ser Ala Ala Ala Ala Ala Thr
            20                  25                  30

Thr Ala Ala Leu Ala Met Pro Glu Glu Ala Gly Met Arg Ala Ala Ser
        35                  40                  45

Ala Ser Pro Gln Gly Pro Ala Glu Glu Gly Glu Gly Pro Ala Asp Arg
    50                  55                  60

Asp Leu Leu Cys Pro Ile Cys Met Ala Val Ile Lys Asp Ala Phe Leu
65                  70                  75                  80

Thr Ala Cys Gly His Ser Phe Cys Tyr Met Cys Ile Val Thr His Leu
                85                  90                  95

Ser Asn Lys Ser Asp Cys Pro Cys Cys Gly His Tyr Leu Thr Lys Ala
            100                 105                 110

Gln Leu Tyr Pro Asn Phe Leu Leu Asp Lys Val Leu Lys Lys Ile Ser
        115                 120                 125

Ala Gln Gln Ile Ala Lys Thr Ala Ser Pro Ile Asp Gln Phe Arg Cys
    130                 135                 140

Ala Leu Gln Gln Gly Asn Glu Met Gly Val Lys Glu Leu Asp Ser Leu
145                 150                 155                 160

Met Thr Leu Ile Ala Glu Lys Lys Arg Gln Met Glu Gln Gln Glu Ser
                165                 170                 175

Glu Thr Asn Met Gln Ile Leu Leu Val Phe Leu His Cys Leu Arg Lys
            180                 185                 190

Gln Lys Leu Glu Glu Leu Asn Glu Ile Gln Thr Asp Leu Gln Tyr Ile
        195                 200                 205

Lys Glu Asp Ile Ser Ser Val Glu Arg His Arg Ala Glu Leu Tyr Arg
    210                 215                 220

Thr Lys Glu Arg Tyr Ser Met Lys Leu Arg Met Leu Leu Asp Glu Pro
225                 230                 235                 240

Thr Ala Gln Lys Met Trp Pro Ser Pro Ile Asp Lys Ala Ser Cys Arg
                245                 250                 255

Phe Leu Pro Asn Ser Arg Thr Pro Leu Ser Gly Ser Cys Pro Gly Thr
            260                 265                 270
```

```
Leu Gln Asn Lys Lys Leu Asp Leu Lys Ala Gln Val Ser His Gln Gly
        275                 280                 285

Phe Gln Arg Arg Asp Ala Leu Thr Ser Ser Asp Pro Pro
        290                 295                 300

<210> SEQ ID NO 18
<211> LENGTH: 2611
<212> TYPE: DNA
<213> ORGANISM: Zea mays

<400> SEQUENCE: 18
actttatgtg acagcagacg tgcactggcc aggggatca ccatccgtcg ccccgggtgt      60
caataatatc actctgtaca tccacaaaca gacgatacgg ctctctcttt tataggtgta    120
aaccttaaac tgccgtacgt ataggctgcg caactgttgg gaagggcgat cggtgcgggc    180
ctcttcgcta ttacgccagc tggcgaaagg gggatgtgct gcaaggcgat taagttgggt    240
aacgccaggg ttttcccagt cacgacgttg taaaacgacg gccagtgaat tgtaatacga    300
ctcactatag ggcgaattgg gccctctaga tgcatgctcg agcggccgcc agtgtgatgg    360
atatctgcag aattcgccct tctgcgccat gggcgactcc tcggtggccg gcgcgctcgt    420
gccgtctgtg cccaagccgg agcccgcgcc gtccggtgac acctccgcgg cggccgcggc    480
gactacagcg cgctggcga tgccggagga ggcgggtatg cgcgcggcgt cggcgtcgcc    540 tcagggcct gcggaggagg gggagggccc cgccgatagg gaccttctct gcccgatctg    600
catggccgtc atcaaggacg ccttcctcac cgcatgcggc cacagcttct gctacatgtg    660
catcgtcacg catctcagca caagagcga ctgcccctgc tgcggccact accttaccaa    720
ggcccagctc taccccaact ttctccttga caaggttctg aagaaaatat cagcccaaca    780
aatagcaaaa acagcatcgc cgatcgatca atttcgatgt gcattgcaac agggaaatga    840
aatgggggtt aaagagttgg atagcctat gactttgatt gctgagaaga gcggcaaat    900 ggaacaacaa gaatcagaga caaatatgca atattgcta gtcttcttac actgccttag    960
aaagcaaaag ctagaagagt tgaatgagat tcaaactgat ctacaataca tcaaagagga   1020
tataagttct gtggagagac ataggcaga attatatcgc acaaaagaaa ggtactccat   1080
gaagctgcgc atgctttag atgagcctac tgcgcaaaaa atgtggccct ctcctataga   1140
caaagctagc tgtcgctttc ttcccaactc tcggacacca cttagtggat catgtccagg   1200
aactttacag aataagaagc ttgatttgaa agctcaagta agccatcaag gatttcaaag   1260
gagagatgct ctaacttctt ctgatcctcc taactcccct atacaatcgg gtaatgttat   1320
tgctaggaag aggcgagttc aagcacagtt caatgagctt caagaatact acctgcaaag   1380
acgtcgtact ggagcacagg cacgcagaca ggaagaaaga gatatagttg caatgaatag   1440
agaaggctat catgcaggtc ttcaggattt ccagtctgtg ctaacaacgt tcactcgata   1500
cagtcgtcta cgtgtcattg cggaactaag acatggagac ttgtttcact ctgccaatat   1560
tgtatccagt attgaatttg atcgtgatga tgaactattt gctaccgctg gagtctcgaa   1620
acgtattaaa gtcttcgaat tttccactgt tgttaatgaa ccatcagatg tgcattgccc   1680
agttgttgaa atggctacca gatctaaact tagctgccta agctggaaca agtactcaaa   1740
aaatattatt gcaagcagtg actatgaggg tatagtaact gtgtgggatg ttcagacccg   1800
tcagagtgtg atggaatatg aagagcatga aagagagca tggagtgttg attttttctcg   1860 cacagactct tcaatgctag tatctgggag tgatgattgc aaggtgaaag tgtggtgcac   1920
```

| | | | |
|---|---|---|---|
| aaatcaagaa | gcaagtgtga | tcaatattga tatgaaagca aatatttgct cggttaaata | 1980 |
| taatcctgga | tcaagcttct | acgttgcagt cggatctgct gatcaccata ttcattactt | 2040 |
| tgatttacgt | aatccaagtt | cgcctgtcca tattttcggg gggcacaaga aagcagtatc | 2100 |
| atatgtgaaa | ttcttatcta | acaatgagct gcgtctgca tcaacagata gcacattacg | 2160 |
| cttatgggat | gtcaaggata | actgcccggt acggacattc agaggacaca aaaatgaaaa | 2220 |
| gaactttgtt | ggcttgtctg | tgaacaatga atatattgct tgtggaagtg agacaaatga | 2280 |
| ggttttgtt | tatcacaagg | ctatctcgaa accggcagca agccatagat ttgtatcttc | 2340 |
| tgacccggat | gatgccgatg | atgatcctgg ttcttatttc attagtgctg tctgctggaa | 2400 |
| gagtgatagc | cctacgatgt | taactgctaa cagtcagggg accataaaag ttcttgtact | 2460 |
| tgctccttga | tgttatggag | ggcgttcaag aggttcacag tactgtccag ttgttccctt | 2520 |
| tcgtgtcatt | atattccccc | aaaattggga acgggggcat aattgatctc cggttaggga | 2580 |
| atgaagtttt | gcagatggtc | agctgacgta g | 2611 |

<210> SEQ ID NO 19
<211> LENGTH: 2332
<212> TYPE: DNA
<213> ORGANISM: Arabidopsis thaliana

<400> SEQUENCE: 19

| | | | |
|---|---|---|---|
| caaaaaccaa | aatcacaatc | gaagaaatct tttgaaagca aaatggaaga gatttcgacg | 60 |
| gatccggttg | ttccagcggt | gaaacctgac ccgagaacat cttcagttgg tgaaggtgct | 120 |
| aatcgtcatg | aaaatgacga | cggaggaagc ggcggttctg agattggagc accggatctg | 180 |
| gataaagact | tgctttgtcc | gatttgtatg cagattatta agatgctttt cctcacggct | 240 |
| tgtggtcata | gttctgctca | tatgtgtatc atcacacatc ttaggaacaa gagtgattgt | 300 |
| ccctgttgta | gccaacacct | caccaataat cagctttacc ctaatttctt gctcgataag | 360 |
| ctattgaaga | aaacttcagc | tcggcatgtg tcaaaaactg catcgccctt ggatcagttt | 420 |
| cgggaagcac | tacaaagggg | ttgtgatgtg tcaattaagg aggttgataa tcttctgaca | 480 |
| cttcttgcgg | aaaggaagag | aaaaatgaa caggaagaag ctgagaggaa catgcagata | 540 |
| cttttggact | ttttgcattg | tctaaggaag caaaaagttg atgaactaaa tgaggtgcaa | 600 |
| actgatctcc | agtatattaa | agaagatata atgccgttg agagacatag aatagattta | 660 |
| taccgagcta | gggacagata | ttctgtaaag ttgcggatgc tcggagactg atccaagcac | 720 |
| aagaaatgca | tggccacatg | agaagaacca gattggtttc aactccaatt ctctcagcat | 780 |
| aagaggagga | aattttgtag | gcaattatca aaacaaaaag gtagagggga aggcacaagg | 840 |
| aagctctcat | gggctaccaa | agaaggatgc gctgagtggg tcagattcgc aaagtttgaa | 900 |
| tcagtcaact | gtctcaattg | ctagaaagaa acggattcat gctcagttca atgatttaca | 960 |
| agaatgttac | ctccaaaagc | ggcgtcagtt ggcagaccaa ccaaatagta aacaagaaaa | 1020 |
| tgataagagt | gtagtacgga | gggaaggcta tagcaacggc cttgcagatt ttcaatctgt | 1080 |
| gttgactacc | ttcactcgct | acagtcgtct aagagttata gcagaaatcc ggcatgggga | 1140 |
| tatatttcat | tcagccaaca | ttgtatcaag catagagttt gatcgtgatg atgagctgtt | 1200 |
| tgccactgct | ggtgtttcta | gatgtataaa ggttttgac ttctcttcgt ttgtaaatga | 1260 |
| accagcagat | atgcagtgtc | cgattgtgga gatgtcaact cggtctaaac ttagttgctt | 1320 |
| gagttggaat | aagcatgaaa | aaaatcacat agcaagcagt gattatgaag gaatagtaac | 1380 |
| agtgtgggat | gtaactacta | ggcagagtcg gatggagtat gaagagcacg aaaaacgtgc | 1440 |

```
ctggagtgtt gacttttcac gaacagaacc atcaatgctt gtatctggta gtgacgactg    1500
caaggttaaa gtttggtgca cgaggcagga agcaagtgtg attaatattg atatgaaagc    1560
aaacatatgt tgtgtcaagt acaatcctgg ctcaagcaac tacattgcgg tcggatcagc    1620
tgatcatcac atccattatt acgatctaag aaacataagc caaccacttc atgtcttcag    1680
tggacacaag aaagcagttt cctatgttaa attttttgtcc aacaacgagc tcgcttctgc    1740
gtccacagat agcacactac gcttatggga tgtcaaagac aacttgccag ttcgaacatt    1800
cagaggacat actaacgaga gaactttgt gggtctcaca gtgaacagcg agtatctcgc     1860
ctgtggaagc gagacaaacg aagtatatgt atatcacaag gaaatcacga gacccgtgac    1920
atcgcacaga tttggatcgc cagacatgga cgatgcagag aagaggcag gttcctactt    1980 tattagtgcg gtttgctgga agagtgatag tcccacgatg ttgactgcga atagtcaagg    2040
aaccatcaaa gttctggtac tcgctgcgtg attctagtag acattacaaa agatcttata    2100
gcttcgtgaa tcaataaaaa caaatttgcc gtctatgttc tttagtggga gttacatata    2160
gagagagaac aatttattaa agtagggtt catcatttgg aaagcaactt tgtattatta    2220
tgcttgcctt ggaacactcc tcaagaagaa tttgtatcag tgatgtagat atgtcttacg    2280
gtttcttagc ttctacttta tataattaaa tgttagaatc aaaaaaaaaa aa          2332
```

<210> SEQ ID NO 20
<211> LENGTH: 2434
<212> TYPE: DNA
<213> ORGANISM: Oryza sativa

<400> SEQUENCE: 20

```
ttattcacgc ccagtcgccg cctccaccgc cgccgcctgc tcgactcacc accgcagggc     60
ggcctcctcc tgccgcatgg gtgactcgac ggtggccggc gcgctggtgc catcggtgcc    120
gaagcaggag caggcgccgt cggggacg gtccacggcg gcgttggcgg tggcggggga    180 ggggggaggag gatgcggggg cgcgcgcctc cgcgggggggc aacggggagg ccgcggccga    240 cagggaccc ctctgcccga tctgcatggc ggtcatcaag gacgccttcc tcaccgcctg    300
cggccacagc ttctgctaca tgtgcatcgt cacgcatctc agccacaaga gcgactgccc    360
ctgctgcggc aactacctca ccaaggcgca gctctacccc aacttcctcc tcgacaaggt    420
cttgaagaaa atgtcagctc gccaaattgc gaagacagca tcaccgatag accaatttcg    480
atatgcactg caacagggaa acgatatggc ggttaaagaa ctagatagtc ttatgacttt    540
gatcgcggag aagaagcggc atatggaaca gcaagagtca gaaacaaata tgcaaatatt    600
gctggtcttc ttgcattgcc tcagaaagca aagttggaa gagctgaatg agattcaaac    660
tgacctacag tacatcaaag aagatataag tgctgtggag agacataggt tagaattata    720
tcgaacaaaa gaaaggtact caatgaagct ccgcatgctt ttggatgaac ctgctgcatc    780
aaagatgtgg ccttcaccta tggataaacc tagtggtctc tttcttccca actctcgggg    840
accacttagt acatcaaatc caggggggttt acagaataag aagcttgact tgaaaggtca    900
aattagtcat caaggatttc aaaggagaga tgttctcact tgctcggatc ctccctagtgc    960 ccctattcaa tcaggcaacg ttattgctcg gaagaggcga gttcaagctc agtttaacga   1020
gcttcaagaa tactatcttc aaagacggcg taccggagca caatcacgta ggctggagga   1080
aagagacata gtaacaataa ataaagaagg ttatcatgca ggacttgagg attttccagtc   1140 tgtgctaaca acattcacac gatatagtcg cttgcgtgta attgcggagc taagacatgg   1200
```

-continued

```
agatctgttt cactctgcaa atatcgtatc aagtatcgaa tttgaccgtg atgatgagct   1260
atttgctact gctggagtct caaagcgcat caaagtcttc gagttttcta cagttgttaa   1320
tgaaccatca gatgtgcatt gtccagttgt tgaaatggct actagatcta aactcagctg   1380
ccttagctgg aacaagtact caaaaaatgt tatagcaagc agcgactatg agggtatagt   1440
aactgtttgg gatgtccaaa cccgccagag tgtgatggag tatgaagaac atgaaaagag   1500
agcatggagt gttgattttt ctcgaacaga accctcgatg ctagtatctg ggagtgatga   1560
ttgcaaggtc aaagtgtggt gcacaaagca agaagcaagt gccatcaata ttgatatgaa   1620
ggccaatatt tgctctgtca aatataatcc tgggtcgagc cactatgttg cagtgggttc   1680
tgctgatcac catattcatt attttgattt gcgaaatcca agtgcgcctg tccatgtttt   1740
tggtgggcac aagaaagctg tttcttatgt gaagttcctg tccaccaatg agcttgcgtc   1800
tgcatcaact gatagcacat acggttatg ggatgtcaaa gaaaattgcc ctgtaaggac   1860
attcagaggg cacaagaatg aaaagaactt tgttgggctg tctgtaaata acgagtacat   1920
tgcctgcggg agtgaaacga atgaggtttt tgtttaccac aaggctatct caaaacctgc   1980
tgccaaccac agatttgtat catctgatct cgatgatgca gatgatgatc ctggctctta   2040
ttttattagc gcagtctgct ggaagagcga tagccctacc atgttaactg ctaacagtca   2100
gggcaccatt aaagttcttg tacttgctcc ttgatgaaat cagtggtttt catgagatcc   2160
ctagatagct tgtatatttg atgtatacag ttgtttcctt ttcgtgccat tataccccaa   2220
atggagtgg aggtattact gatctccaac atagggcgca aagttttgaa ggtaatcagc   2280
tgacataggg tttcgagggc tcgaaatgtg catagtccag aattctcatg tataggttta   2340
aagcagtcaa gtaattgatt atacatatgt aacgtgagaa ttgagaaatg aacatcaaat   2400
aagcttgttt ggttgcataa aaaaaaaaaa aaaa                               2434
```

<210> SEQ ID NO 21
<211> LENGTH: 685
<212> TYPE: PRT
<213> ORGANISM: Oryza sativa

<400> SEQUENCE: 21

```
Met Gly Asp Ser Thr Val Ala Gly Ala Leu Val Pro Ser Val Pro Lys
1               5                   10                  15

Gln Glu Gln Ala Pro Ser Gly Asp Ala Ser Thr Ala Ala Leu Ala Val
            20                  25                  30

Ala Gly Glu Gly Glu Glu Asp Ala Gly Ala Arg Ala Ser Ala Gly Gly
        35                  40                  45

Asn Gly Glu Ala Ala Ala Asp Arg Asp Leu Leu Cys Pro Ile Cys Met
    50                  55                  60

Ala Val Ile Lys Asp Ala Phe Leu Thr Ala Cys Gly His Ser Phe Cys
65                  70                  75                  80

Tyr Met Cys Ile Val Thr His Leu Ser His Lys Ser Asp Cys Pro Cys
                85                  90                  95

Cys Gly Asn Tyr Leu Thr Lys Ala Gln Leu Tyr Pro Asn Phe Leu Leu
            100                 105                 110

Asp Lys Val Leu Lys Met Ser Ala Arg Gln Ile Ala Lys Thr Ala
        115                 120                 125

Ser Pro Ile Asp Gln Phe Arg Tyr Ala Leu Gln Gln Gly Asn Asp Met
    130                 135                 140

Ala Val Lys Glu Leu Asp Ser Leu Met Thr Leu Ile Ala Glu Lys Lys
145                 150                 155                 160
```

-continued

Arg His Met Glu Gln Gln Ser Glu Thr Asn Met Gln Ile Leu Leu
                165                 170                 175

Val Phe Leu His Cys Leu Arg Lys Gln Lys Leu Glu Glu Leu Asn Glu
            180                 185                 190

Ile Gln Thr Asp Leu Gln Tyr Ile Lys Glu Asp Ile Ser Ala Val Glu
        195                 200                 205

Arg His Arg Leu Glu Leu Tyr Arg Thr Lys Glu Arg Tyr Ser Met Lys
    210                 215                 220

Leu Arg Met Leu Leu Asp Glu Pro Ala Ala Ser Lys Met Trp Pro Ser
225                 230                 235                 240

Pro Met Asp Lys Pro Ser Gly Leu Phe Leu Pro Asn Ser Arg Gly Pro
                245                 250                 255

Leu Ser Thr Ser Asn Pro Gly Gly Leu Gln Asn Lys Lys Leu Asp Leu
            260                 265                 270

Lys Gly Gln Ile Ser His Gln Gly Phe Gln Arg Arg Asp Val Leu Thr
        275                 280                 285

Cys Ser Asp Pro Pro Ser Ala Pro Ile Gln Ser Gly Asn Val Ile Ala
    290                 295                 300

Arg Lys Arg Arg Val Gln Ala Gln Phe Asn Glu Leu Gln Glu Tyr Tyr
305                 310                 315                 320

Leu Gln Arg Arg Arg Thr Gly Ala Gln Ser Arg Arg Leu Glu Glu Arg
                325                 330                 335

Asp Ile Val Thr Ile Asn Lys Glu Gly Tyr His Ala Gly Leu Glu Asp
            340                 345                 350

Phe Gln Ser Val Leu Thr Thr Phe Thr Arg Tyr Ser Arg Leu Arg Val
        355                 360                 365

Ile Ala Glu Leu Arg His Gly Asp Leu Phe His Ser Ala Asn Ile Val
    370                 375                 380

Ser Ser Ile Glu Phe Asp Arg Asp Asp Glu Leu Phe Ala Thr Ala Gly
385                 390                 395                 400

Val Ser Lys Arg Ile Lys Val Phe Glu Phe Ser Thr Val Val Asn Glu
                405                 410                 415

Pro Ser Asp Val His Cys Pro Val Val Glu Met Ala Thr Arg Ser Lys
            420                 425                 430

Leu Ser Cys Leu Ser Trp Asn Lys Tyr Ser Lys Asn Val Ile Ala Ser
        435                 440                 445

Ser Asp Tyr Glu Gly Ile Val Thr Val Trp Asp Val Gln Thr Arg Gln
    450                 455                 460

Ser Val Met Glu Tyr Glu Glu His Glu Lys Arg Ala Trp Ser Val Asp
465                 470                 475                 480

Phe Ser Arg Thr Glu Pro Ser Met Leu Val Ser Gly Ser Asp Asp Cys
                485                 490                 495

Lys Val Lys Val Trp Cys Thr Lys Gln Glu Ala Ser Ala Ile Asn Ile
            500                 505                 510

Asp Met Lys Ala Asn Ile Cys Ser Val Lys Tyr Asn Pro Gly Ser Ser
        515                 520                 525

His Tyr Val Ala Val Gly Ser Ala Asp His His Ile His Tyr Phe Asp
    530                 535                 540

Leu Arg Asn Pro Ser Ala Pro Val His Val Phe Gly Gly His Lys Lys
545                 550                 555                 560

Ala Val Ser Tyr Val Lys Phe Leu Ser Thr Asn Glu Leu Ala Ser Ala
                565                 570                 575

```
Ser Thr Asp Ser Thr Leu Arg Leu Trp Asp Val Lys Glu Asn Cys Pro
            580                 585                 590

Val Arg Thr Phe Arg Gly His Lys Asn Glu Lys Asn Phe Val Gly Leu
            595                 600                 605

Ser Val Asn Asn Glu Tyr Ile Ala Cys Gly Ser Glu Thr Asn Glu Val
            610                 615                 620

Phe Val Tyr His Lys Ala Ile Ser Lys Pro Ala Ala Asn His Arg Phe
625                 630                 635                 640

Val Ser Ser Asp Leu Asp Asp Ala Asp Asp Pro Gly Ser Tyr Phe
            645                 650                 655

Ile Ser Ala Val Cys Trp Lys Ser Asp Ser Pro Thr Met Leu Thr Ala
            660                 665                 670

Asn Ser Gln Gly Thr Ile Lys Val Leu Val Leu Ala Pro
            675                 680                 685

<210> SEQ ID NO 22
<211> LENGTH: 693
<212> TYPE: PRT
<213> ORGANISM: Zea mays

<400> SEQUENCE: 22

Met Gly Asp Ser Ser Val Ala Gly Ala Leu Val Pro Ser Val Pro Lys
1               5                   10                  15

Pro Glu Pro Ala Pro Ser Gly Asp Thr Ser Ala Ala Ala Ala Ala Thr
            20                  25                  30

Thr Ala Ala Leu Ala Met Pro Glu Glu Ala Gly Met Arg Ala Ala Ser
            35                  40                  45

Ala Ser Pro Gln Gly Pro Ala Glu Glu Gly Glu Gly Pro Ala Asp Arg
        50                  55                  60

Asp Leu Leu Cys Pro Ile Cys Met Ala Val Ile Lys Asp Ala Phe Leu
65                  70                  75                  80

Thr Ala Cys Gly His Ser Phe Cys Tyr Met Cys Ile Val Thr His Leu
                85                  90                  95

Ser Asn Lys Ser Asp Cys Pro Cys Cys Gly His Tyr Leu Thr Lys Ala
            100                 105                 110

Gln Leu Tyr Pro Asn Phe Leu Leu Asp Lys Val Leu Lys Lys Ile Ser
            115                 120                 125

Ala Gln Gln Ile Ala Lys Thr Ala Ser Pro Ile Asp Gln Phe Arg Cys
        130                 135                 140

Ala Leu Gln Gln Gly Asn Glu Met Gly Val Lys Glu Leu Asp Ser Leu
145                 150                 155                 160

Met Thr Leu Ile Ala Glu Lys Lys Arg Gln Met Glu Gln Gln Glu Ser
                165                 170                 175

Glu Thr Asn Met Gln Ile Leu Leu Val Phe Leu His Cys Leu Arg Lys
            180                 185                 190

Gln Lys Leu Glu Glu Leu Asn Glu Ile Gln Thr Asp Leu Gln Tyr Ile
            195                 200                 205

Lys Glu Asp Ile Ser Ser Val Glu Arg His Arg Ala Glu Leu Tyr Arg
        210                 215                 220

Thr Lys Glu Arg Tyr Ser Met Lys Leu Arg Met Leu Leu Asp Glu Pro
225                 230                 235                 240

Thr Ala Gln Lys Met Trp Pro Ser Pro Ile Asp Lys Ala Ser Cys Arg
                245                 250                 255

Phe Leu Pro Asn Ser Arg Thr Pro Leu Ser Gly Ser Cys Pro Gly Thr
            260                 265                 270
```

```
Leu Gln Asn Lys Lys Leu Asp Leu Lys Ala Gln Val Ser His Gln Gly
            275                 280                 285

Phe Gln Arg Arg Asp Ala Leu Thr Ser Ser Asp Pro Pro Asn Ser Pro
    290                 295                 300

Ile Gln Ser Gly Asn Val Ile Ala Arg Lys Arg Val Gln Ala Gln
305                 310                 315                 320

Phe Asn Glu Leu Gln Glu Tyr Tyr Leu Gln Arg Arg Thr Gly Ala
                325                 330                 335

Gln Ala Arg Arg Gln Glu Arg Asp Ile Val Ala Met Asn Arg Glu
            340                 345                 350

Gly Tyr His Ala Gly Leu Gln Asp Phe Gln Ser Val Leu Thr Thr Phe
                355                 360                 365

Thr Arg Tyr Ser Arg Leu Arg Val Ile Ala Glu Leu Arg His Gly Asp
    370                 375                 380

Leu Phe His Ser Ala Asn Ile Val Ser Ser Ile Glu Phe Asp Arg Asp
385                 390                 395                 400

Asp Glu Leu Phe Ala Thr Ala Gly Val Ser Lys Arg Ile Lys Val Phe
                405                 410                 415

Glu Phe Ser Thr Val Val Asn Glu Pro Ser Asp Val His Cys Pro Val
            420                 425                 430

Val Glu Met Ala Thr Arg Ser Lys Leu Ser Cys Leu Ser Trp Asn Lys
        435                 440                 445

Tyr Ser Lys Asn Ile Ile Ala Ser Ser Asp Tyr Glu Gly Ile Val Thr
    450                 455                 460

Val Trp Asp Val Gln Thr Arg Gln Ser Val Met Glu Tyr Glu Glu His
465                 470                 475                 480

Glu Lys Arg Ala Trp Ser Val Asp Phe Ser Arg Thr Asp Ser Ser Met
                485                 490                 495

Leu Val Ser Gly Ser Asp Asp Cys Lys Val Lys Val Trp Cys Thr Asn
            500                 505                 510

Gln Glu Ala Ser Val Ile Asn Ile Asp Met Lys Ala Asn Ile Cys Ser
        515                 520                 525

Val Lys Tyr Asn Pro Gly Ser Ser Phe Tyr Val Ala Val Gly Ser Ala
    530                 535                 540

Asp His His Ile His Tyr Phe Asp Leu Arg Asn Pro Ser Ser Pro Val
545                 550                 555                 560

His Ile Phe Gly Gly His Lys Lys Ala Val Ser Tyr Val Lys Phe Leu
                565                 570                 575

Ser Asn Asn Glu Leu Ala Ser Ala Ser Thr Asp Ser Thr Leu Arg Leu
            580                 585                 590

Trp Asp Val Lys Asp Asn Cys Pro Val Arg Thr Phe Arg Gly His Lys
        595                 600                 605

Asn Glu Lys Asn Phe Val Gly Leu Ser Val Asn Asn Glu Tyr Ile Ala
    610                 615                 620

Cys Gly Ser Glu Thr Asn Glu Val Phe Val Tyr His Lys Ala Ile Ser
625                 630                 635                 640

Lys Pro Ala Ala Ser His Arg Phe Val Ser Ser Asp Pro Asp Asp Ala
                645                 650                 655

Asp Asp Asp Pro Gly Ser Tyr Phe Ile Ser Ala Val Cys Trp Lys Ser
            660                 665                 670

Asp Ser Pro Thr Met Leu Thr Ala Asn Ser Gln Gly Thr Ile Lys Val
        675                 680                 685
```

Leu Val Leu Ala Pro
    690

<210> SEQ ID NO 23
<211> LENGTH: 677
<212> TYPE: PRT
<213> ORGANISM: Ipomoea nil

<400> SEQUENCE: 23

Met Gly Glu Arg Glu Gly Glu Cys Gly Glu Ser Ser Met Val Gly
1               5                   10                  15

Ala Val Val Pro Ala Val Lys Ala Arg Asn Ala Glu Glu Pro Ser Ile
            20                  25                  30

Ser His Arg Asp Glu Ala Thr Pro Ser Gly Met Glu Pro Glu Leu Asp
        35                  40                  45

Arg Glu Leu Leu Cys Pro Ile Cys Met Gln Ile Ile Lys Asp Ala Phe
    50                  55                  60

Leu Thr Ser Cys Gly His Ser Phe Cys Tyr Met Cys Ile Val Thr His
65                  70                  75                  80

Leu His Asn Lys Ser Asp Cys Pro Cys Cys Ser His Tyr Leu Thr Thr
                85                  90                  95

Ala Gln Leu Tyr Pro Asn Phe Leu Leu Asp Lys Leu Leu Lys Lys Thr
            100                 105                 110

Ser Ala His Gln Ile Ser Lys Thr Ala Ser Pro Val Glu Gln Phe Arg
        115                 120                 125

His Ser Ile Glu Gln Gly Arg Glu Val Ser Ile Lys Glu Leu Asp Val
    130                 135                 140

Leu Leu Thr Ile Leu Ala Glu Lys Lys Arg Lys Leu Glu Gln Glu Glu
145                 150                 155                 160

Ala Glu Arg Asn Met Gln Ile Leu Leu Glu Phe Leu His Met Leu Lys
                165                 170                 175

Lys Lys Lys Val Asp Glu Leu Asn Glu Val Gln Asn Asp Leu Gln Tyr
            180                 185                 190

Ile Lys Glu Asp Ile Asn Ala Val Glu Arg His Arg Ile Asp Leu Tyr
        195                 200                 205

Arg Ala Arg Asp Arg Tyr Ser Met Lys Leu Arg Met Leu Ala Asp Asp
    210                 215                 220

Pro Leu Gly Ser Lys Ser Arg Ser Ser Ser Val Asp Arg Asn Thr Ile
225                 230                 235                 240

Gly Leu Phe Pro Ser Ser Arg Ser Ala His Gly Gly Leu Ala Ser Gly
                245                 250                 255

Asn Leu Met Tyr Lys Lys Asn Asp Gly Gly Ser Gln Arg Lys Asp Val
            260                 265                 270

Ser Val Thr Glu Leu Ser Leu Asn Gly Ser Asp Ser Gln His Met Asn
        275                 280                 285

Gln Ser Gly Leu Ala Val Met Arg Lys Lys Arg Val His Ala Gln Phe
    290                 295                 300

Asn Asp Leu Gln Glu Cys Tyr Leu Gln Lys Arg Arg Gln Leu Ala Asn
305                 310                 315                 320

Gln Leu Gln Asn Lys Glu Glu Asp Gln Asn Val Thr Arg Arg Glu
                325                 330                 335

Gly Tyr Ser Ala Gly Leu Ser Glu Phe Gln Ser Val Leu Ser Thr Phe
            340                 345                 350

Thr Arg Tyr Ser Arg Leu Arg Val Ile Ala Glu Leu Arg His Gly Asp
        355                 360                 365

-continued

```
Ile Phe His Ser Ala Asn Ile Val Ser Ser Ile Glu Phe Asp Arg Asp
    370                 375                 380
Asp Glu Leu Phe Ala Thr Ala Gly Val Ser Arg Arg Ile Lys Val Phe
385                 390                 395                 400
Asp Phe Ser Ser Val Val Asn Glu Pro Ala Asp Ala His Cys Pro Val
                405                 410                 415
Val Glu Met Ser Thr Arg Ser Lys Leu Ser Cys Leu Ser Trp Asn Lys
            420                 425                 430
Tyr Thr Lys Asn His Ile Ala Ser Ser Asp Tyr Asp Gly Ile Val Thr
        435                 440                 445
Val Trp Asp Val Thr Thr Arg Gln Ser Val Met Glu Tyr Glu Glu His
    450                 455                 460
Glu Lys Arg Ala Trp Ser Val Asp Phe Ser Arg Thr Asp Pro Ser Met
465                 470                 475                 480
Leu Val Ser Gly Ser Asp Asp Cys Lys Val Lys Val Trp Cys Thr Lys
                485                 490                 495
Gln Glu Ala Ser Ala Leu Asn Ile Asp Met Lys Ala Asn Ile Cys Cys
            500                 505                 510
Val Lys Tyr Asn Pro Gly Ser Ser Phe His Val Ala Val Gly Ser Ala
        515                 520                 525
Asp His His Ile His Tyr Tyr Asp Leu Arg Asn Thr Ser Ala Pro Leu
    530                 535                 540
His Ile Phe Ser Gly His Lys Lys Ala Val Ser Tyr Val Lys Phe Leu
545                 550                 555                 560
Ser Ser His Glu Leu Ala Ser Ala Ser Thr Asp Ser Thr Leu Arg Leu
                565                 570                 575
Trp Asp Val Lys Asp Asn Ser Pro Val Arg Val Phe Arg Gly His Thr
            580                 585                 590
Asn Glu Lys Asn Phe Val Gly Leu Ser Val Ser Asn Glu Phe Ile Ser
        595                 600                 605
Cys Gly Ser Glu Thr Asn Glu Val Phe Val Tyr His Lys Ala Ile Ser
    610                 615                 620
Lys Pro Val Thr Trp His Arg Phe Gly Ser Pro Asp Val Asp Glu Ala
625                 630                 635                 640
Asp Glu Asp Val Thr Ser Phe Phe Ile Ser Ala Val Cys Trp Lys Ser
                645                 650                 655
Asp Ser Pro Thr Met Leu Ala Ala Asn Ser Gln Gly Thr Ile Lys Val
            660                 665                 670
Leu Val Leu Ala Ala
        675

<210> SEQ ID NO 24
<211> LENGTH: 677
<212> TYPE: PRT
<213> ORGANISM: Lycopersicon esculentum

<400> SEQUENCE: 24

Met Val Glu Ser Val Gly Gly Val Pro Ala Val Lys Gly Glu
1               5                   10                  15
Val Met Arg Arg Met Gly Asp Lys Glu Gly Gly Ser Val Thr Leu
            20                  25                  30
Arg Asp Glu Glu Val Gly Thr Val Thr Glu Trp Glu Leu Asp Arg Glu
    35                  40                  45
Leu Leu Cys Pro Ile Cys Met Gln Ile Ile Lys Asp Ala Phe Leu Thr
```

```
                50              55              60
Ala Cys Gly His Ser Phe Cys Tyr Met Cys Ile Val Thr His Leu His
 65              70              75              80

Asn Lys Ser Asp Cys Pro Cys Ser His Tyr Leu Thr Thr Ser Gln
                 85              90              95

Leu Tyr Pro Asn Phe Leu Leu Asp Lys Leu Leu Lys Lys Thr Ser Ala
                100             105             110

Arg Gln Ile Ser Lys Thr Ala Ser Pro Val Glu Gln Phe Arg His Ser
                115             120             125

Leu Glu Gln Gly Ser Glu Val Ser Ile Lys Glu Leu Asp Ala Leu Leu
    130             135             140

Leu Met Leu Ser Glu Lys Lys Arg Lys Leu Glu Gln Glu Glu Ala Glu
145             150             155             160

Arg Asn Met Gln Ile Leu Leu Asp Phe Leu Gln Met Leu Arg Lys Gln
                165             170             175

Lys Val Asp Glu Leu Asn Glu Val Gln His Asp Leu Gln Tyr Ile Lys
                180             185             190

Glu Asp Leu Asn Ser Val Glu Arg His Arg Ile Asp Leu Tyr Arg Ala
            195             200             205

Arg Asp Arg Tyr Ser Met Lys Leu Arg Met Leu Ala Asp Asp Pro Ile
210             215             220

Gly Lys Lys Pro Trp Ser Ser Thr Asp Arg Asn Phe Gly Gly Leu
225             230             235             240

Phe Ser Thr Ser Gln Asn Ala Pro Gly Gly Leu Pro Thr Gly Asn Leu
                245             250             255

Thr Phe Lys Lys Val Asp Ser Lys Ala Gln Ile Ser Ser Pro Gly Pro
                260             265             270

Gln Arg Lys Asp Thr Ser Ile Ser Glu Leu Asn Ser Gln His Met Ser
            275             280             285

Gln Ser Gly Leu Ala Val Val Arg Lys Lys Arg Val Asn Ala Gln Phe
    290             295             300

Asn Asp Leu Gln Glu Cys Tyr Leu Gln Lys Arg Arg Gln Leu Ala Asn
305             310             315             320

Lys Ser Arg Val Lys Glu Lys Asp Ala Asp Val Val Gln Arg Glu
                325             330             335

Gly Tyr Ser Glu Gly Leu Ala Asp Phe Gln Ser Val Leu Ser Thr Phe
                340             345             350

Thr Arg Tyr Ser Arg Leu Arg Val Ile Ala Glu Leu Arg His Gly Asp
            355             360             365

Leu Phe His Ser Ala Asn Ile Val Ser Ser Ile Glu Phe Asp Arg Asp
    370             375             380

Asp Glu Leu Phe Ala Thr Ala Gly Val Ser Arg Arg Ile Lys Val Phe
385             390             395             400

Asp Phe Ser Ser Val Val Asn Glu Pro Ala Asp Ala His Cys Pro Val
                405             410             415

Val Glu Met Ser Thr Arg Ser Lys Leu Ser Cys Leu Ser Trp Asn Lys
                420             425             430

Tyr Thr Lys Asn His Ile Ala Ser Ser Asp Tyr Asp Gly Ile Val Thr
            435             440             445

Val Trp Asp Val Thr Thr Arg Gln Ser Val Met Glu Tyr Glu Glu His
    450             455             460

Glu Lys Arg Ala Trp Ser Val Asp Phe Ser Arg Thr Glu Pro Ser Met
465             470             475             480
```

```
Leu Val Ser Gly Ser Asp Asp Cys Lys Val Lys Val Trp Cys Thr Lys
                485                 490                 495

Gln Glu Ala Ser Val Leu Asn Ile Asp Met Lys Ala Asn Ile Cys Cys
            500                 505                 510

Val Lys Tyr Asn Pro Gly Ser Ser Val His Ile Ala Val Gly Ser Ala
        515                 520                 525

Asp His His Ile His Tyr Tyr Asp Leu Arg Asn Thr Ser Gln Pro Val
    530                 535                 540

His Ile Phe Ser Gly His Arg Lys Ala Val Ser Tyr Val Lys Phe Leu
545                 550                 555                 560

Ser Asn Asn Glu Leu Ala Ser Ala Ser Thr Asp Ser Thr Leu Arg Leu
                565                 570                 575

Trp Asp Val Lys Asp Asn Leu Pro Val Arg Thr Leu Arg Gly His Thr
            580                 585                 590

Asn Glu Lys Asn Phe Val Gly Leu Ser Val Asn Glu Phe Leu Ser
        595                 600                 605

Cys Gly Ser Glu Thr Asn Glu Val Phe Val Tyr His Lys Ala Ile Ser
    610                 615                 620

Lys Pro Val Thr Trp His Arg Phe Gly Ser Pro Asp Ile Asp Glu Ala
625                 630                 635                 640

Asp Glu Asp Ala Gly Ser Tyr Phe Ile Ser Ala Val Cys Trp Lys Ser
                645                 650                 655

Asp Ser Pro Thr Met Leu Ala Ala Asn Ser Gln Gly Thr Ile Lys Val
            660                 665                 670

Leu Val Leu Ala Ala
        675

<210> SEQ ID NO 25
<211> LENGTH: 675
<212> TYPE: PRT
<213> ORGANISM: Arabidopsis thaliana

<400> SEQUENCE: 25

Met Glu Glu Ile Ser Thr Asp Pro Val Val Pro Ala Val Lys Pro Asp
1               5                   10                  15

Pro Arg Thr Ser Ser Val Gly Glu Gly Ala Asn Arg His Glu Asn Asp
            20                  25                  30

Asp Gly Gly Ser Gly Gly Ser Glu Ile Gly Ala Pro Asp Leu Asp Lys
        35                  40                  45

Asp Leu Leu Cys Pro Ile Cys Met Gln Ile Ile Lys Asp Ala Phe Leu
    50                  55                  60

Thr Ala Cys Gly His Ser Phe Cys Tyr Met Cys Ile Ile Thr His Leu
65                  70                  75                  80

Arg Asn Lys Ser Asp Cys Pro Cys Cys Ser Gln His Leu Thr Asn Asn
                85                  90                  95

Gln Leu Tyr Pro Asn Phe Leu Asp Lys Leu Leu Lys Lys Thr Ser
            100                 105                 110

Ala Arg His Val Ser Lys Thr Ala Ser Pro Leu Asp Gln Phe Arg Glu
        115                 120                 125

Ala Leu Gln Arg Gly Cys Asp Val Ser Ile Lys Glu Val Asp Asn Leu
    130                 135                 140

Leu Thr Leu Leu Ala Glu Arg Lys Arg Lys Met Glu Gln Glu Glu Ala
145                 150                 155                 160

Glu Arg Asn Met Gln Ile Leu Leu Asp Phe Leu His Cys Leu Arg Lys
```

-continued

```
            165                 170                 175
Gln Lys Val Asp Glu Leu Asn Glu Val Gln Thr Asp Leu Gln Tyr Ile
            180                 185                 190

Lys Glu Asp Ile Asn Ala Val Glu Arg His Arg Ile Asp Leu Tyr Arg
            195                 200                 205

Ala Arg Asp Arg Tyr Ser Val Lys Leu Arg Met Leu Gly Asp Asp Pro
210                 215                 220

Ser Thr Arg Asn Ala Trp Pro His Glu Lys Asn Gln Ile Gly Phe Asn
225                 230                 235                 240

Ser Asn Ser Leu Ser Ile Arg Gly Gly Asn Phe Val Gly Asn Tyr Gln
            245                 250                 255

Asn Lys Lys Val Glu Gly Lys Ala Gln Gly Ser Ser His Gly Leu Pro
            260                 265                 270

Lys Lys Asp Ala Leu Ser Gly Ser Asp Ser Gln Ser Leu Asn Gln Ser
            275                 280                 285

Thr Val Ser Met Ala Arg Lys Lys Arg Ile His Ala Gln Phe Asn Asp
            290                 295                 300

Leu Gln Glu Cys Tyr Leu Gln Lys Arg Gln Leu Ala Asp Gln Pro
305                 310                 315                 320

Asn Ser Lys Gln Glu Asn Asp Lys Ser Val Arg Arg Glu Gly Tyr
            325                 330                 335

Ser Asn Gly Leu Ala Asp Phe Gln Ser Val Leu Thr Thr Phe Thr Arg
            340                 345                 350

Tyr Ser Arg Leu Arg Val Ile Ala Glu Ile Arg His Gly Asp Ile Phe
            355                 360                 365

His Ser Ala Asn Ile Val Ser Ser Ile Glu Phe Asp Arg Asp Asp Glu
            370                 375                 380

Leu Phe Ala Thr Ala Gly Val Ser Arg Cys Ile Lys Val Phe Asp Phe
385                 390                 395                 400

Ser Ser Val Val Asn Glu Pro Ala Asp Met Gln Cys Pro Ile Val Glu
            405                 410                 415

Met Ser Thr Arg Ser Lys Leu Ser Cys Leu Ser Trp Asn Lys His Glu
            420                 425                 430

Lys Asn His Ile Ala Ser Ser Asp Tyr Glu Gly Ile Val Thr Val Trp
            435                 440                 445

Asp Val Thr Thr Arg Gln Ser Leu Met Glu Tyr Glu Glu His Glu Lys
            450                 455                 460

Arg Ala Trp Ser Val Asp Phe Ser Arg Thr Glu Pro Ser Met Leu Val
465                 470                 475                 480

Ser Gly Ser Asp Asp Cys Lys Val Lys Val Trp Cys Thr Arg Gln Glu
            485                 490                 495

Ala Ser Val Ile Asn Ile Asp Met Lys Ala Asn Ile Cys Cys Val Lys
            500                 505                 510

Tyr Asn Pro Gly Ser Ser Asn Tyr Ile Ala Val Gly Ser Ala Asp His
            515                 520                 525

His Ile His Tyr Tyr Asp Leu Arg Asn Ile Ser Gln Pro Leu His Val
            530                 535                 540

Phe Ser Gly His Lys Lys Ala Val Ser Tyr Val Lys Phe Leu Ser Asn
545                 550                 555                 560

Asn Glu Leu Ala Ser Ala Ser Thr Asp Ser Thr Leu Arg Leu Trp Asp
            565                 570                 575

Val Lys Asp Asn Leu Pro Val Arg Thr Phe Arg Gly His Thr Asn Glu
            580                 585                 590
```

```
Lys Asn Phe Val Gly Leu Thr Val Asn Ser Glu Tyr Leu Ala Cys Gly
            595                 600                 605

Ser Glu Thr Asn Glu Val Tyr Val Tyr His Lys Glu Ile Thr Arg Pro
610                 615                 620

Val Thr Ser His Arg Phe Gly Ser Pro Asp Met Asp Asp Ala Glu Glu
625                 630                 635                 640

Glu Ala Gly Ser Tyr Phe Ile Ser Ala Val Cys Trp Lys Ser Asp Ser
                645                 650                 655

Pro Thr Met Leu Thr Ala Asn Ser Gln Gly Thr Ile Lys Val Leu Val
            660                 665                 670

Leu Ala Ala
        675

<210> SEQ ID NO 26
<211> LENGTH: 672
<212> TYPE: PRT
<213> ORGANISM: Pisum sativum

<400> SEQUENCE: 26

Met Glu Glu His Ser Val Gly Pro Leu Val Pro Ala Val Val Lys Pro
1               5                   10                  15

Glu Pro Ser Lys Asn Phe Ser Thr Asp Thr Ala Ala Gly Thr Phe
            20                  25                  30

Leu Leu Val Pro Thr Met Ser Asp Leu Asp Lys Asp Phe Leu Cys Pro
        35                  40                  45

Ile Cys Met Gln Ile Ile Lys Asp Ala Phe Leu Thr Ala Cys Gly His
50                  55                  60

Ser Phe Cys Tyr Met Cys Ile Ile Thr His Leu Arg Asn Lys Ser Asp
65                  70                  75                  80

Cys Pro Cys Cys Gly His Tyr Leu Thr Asn Ser Asn Leu Phe Pro Asn
                85                  90                  95

Phe Leu Leu Asp Lys Leu Leu Lys Lys Thr Ser Asp Arg Gln Ile Ser
            100                 105                 110

Lys Thr Ala Ser Pro Val Glu His Phe Arg Gln Ala Val Gln Lys Gly
        115                 120                 125

Cys Glu Val Thr Met Lys Glu Leu Asp Thr Leu Leu Leu Leu Leu Thr
130                 135                 140

Glu Lys Lys Arg Lys Met Glu Gln Glu Glu Ala Glu Arg Asn Met Gln
145                 150                 155                 160

Ile Leu Leu Asp Phe Leu His Cys Leu Arg Lys Gln Lys Val Asp Glu
                165                 170                 175

Leu Lys Glu Val Gln Thr Asp Leu Gln Phe Ile Lys Glu Asp Ile Gly
            180                 185                 190

Ala Val Glu Lys His Arg Met Asp Leu Tyr Arg Ala Arg Asp Arg Tyr
        195                 200                 205

Ser Val Lys Leu Arg Met Leu Asp Asp Ser Gly Gly Arg Lys Ser Arg
210                 215                 220

His Ser Ser Met Asp Leu Asn Ser Ser Gly Leu Ala Ser Ser Pro Leu
225                 230                 235                 240

Asn Leu Arg Gly Gly Leu Ser Ser Gly Ser His Thr Lys Lys Asn Asp
                245                 250                 255

Gly Lys Ser Gln Ile Ser Ser His Gly His Gly Ile Gln Arg Arg Asp
            260                 265                 270

Pro Ile Thr Gly Ser Asp Ser Gln Tyr Ile Asn Gln Ser Gly Leu Ala
```

275                 280                 285
Leu Val Arg Lys Lys Arg Val His Thr Gln Phe Asn Asp Leu Gln Glu
        290                 295                 300

Cys Tyr Leu Gln Lys Arg Arg Gln Ala Ala Asp Lys Pro His Gly Gln
305                 310                 315                 320

Gln Glu Arg Asp Thr Asn Phe Ile Ser Arg Gly Tyr Ser Cys Gly
                325                 330                 335

Leu Asp Asp Phe Gln Ser Val Leu Thr Thr Phe Thr Tyr Ser Arg
            340                 345                 350

Leu Arg Val Ile Ala Glu Ile Arg His Gly Asp Ile Phe His Ser Ala
        355                 360                 365

Asn Ile Val Ser Ser Ile Glu Phe Asp Arg Asp Asp Leu Phe Ala
370                 375                 380

Thr Ala Gly Val Ser Arg Arg Ile Lys Val Phe Asp Phe Ser Ala Val
385                 390                 395                 400

Val Asn Glu Pro Thr Asp Ala His Cys Pro Val Val Glu Met Thr Thr
                405                 410                 415

Arg Ser Lys Leu Ser Cys Leu Ser Trp Asn Lys Tyr Ala Lys Asn Gln
            420                 425                 430

Ile Ala Ser Ser Asp Tyr Glu Gly Ile Val Thr Val Trp Thr Met Thr
                435                 440                 445

Thr Arg Lys Ser Leu Met Glu Tyr Glu His Glu Lys Arg Ala Trp
450                 455                 460

Ser Val Asp Phe Ser Arg Thr Asp Pro Ser Met Leu Val Ser Gly Ser
465                 470                 475                 480

Asp Asp Cys Lys Val Lys Val Trp Cys Thr Asn Gln Glu Ala Ser Val
                485                 490                 495

Leu Asn Ile Asp Met Lys Ala Asn Ile Cys Cys Val Lys Tyr Asn Pro
            500                 505                 510

Gly Ser Gly Asn Tyr Ile Ala Val Gly Ser Ala Asp His His Ile His
        515                 520                 525

Tyr Tyr Asp Leu Arg Asn Ile Ser Arg Pro Val His Val Phe Thr Gly
        530                 535                 540

His Lys Lys Ala Val Ser Tyr Val Lys Phe Leu Ser Asn Asp Glu Leu
545                 550                 555                 560

Ala Ser Ala Ser Thr Asp Ser Thr Leu Arg Leu Trp Asp Val Lys Gln
                565                 570                 575

Asn Leu Pro Val Arg Thr Phe Arg Gly His Ala Asn Glu Lys Asn Phe
            580                 585                 590

Val Gly Leu Thr Val Arg Ser Glu Tyr Ile Ala Cys Gly Ser Glu Thr
        595                 600                 605

Asn Glu Val Phe Val Tyr His Lys Glu Ile Ser Lys Pro Leu Thr Trp
        610                 615                 620

His Arg Phe Gly Thr Leu Asp Met Glu Asp Ala Glu Asp Glu Ala Gly
625                 630                 635                 640

Ser Tyr Phe Ile Ser Ala Val Cys Trp Lys Ser Asp Arg Pro Thr Ile
                645                 650                 655

Leu Thr Ala Asn Ser Gln Gly Thr Ile Lys Val Leu Val Leu Ala Ala
            660                 665                 670

<210> SEQ ID NO 27
<211> LENGTH: 660
<212> TYPE: PRT
<213> ORGANISM: Mus musculus

<400> SEQUENCE: 27

```
Val Ser Gly Ser Ala Ser Ala Gly Gly Ala Val Ser Ala Gly Gln Ser
1               5                   10                  15

Arg Leu Ser Cys Ala Ala Arg Pro Ser Ala Gly Val Gly Gly Ser Ser
            20                  25                  30

Ser Ser Leu Gly Ser Ser Arg Lys Arg Pro Leu Leu Val Pro Leu
        35                  40                  45

Cys Asn Gly Leu Leu Asn Ser Tyr Glu Asp Lys Ser Asn Asp Phe Val
    50                  55                  60

Cys Pro Ile Cys Phe Asp Met Ile Glu Glu Ala Tyr Met Thr Lys Cys
65                  70                  75                  80

Gly His Ser Phe Cys Tyr Lys Cys Ile His Gln Ser Leu Glu Asp Asn
                85                  90                  95

Asn Arg Cys Pro Lys Cys Asn Tyr Val Val Asp Asn Ile Asp His Leu
            100                 105                 110

Tyr Pro Asn Phe Leu Val Asn Glu Leu Ile Leu Lys Gln Lys Gln Arg
            115                 120                 125

Phe Glu Glu Lys Arg Phe Lys Leu Asp His Ser Val Ser Ser Thr Asn
130                 135                 140

Gly His Arg Trp Gln Ile Phe Gln Asp Leu Leu Gly Thr Asp Gln Asp
145                 150                 155                 160

Asn Leu Asp Leu Ala Asn Val Asn Leu Met Leu Glu Leu Leu Val Gln
                165                 170                 175

Lys Lys Lys Gln Leu Glu Ala Glu Ser His Ala Ala Gln Leu Gln Ile
            180                 185                 190

Leu Met Glu Phe Leu Lys Val Ala Arg Arg Asn Lys Arg Glu Gln Leu
            195                 200                 205

Glu Gln Ile Gln Lys Glu Leu Ser Val Leu Glu Glu Asp Ile Lys Arg
210                 215                 220

Val Glu Glu Met Ser Gly Leu Tyr Ser Pro Val Ser Glu Asp Ser Thr
225                 230                 235                 240

Val Pro Gln Phe Glu Ala Pro Ser Pro Ser His Ser Ser Ile Ile Asp
            245                 250                 255

Ser Thr Glu Tyr Ser Gln Pro Pro Gly Phe Ser Gly Thr Ser Gln Thr
            260                 265                 270

Lys Lys Gln Pro Trp Tyr Asn Ser Thr Leu Ala Ser Arg Arg Lys Arg
            275                 280                 285

Leu Thr Ala His Phe Glu Asp Leu Glu Gln Cys Tyr Phe Ser Thr Arg
            290                 295                 300

Met Ser Arg Ile Ser Asp Asp Ser Arg Thr Ala Ser Gln Leu Asp Glu
305                 310                 315                 320

Phe Gln Glu Cys Leu Ser Lys Phe Thr Arg Tyr Asn Ser Val Arg Pro
                325                 330                 335

Leu Ala Thr Leu Ser Tyr Ala Ser Asp Leu Tyr Asn Gly Ser Ser Ile
            340                 345                 350

Val Ser Ser Ile Glu Phe Asp Arg Asp Cys Asp Tyr Phe Ala Ile Ala
            355                 360                 365

Gly Val Thr Lys Lys Ile Lys Val Tyr Glu Tyr Gly Thr Val Ile Gln
            370                 375                 380

Asp Ala Val Asp Ile His Tyr Pro Glu Asn Glu Met Thr Cys Asn Ser
385                 390                 395                 400

Lys Ile Ser Cys Ile Ser Trp Ser Ser Tyr His Lys Asn Leu Leu Ala
```

```
                        405                 410                 415
Ser Ser Asp Tyr Glu Gly Thr Val Ile Leu Trp Asp Gly Phe Thr Gly
            420                 425                 430

Gln Arg Ser Lys Val Tyr Gln Glu His Glu Lys Arg Cys Trp Ser Val
        435                 440                 445

Asp Phe Asn Leu Met Asp Pro Lys Leu Leu Ala Ser Gly Ser Asp Asp
    450                 455                 460

Ala Lys Val Lys Leu Trp Ser Thr Asn Leu Asp Asn Ser Val Ala Ser
465                 470                 475                 480

Ile Glu Ala Lys Ala Asn Val Cys Cys Val Lys Phe Ser Pro Ser Ser
                485                 490                 495

Arg Tyr His Leu Ala Phe Gly Cys Ala Asp His Cys Val His Tyr Tyr
            500                 505                 510

Asp Leu Arg Asn Thr Lys Gln Pro Ile Met Val Phe Lys Gly His His Arg
            515                 520                 525

Lys Ala Val Ser Tyr Ala Lys Phe Val Ser Gly Glu Glu Ile Val Ser
    530                 535                 540

Ala Ser Thr Asp Ser Gln Leu Lys Leu Trp Asn Val Gly Lys Pro Tyr
545                 550                 555                 560

Cys Leu Arg Ser Phe Lys Gly His Ile Asn Glu Lys Asn Phe Val Gly
                565                 570                 575

Leu Ala Ser Asn Gly Asp Tyr Ile Ala Cys Gly Ser Glu Asn Asn Ser
            580                 585                 590

Leu Tyr Leu Tyr Tyr Lys Gly Leu Ser Lys Thr Leu Leu Thr Phe Lys
        595                 600                 605

Phe Asp Thr Val Lys Ser Val Leu Asp Lys Asp Arg Lys Glu Asp Asp
    610                 615                 620

Thr Asn Glu Phe Val Ser Ala Val Cys Trp Arg Ala Leu Ser Asp Gly
625                 630                 635                 640

Glu Ser Asn Val Leu Ile Ala Ala Asn Ser Gln Gly Thr Ile Lys Val
            645                 650                 655

Leu Glu Leu Val
        660
```